United States Patent
Lundstedt et al.

(10) Patent No.: US 8,010,309 B2
(45) Date of Patent: Aug. 30, 2011

(54) ON-SITE ANALYSIS SYSTEM WITH CENTRAL PROCESSOR AND METHOD OF ANALYZING

(75) Inventors: Alan P. Lundstedt, Cinicinnati, OH (US); Allen L. Hall, Toccoa, GA (US); Ching-Hui Tseng, West Chester, OH (US)

(73) Assignee: Cognis IP Management GmbH, Duesseldorf (DE)

( * ) Notice: Subject to any disclaimer, the term of this patent is extended or adjusted under 35 U.S.C. 154(b) by 0 days.

(21) Appl. No.: 12/914,866

(22) Filed: Oct. 28, 2010

(65) Prior Publication Data

US 2011/0054864 A1    Mar. 3, 2011

Related U.S. Application Data

(60) Continuation of application No. 11/707,013, filed on Feb. 15, 2007, now abandoned, which is a division of application No. 10/188,972, filed on Jul. 5, 2002, now Pat. No. 7,194,369.

(60) Provisional application No. 60/307,347, filed on Jul. 23, 2001, provisional application No. 60/307,348, filed on Jul. 23, 2001.

(51) Int. Cl.
    *G06F 17/10* (2006.01)
(52) U.S. Cl. ........................................ 702/104
(58) Field of Classification Search ............. 2/104
    See application file for complete search history.

(56) References Cited

U.S. PATENT DOCUMENTS

2002/0042274 A1 * 4/2002 Ades .......................... 455/445

* cited by examiner

*Primary Examiner* — Tung S Lau
(74) *Attorney, Agent, or Firm* — Diehl Servilla LLC

(57) ABSTRACT

A method of analysis, analysis system, program product, apparatus, and method of supplying analysis of value incorporating the use of at least one data acquisition device, a central processor, and a communication link that is connectable between the data acquisition device and the central processor. The central processor is loaded with multivariate calibration models developed for predicting values for various properties of interest, wherein the calibration models are capable of compensating for variations in an effectively comprehensive set of measurement conditions and secondary material characteristics. As so configured, the calibration models can compensate for instrument variance without instrument-specific calibration transfer. Measurement results generated by the central processor can be transmitted to an output device of a user interface.

11 Claims, 22 Drawing Sheets

ON-SITE ANALYSIS SYSTEM WITH CENTRAL PROCESSOR AND METHOD OF ANALYZING

CROSS-REFERENCE TO RELATED APPLICATIONS

This application is a continuation of U.S. patent application Ser. No. 11/707,013, filed Feb. 15, 2007 (now pending), which claims priority under 35 U.S.C. §120 and is a divisional of U.S. patent application Ser. No. 10/188,972, filed Jul. 5, 2002 (now U.S. Pat. No. 7,194,369, issued Mar. 20, 2007) which in turn claims priority under 35 U.S.C. §119(e) of U.S. Provisional Patent Application Nos. 60/307,347 filed Jul. 23, 2001 and 60/307,348, filed Jul. 23, 2001 (now expired), the entire contents of which each of the aforementioned patent applications are incorporated herein by reference. This application is also related to U.S. patent application Ser. No. 10/188,853, filed Jul. 5, 2002, the disclosure of which is incorporated herein by reference.

STATEMENT REGARDING FEDERALLY SPONSORED RESEARCH OR DEVELOPMENT

Not applicable.

FIELD OF THE INVENTION

The present invention is generally directed to a process for analyzing materials, preferably at multiple locations. More particularly, the present invention relates to a method of rapid analysis which utilizes analytical instrumentation, for example spectroscopic sensor units, on site to transmit and receive information to and from a central processor. The invention also relates to a system for acquiring data from a sample at remote site locations concerning a property of interest of that sample, transmitting the data to the central processor for data analysis, and receiving and optionally displaying processed information at those locations. Further, the invention relates to a method of providing analysis services to customers from a central processor.

BACKGROUND OF THE INVENTION

There are numerous instances where one or more properties of a material are preferably analyzed at one or more locations removed from an analytical laboratory where testing would normally be conducted. For example, agricultural products may be analyzed for the presence and concentration of certain components during the crop growing stage, at harvesting, during transportation, or after the product has been stored, as at a grain silo. Other non-limiting instances where this type of analysis would be useful include applications in the processed food industry, the mining industry, the chemical industry, the finished hard goods industries, and a variety of service, retail sales, and medical industries.

In the absence of equipment or skilled personnel for conducting sample analysis at the location of the sample, substantial time delays can result in initiating and completing an analysis. Thus in the case of the analysis of an agricultural product such as an oil seed which would be harvested within a narrow window of time, traditionally specific characteristics of the seed are determined by a laboratory. This is due to the fact that the equipment and skilled personnel generally required to conduct such analyses are not normally available to the farmer or even to the silo operator. Thus, if an oil seed is to be analyzed, a sample is taken from the farmer's truck or from the silo operator and sent to an independent laboratory for analysis. It is not uncommon in this situation for the sample to require one day for forwarding to the laboratory, two days for the laboratory to conduct the analysis, and an additional day for the results to be returned to the silo operator. Thus, a particular lot of oil seed may require four days to be analyzed. Where the value of the oil seed is dependent on the analysis, utilizing laboratory analysis results in substantial delays to the farmer in obtaining a value for his crop, to the silo operator in valuing the crop and determining the market into which the seed will be sold, and to the ultimate purchaser of the oil seed. When one considers that in the case of oil seed harvesting the oil seed crop typically is processed within a narrow window of time over a wide geographic area, the individual delays described above become multiplied at each silo within the crop growing region.

Alternatively, it is known to analyze certain components of a particular agricultural product at the location where the material is either grown, harvested, transported, or stored. Nevertheless, this resultant analysis of the product may not be directly comparable to an analysis of the same agricultural product in a different location, even though using the same methodology. Even when the same sample is analyzed at different locations, differences in analytical results may arise, for example, because of a difference in environmental conditions at one analysis location relative to the other or because of a difference in the performance of the analyzers. Results may also differ because of variations in the procedure of presenting the sample to different analyzers.

It may be convenient or necessary for on-site analyzers to be able to be easily transported from one location to another. A portable sensor unit or spectrometer is one that is sufficiently compact and robust to permit it to be transported to alternate testing locations as needed. These units are able to be removed from service and returned to service quickly for transportation to and use at a desired site for analysis. The analytical instruments for such analysis must be rugged and capable of making repetitive analyses without extensive recalibration by a skilled operator and with little or no variation over the course of use of the unit.

Because the analysis of, for example, a particular agricultural product may need to be determined at locations over a wide geographic area within a narrow time frame, it may become impractical to conduct the analyses using only one instrument. Generally it then becomes necessary to test these products at multiple sites with multiple analyzers. Under these circumstances, each of the analyzers must be calibrated so that the output results from the various analyzers can be properly compared. Depending on the type of analysis, with traditional techniques the analytical results of a particular agricultural product using multiple analyzers may vary because of different effects resulting from the environmental, instrument, or sample presentation variations discussed above. To address this, either each analysis should be conducted under the same environmental and sample presentation test conditions, or each analysis should be completed with the ability to compensate for differences in temperature, humidity and other relevant environmental variations in generating data by the individual analyzers. Further, results generated by different analyzers may differ because of inherent manufacturing differences between the highly sensitive instrument components and differences in the precise assembly of the components, the differences becoming more pronounced over time producing instrument drift. As a result, no two analytical instruments are precisely identical to one another, so accommodation must be made in considering the results generated by an analyzer when comparing the results with those from other units. While work has been done to develop practical methods for transferring multivariate calibrations between instruments, for example as discussed in U.S. Pat. No. 5,459,677, these methods require that some instrument, sometimes called a reference instrument or a master instrument, be maintained in some known or reproducible state or be capable of being brought into a reproducible and well defined state to achieve instrument standardization. Then, a master calibration model developed on one instrument can be transferred to a number of target instruments. However, all calibration transfer and instrument standardization methods require additional steps to be taken at various times potentially over a range of time intervals after the initial calibration transfer. For example, the analyst may have to evaluate a set of calibration transfer samples on the target instruments after the initial calibration transfer, usually by a skilled operator, and adjust either the models or the instruments so that the response from the target instruments agrees with the response from the master or reference instrument. Further, the measurement conditions of the material samples being analyzed, for example the sample temperature, may also be different at the various sites. Again, accommodations must be made in considering the results generated from those material samples.

Another matter to be considered in conducting remote analyses of materials such as agricultural products is the amount and quality of information desired from the analysis, and the demands placed on the analyzer. Generally, as the analyzer is able to perform more sophisticated analysis, the analyzer itself becomes more complex, a higher level of training is required to operate the analyzer and interpret the results, and the weight and size of the instrument may increase as a result. An analyzer capable of undertaking more complex analyses is generally more susceptible to damage and to generating inaccurate results by the process of moving the analyzer from site to site, utilizing the analyzer under varying conditions, and the like. Consequently, the results from such an instrument are more likely to change and thus render comparison between various remote analyzers more difficult or even impossible.

The need to be able to generate comparable, statistically equivalent analyses of materials at remote site locations can extend to a wide range of materials in addition to agricultural products such as, but not limited to, manufactured products, natural phenomena, ores, renewable raw materials, fuels, and living tissue.

The combination of a calibration model with an analytical instrument to generate a predicted result has been practiced. It is known to use, for example, calibration models associated with near-infrared, mid-infrared, and Raman spectrometers in commercial processes to monitor the status of chemical reactions. This monitoring capability can involve the generation of results from an analytical method with the application of statistical analysis and calibration models to interpret and quantify the data. For example, in the manufacture of carboxylic acids and derivatives from fats and oils, it is known to use near-infrared spectrometers loaded with the appropriate chemometric software to measure a number of properties of the carboxylic acids and their derivatives. This monitoring can be done during the manufacturing process on intermediate product, as well as on the finished product. The spectrometer can be operated in a stand-alone mode with the operator bringing samples to the spectrometer for at-line analysis. Alternatively, the spectrometer can be connected in-line to enable monitoring of the process stream as the manufacturing operation proceeds. Thus, two commercially available near-infrared spectrometers such as the Bomem MB-160 FT-NIR spectrometer loaded with HOVAL software (such as Version 1.6, 1992) and AIRS software (such as Version 1.54, 1999) from Bomem Inc., Canada, and the Bruker Vector 22/N spectrometer loaded with OPUS-NT Quant-2 software (such as Version 2.6, 1999) from Bruker Optik GmbH, Germany have been used to analyze intermediate and finished carboxylic acid products for acid value, iodine value, titer, viscosity, hydroxyl value, saponification value, composition of fatty materials and derivatives, and for the presence of carboxylic acid methyl ester contaminants in a specific carboxylic acid.

The calibration models for evaluating the above properties were derived from the Grams-PLS plus (Version 3.01 B, 1994, Galactic Industries Corporation) and Bruker OPUS Quant-2 software. In those instances where more than one data acquisition device was used to generate predicted results for a particular property of interest, individual calibration models were developed for corresponding individual instruments or a master calibration model was developed on a particular master instrument, transferred to one or more other instruments, and adjusted with instrument-specific correction factors to standardize the predicted results across multiple instruments.

In determining the chemical properties of incoming raw materials such as tallow, coconut oil and palm kernel oil for the production of carboxylic acids, near-infrared spectrometry with appropriate chemometric techniques such as the partial least squares (PLS) method has been used to evaluate the free carboxylic acid content of the starting materials, as well as iodine value and moisture content. The near-infrared monitoring can also be used to monitor the progress of the transesterification process utilizing fatty triglycerides and methanol as reactants. A near-infrared spectrometer connected to transesterification process equipment can also monitor free glycerine content, bound/combined glycerine content and methyl ester concentration. Alternatively, samples can be taken during the progress of the reaction to a stand-alone near-infrared spectrometer loaded with appropriate calibration models for off-line analysis. In connection with the monitoring of the progress of a reaction, the near-infrared spectrometer can utilize a fiber optic probe connected to the spectrometer by fiber optic cable. The use of the near-infrared spectrometer in combination with the application of modeling software permits analysis of particular chemical species during the progress of chemical processing, as well as at the conclusion of the chemical process. Spectrometers such as near-infrared operating in the in-line mode are capable of providing data substantially on a real time basis. Data generation in these instances occurs under tightly controlled test and environmental conditions and involves one or more probes connected to a single instrument connected to a single data processing unit.

There is presently a high interest in the analysis of agricultural products. Genetically modified materials are of particular interest. The grain and food distribution segments in agriculture have expressed significant need for analytical technology to meet market requirements to identify and quantitate genetically modified crops, especially corn and soybean, in world markets. This need has developed rapidly. U.S. farmers have increasingly accepted crops derived from genetic engineering after the success they experienced in the 1996 growing season. The U.S. Department of Agriculture estimated that approximately 25% of U.S. corn and 54% of U.S. soybeans produced in 2000 were grown from genetically engineered seed with input traits to provide resistance to herbicides, insects, or both. The composition of such input trait crops is generally macroscopically indistinguishable from similar crops without the corresponding input traits.

In contrast, the foods of the future which will incorporate improvements of direct benefit to the consumer likely will be based at least in part on crops having enhanced output traits. The composition of these enhanced crops is different from the corresponding conventional crops. Examples include high oil corn, high sucrose soybeans, and low linolenic canola. Genetically-enhanced crops can be produced either by genetic engineering, as enabled by recent advances in biotechnology, or by specially designed traditional breeding programs. Even traditional crop improvement practices can result in plants with changed genetics and enhanced properties.

The growth and the need for analytical technology for agricultural products has been the promulgation of labeling regulations adopted in many regions of the world including the two largest agricultural commodity trading communities, the European Union and Japan. These labeling requirements have required or are expected to require food processors to label finished food products as to the genetically modified content of the ingredients used to produce these products. The initiation of labeling and the growing number of food processors electing to use raw materials which have not been genetically modified are driving the need for identity preservation.

Labeling specifications are nearing completion in both Europe and Japan. Identifying the genetic composition of grain in commercial crops and maintaining that identity throughout the agricultural complex to support labeling has become a high priority for seed companies, commercial growers, distribution and process companies, as well as food processors and is expected to increase as labeling is further implemented in the future. Consequently there is a need to provide an economical and efficient way to analyze seeds and crops at various locations along the supply chain, to identify and quantify the chemical composition and potentially other measurable properties of one or more output traits in genetically enhanced as well as conventional crops.

The interest in obtaining detailed analysis of agricultural products extends also into areas involving analysis of other materials. There remains a need as to other materials in providing an economical and efficient way of analyzing materials on site at remote locations to identify and quantify their chemical compositions and other properties of interest.

BRIEF SUMMARY OF THE INVENTION

The present invention is directed to a process for identifying and quantifying one or more properties of interest of a material, the process involving providing a material to be analyzed; providing one or more data acquisition devices capable of acquiring data for prediction of one or more properties of the material; providing a central processor capable of computing one or more predicted results using multivariate calibration models and storing a database of multivariate calibration models; providing a communication link between data acquisition devices and the central processor; and analyzing the material using the data acquisition devices and the central processor in order to obtain results on one or more properties of interest. Preferably the central processor stores at least a portion of either measurement data, measurement results, or both. Preferably the data acquisition devices are capable of being transported from site to site. The calibration model is multivariate, and compensates for an effectively comprehensive set of measurement conditions and secondary material characteristics. Preferably, the communication link is capable of providing resultant information from the central processor to a user interface in the vicinity of the sensor. However, the resultant information may be conveyed by other means, such as by telephone communication, or may be conveyed by the same type of communication link as available between data acquisition device and central processor but to a location removed from the data acquisition device.

The invention is also directed to an analysis system comprising a central processor loaded with one or more calibration models, at least one data acquisition device connected to the central processor to supply input information, and a user interface to initiate data acquisition and to optionally provide an indication of the results generated by the central processor. A user interface may receive user input and present results to users using any known user-interface technologies, where user input can be provided by a keyboard, mouse, touch-screen, voice recognition, dedicated buttons, and the like, and presentation of results by a visual display, speech synthesis, printed pages and the like. A user interface may comprise multiple units or may be incorporated into a single device, including into the same device as a data acquisition device. Furthermore, user input may be received by multiple devices, and/or multiple devices may provide output to a user. Generally, the central processor includes a data repository to store at least resultant information, but the repository may also include at least a portion of the information acquired at the data acquisition device. The invention also encompasses a method for providing analysis of value to a customer.

Understanding of this subject matter is facilitated through the defining of certain key terms. The property of interest of a sample of material being analyzed is referred to herein as the primary variable. This variable is distinguished from other variables which influence the instrument response, which are identified as secondary variables.

Analytical instruments do not generate the values of a property of interest directly. Rather, measurement signals such as voltage or current are generated by the instruments. These signals may be pre-processed by transforming the raw data using instrumental transduction and computation steps performed by internal electronics, computer circuit boards, and the like to a form more readily assimilated by subsequent processing steps. These optionally pre-processed measurement signals are called the instrument output or the instrument response. An instrument is unable to analyze a sample of a material without the creation of a statistically valid relationship between the instrument response and known values for the property of interest of the material. The process of developing such a relationship is known as calibration.

The collection of all variations in secondary variables resulting from variations in the performance of one or more instruments is the instrument variance. Instrument variance encompasses variations both in the instrument components and in the assembly of the components, and encompasses variations which develop over time, but does not encompass operator variation in the use of the instrument, or other factors distinct from the instrument hardware which affect the observed value.

The actual mathematical relationship between the instrument response and the property of interest of a material is called the calibration model. To develop the model, the particular analytical instrument, employing a particular analytical method, is trained to measure a particular property of interest through development of a mathematical relationship between the instrument response and known values of the property. Experimental data related to the property of interest are generated by recording values of the property of interest determined by a reliable independent method on a particular group of samples. These recorded values are called known values. It is recognized that the experimentally determined values of the known data are characterized by experimental uncertainties, so the known values are not known exactly.

The group, or set, of samples of a material with known values of the property of interest used to develop this calibration model is called a calibration set. Variations in the material characteristics that are expected to be present in the population of samples that will be analyzed in the future should be represented by samples in the calibration set. This calibration set, or more typically a subset thereof, is then used to generate a collection of instrument responses over a range of measurement conditions for evaluating the property of interest. The collection of known values and instrument responses generated from the calibration set over a range of measurement conditions is a data set called the training set. Because each sample in the calibration set may be subjected to a range of conditions involving a number of secondary variables, as well as repeated measurements under the same conditions, the training set may contain more values than the number of samples comprising the calibration set. A training set generally encompasses both variations in a range of material characteristics and variations in a range of measurement conditions that are expected to be present during actual on-site analyses in the future.

As used herein, secondary material characteristics are material characteristics other than the property of interest that may influence the instrument response. The primary material characteristic is the property of interest. The collection of all variations in secondary variables resulting from variations in the secondary material characteristics of one or more samples of a material is the sample variance. Sample variance encompasses variations both within samples and between samples of a material. Variations in the primary material characteristic are encompassed by particular values in the training set spanning the expected range of the property of interest.

A validation set is another data set of known values and instrument responses generated from the calibration set, or more typically a subset thereof, or from a new set of samples of the same material with known values over a range of measurement conditions, such that this data set is usually distinct from the training set. The validation set is used to test the predictability of the calibration model that was developed using the training set. As used herein, an instrument-response set is defined as a data set that can be used as either a training set or a validation set.

The known values corresponding to the property of interest of the samples used to generate an instrument-response set may be determined by measurements using a validated analytical technique herein referred to as a primary analytical method. These known values are considered to be observed values that are suitable for use as reference data in developing a calibration model for a secondary analytical method. As used herein, the known or observed values corresponding to the property of interest for a set of calibration samples will be treated in the same manner regardless of whether the values were those of reference standards or the values were measured by a primary analytical method.

A remediation update is a new calibration model that is developed by generating new instrument responses for a previous training set without necessarily modifying the calibration set or the particular levels of measurement conditions of the previous training set in order to re-establish previously attained calibration statistics. Remediation updates are often needed to compensate for changes in instrument variance over time. Since the usable lifetime of calibration samples may be shorter than the time interval between recalibrations, a remediation update may be generated from newly prepared samples of the same material covering a similar range of material properties as those of a previous calibration set.

In comparison, an enhancement update is a new calibration model that is developed from a training set which has been altered from a previous training set for the purpose of improving some prediction capability of a model. An enhancement update may be developed from combinations of an extended training set that includes additional calibration data to span a wider range of either sample characteristics or measurement conditions, or both; a corrected training set that includes modified calibration data or excludes erroneous calibration data to correct errors discovered in a previous training set; or an improved training set that includes new calibration data, some of which may replace corresponding values in a training set, where the new values may result from improvements in a primary analytical method used to generate better estimates of known values or from an improved representative sampling of the material. An improved training set may also be developed by selecting a different set of calibration samples or measurement conditions for the new training set, where the number of observations may be greater than, the same as, or less than that used in a previous training set.

A global training set is a training set configured to compensate for an effectively comprehensive range of variation in the secondary variables in connection with predicting the property of interest from a calibration model.

The term compensation as used herein is defined as the reduction or elimination of the impact of variation in one or more factors on the predicted result.

If the output of an analytical instrument depends only on the property of interest, a univariate calibration model would be created. Generally, a univariate calibration model is rarely developed because a number of additional variables are usually encountered which affect the instrument response. Such other variables may include impurities in the sample and the temperature of the sample. Where more than one variable affects the instrument response, the calibration model generated to interpret the instrument response is considered multivariate. Thus, a multivariate model having n variables of the instrument response R is defined mathematically as $$R = f(x_1, x_2, \ldots, x_n),$$

where $x_1$ is the property of interest and $x_2$ to $x_n$ are the additional n−1 variables that affect the instrument response R.

The objective of calibration model development is to predict the instrument response from known values of the property of interest in the presence of variations of the secondary variables. A training set for the calibration model is developed by generating instrument responses at different levels spanning the expected ranges, or a portion of these ranges, of the primary and secondary variables. In the development of a calibration model, the instrument response is a dependent variable, and the primary and secondary variables are identified as independent. The dependent variable is the presumed effect or response to a change in the independent variables. Independent variables are also known as predictor variables.

After the calibration model is developed, it is rearranged to express the property of interest as a function of the instrument response and the secondary variables. The measurement process predicts, or measures, the property of interest by using the analytical instrument response generated for an unknown sample as input to the calibration model. The primary objective of calibration model use is to predict the property of interest from the instrument response in the presence of variations of the secondary variables. In actual situations where the calibration model is multivariate, the relationship of the property of interest to the instrument response is affected by the presence of secondary variables, which include all other factors that will significantly influence the instrument response. These secondary variables may be described alternatively as influential factors, interfering factors, or contaminating factors in the measurement process.

The quality of a calibration model can be described by calculating the degree of correlation between the known values and the corresponding predicted results using a training set or a validation set. One such process is called cross-validation, wherein the same observations of a training set are used for two different purposes, model building and validation. As used herein, an observation is the data corresponding to a single measurement process. One version of cross-validation is known as the leave-one-out method, involving a training set of M observations with repetition of building the calibration model M times. Each time, one observation (the $i^{th}$) is excluded and the remaining M−1 observations are used to build the $i^{th}$ calibration model, where i ranges from 1 to M. The excluded observation is then used to validate the $i^{th}$ model, whereby the $i^{th}$ residual is computed as the difference between the $i^{th}$ predicted value and the $i^{th}$ known value.

The statistical measure of the degree of correlation between the known values and the corresponding predicted results of the data set is the square of the correlation coefficient, known as $r^2$. The square of the correlation coefficient is also known as the coefficient of determination, which measures the fraction of the variation in the dependent variable about its mean that is explained by variation in the independent or predictor variables. The total variation in a set of predicted values is the sum of two parts, the part that can be explained by the model and the part that cannot be explained by the model. The ratio of the explained variation to the total variation, or $r^2$, is a measure of how good the model is. The $r^2$ statistic is therefore a measure of the strength of the relationship between the observed and predicted values. The values of $r^2$ range from 0 to 1, and cover the range of no correlation up to perfect correlation. In practice, these two extremes are rarely if ever encountered. High values of $r^2$ indicate that the model tends to determine its predictions with small errors. $R^2$ is defined as 100 times $r^2$, so the values of $R^2$ range from 0 to 100. Additional information on these and related statistical terms can be found in "Multivariate Calibration", 1989, John Wiley & Sons, Ltd. by Harold Martens and Tormod Naes; and "Chemometric Techniques for Quantitative Analysis", 1998, Marcel Dekker, Inc. by Richard Kramer, both texts of which are incorporated herein by reference.

Samples with known values of the property of interest are called known samples. These samples are distinct from other samples called unknown samples, for which values of the property of interest may not be known.

It is possible that the measurement of an unknown sample may generate a value which is not a valid prediction by the existing calibration model. This invalid predicted value is called an outlier. An outlier may be an observed measurement which deviates so much from other observations as to arouse a suspicion that the sample was taken from a population distinct from that used to create the calibration model. Alternatively, an outlier may be a false positive observation which does not deviate noticeably from valid observations but belongs to an overlapping, contaminating population. An outlier is always a value that is distinct from a basic population of valid predictions of a property of interest. Generally it is expected that large gaps would be noted between observations of outliers relative to observations of acceptable values which fall within the basic population. However, the distinction between acceptable and outlier observations is not always clear-cut because contaminating distributions can overlap the basic distribution. In practice then, it is expected that not all outliers will be identified. The determination of an outlier is done with a statistical probability rather than with certainty.

Some outliers may be caused by invalid measurements, such as when an instrument malfunctions to produce an abnormal spectrum or when an incorrect type or insufficient quantity of sample is measured. Other outliers may result from the inadvertent use of erroneous values of known data in a training set or a validation set. Outliers caused by invalid measurements or erroneous calibration data are called bad outliers and the corresponding predicted values should be considered to be invalid results. In other situations, outliers may be valid measurements of samples or measurement conditions which fall outside the range of primary or secondary variables spanned in the training set. In still other situations, outliers may result from valid measurements in which some previously unidentified secondary variable has become an influential factor. In these latter two situations, such outliers are called good outliers since they identify opportunities to extend the training set to cover a wider range of samples and measurement conditions. While the predicted values of good outliers should also be considered to be invalid results, if a new calibration model is developed by including a range of such good outliers in the training set, future measurements will be capable of generating valid results over a wider range of samples and measurement conditions.

There is no unequivocal test to determine whether an observation is an outlier. The possibility of an observation being an outlier is determined by the type of test used to evaluate that observation. In a situation where the distance of an observed data point from a central measure of a population can be an indication of an outlier, the operator can employ the Mahalanobis distance to determine the existence of a possible outlier. The Mahalanobis distance is the scalar distance between a multivariate observation and the centroid of a multivariate distribution that takes into account the actual spatial distribution of values in multidimensional space. A typical cutoff point or threshold value for determining if an observation is considered to be a probable outlier is a Mahalanobis distance that is often found to be in the range from 0.1 to 1. At values lower than the threshold, there is typically insufficient reason to exclude the observation. Such observations are presumably valid. Depending on the desired probability of detection, the threshold value of the Mahalanobis distance value which would be an indicator of a probable outlier may be adjusted downwardly or upwardly to increase or decrease the probability of detection. However, increasing the probability of detecting an outlier also increases the probability of rejecting valid observations. Alternatively, a recommended threshold value for detecting a probable outlier can be computed by chemometric software such as OPUS Quant-2 from the observed distribution of Mahalanobis distances in the training set. The reference method used for determining Mahalanobis distance (MAH) was ASTM E 1790-96.

It has been found that different threshold values of the Mahalanobis distance can be used to classify probable outliers into a small number of different categories according to the probable reason that the observed value is a probable outlier. Thus, for example, Mahalanobis distances in the range from about 0.4 to about 1.0 often correspond to good outliers, while Mahalanobis distances greater than about 1 often correspond to bad outliers. Furthermore, when the Mahalanobis distance is considerably greater than 1, for example greater than 100, the outlier is extremely bad and often corresponds to a major instrument malfunction such as a non-emitting excitation source or the complete absence of a sample during data acquisition. When the Mahalanobis distance is in the range from about 1 to about 100, the bad outlier often corresponds to smaller problems with the sample, the instrument, the environment or the sample presentation such as when a sample is present during data acquisition but is of a different material from that used to develop the calibration model or when an inadequate amount of sample is detected. Generally, the threshold value for bad outliers is generally at least twice the magnitude of the threshold value for detecting a probable outlier which herein is called the threshold value of good outliers. The threshold value for extremely bad outliers is generally about 100 times the magnitude of the threshold value for bad outliers.

At a basic level, the on-site analysis system comprises one or more data acquisition devices, a central processor, and a communication link. The data acquisition devices are used primarily, though not necessarily exclusively, for data acquisition, and the central processor for data analysis. A packet of information transmitted from an individual data acquisition device to the central processor is called measurement data, and the packet of information transmitted from the central processor to an output device of a user interface in the vicinity of a data acquisition device or to a third party is called measurement results. The data acquisition devices typically are physically separated from the central processor, though two or more data acquisition devices may be at a single location. The data acquisition devices may be geographically separated from each other and the central processor by great distances, but this is not required. As used herein, the data acquisition devices broadly identify the group of devices which acquire information about a sample of a material. Preferably, the data acquisition devices acquire spectroscopic data, though other analytic mechanisms may be employed, such as via chromatography, mass spectrometry or emission detection. Preferably, the data acquisition devices are transportable and are capable of generating an instrument response from data acquired on samples of material at a number of remote locations. The data acquisition device may also include in a single unit the sample presentation device for providing a sample for data acquisition by a detector, and a local processor (such as a laptop computer) with a user interface for executing the steps necessary to generate a measurement result, with an optional output device to read out the measurement result.

The central processor as used herein is a computer system which stores one or more calibration models and manipulates data transmitted from one or more data acquisition devices using the calibration models to predict values for the property of interest of a material. The central processor is not necessarily a single entity, however, since it may reside on multiple computer servers or clustered servers, where some duplication may be provided for redundancy and other duplication may be provided to mirror servers in multiple geographic locations. The use of multiple servers also increases the processing capacity, i.e., the number of transactions which can be completed within a period of time. In practice, the central processor behaves as if it were a single entity at a central location. The group of redundant and mirrored processors is known herein as the central processor. Further, the database of calibration models stored in the central processor is preferably constructed to compensate for expected variations in an effectively comprehensive set of secondary variables to provide statistically equivalent results from different remote instruments over time without instrument-specific calibration transfers or remediation updates.

An advantage of the analysis system is the relationship of the multiple data acquisition devices to the central processor. The system can function with many data acquisition devices located at sites which may be far removed from each other geographically for measuring the properties of a single material, such as an agricultural or mineral ore product. However, the system can also encompass multiple data acquisition devices in the same room or building. The use of a central processor means that all data from each data acquisition device are being manipulated in the same way for predicting a property from a particular model.

The database or library of calibration models stored in the central processor can be modified as desired to provide enhancement updates, add models to expand the capabilities for analyzing new properties, or to delete models that are no longer needed. All modifications to the database of calibration models can be done without making any changes to the hardware or software of individual data acquisition devices. Thus, enhancement updates and new models installed in the central processor can be used to analyze measurement data from all data acquisition devices immediately after installation without the need to separately undertake any remedial action at each of the remote sites, and the measurement results from all data acquisition devices typically are stored in the central processor for subsequent reporting and data analysis. As discussed in more detail below, the influential variations which exist in the test environment, the sample presentation to the data acquisition device, the physical and chemical characteristics of the sample, or the individual data acquisition devices themselves are able to be taken into account in quantifying the particular property or identifying the particular substance being measured. Thus, for example, the quantified measurement of the concentration of a triglyceride in an oilseed in one part of the world can be directly compared with a triglyceride concentration of an oilseed at a different location. Even where only one data acquisition device is connected to the central processor, the improved calibration model permits analysis to be conducted over time without the need for remedially updating the model.

The central processor stores a database of calibration models; receives a plurality of data values from a single measurement process, these data acquired by data acquisition devices, typically spectroscopic, about the particular material of interest; computes values for one or more properties of interest of the material using algorithms or computational procedures to manipulate the data and generate predicted values from the calibration models; and forwards the resultant information which it has generated. Optionally, the central processor sends results back to a user interface of the individual data acquisition devices. The data acquisition devices and central processor preferably transmit information to each other over a communication link, though it is possible for information to be transmitted from the data acquisition device to the central processor using a different communication link than that used for transmitting results. Presently, it is preferred that the information be transmitted in digital form. The communication link broadly is one or more communication pathways, often in a communication network, and may include various combinations of, for example, hard-wired telephone lines, cables, optical fibers, a system of towers or satellites for wireless communication, radio equipment, or combinations sufficient to transmit a signal carrying the desired information between any location and a central processor.

The calibration model based on chemometric methods of multivariate analysis provides the capability for generating useful measurement information even where more than one secondary variable encountered during the data acquisition step of a single measurement process may vary simultaneously, independently, or both.

Traditionally, calibration modeling has focused on variations in the sample and sometimes on one or more secondary variables, but not an effectively comprehensive set of factors in constructing the model. The instant invention not only recognizes the effect of sample variation in connection with developing a calibration model, but also evaluates and compensates for effects due to variation in the environment, the instrumentation, and the sample presentation.

After the potential universe of factors which may affect the characterization of the sample has been identified, it is determined whether one or more factors can be eliminated from consideration by mathematical methods of data pretreatment, whether certain factors must necessarily be considered in connection with developing a training set for the calibration model, or whether certain factors must be controlled in a manner as might be done in a traditional methodology to reduce or eliminate variation during the measurement process. The invention thus takes into account all factors known to a reasonable analyst for characterizing the sample as well as other factors that have not been recognized previously, and then proceeds to minimize the effect of all influential factors to develop an acceptable revision of the calibration model. The inventive method thus initially takes into account a number of factors and variations within each such factor sufficiently wide to span the expected range of variations, and then attempts to compensate for these factors in the process of ultimately creating an acceptable calibration model which contains substantial improvements in predictability and which eliminates or substantially reduces effects such as from instrument drift over time relative to existing calibration modeling techniques.

One method for developing the calibration model involves proceeding in a stepwise fashion, initially compensating for a single secondary variable, comparing the data generated by the thus-created calibration model with data from a reference method, followed thereafter by compensating for a second secondary variable and determining if the correlation improves or if the predictability is acceptable according to some statistical criteria, and repeating this process until an acceptable prediction level is achieved in the presence of variations of all known influential factors. This stepwise process is useful in the feasibility stage to identify influential factors and develop appropriate compensation techniques. Using the extended training set developed in this manner, it becomes more efficient to develop subsequent model revisions by including all factors at one time. Alternatively, the calibration model is initially developed by compensating for, or by otherwise taking into account, a number of known relevant factors at one time. Under these circumstances it is possible that the calibration model will still need to be refined one or more times before an acceptable model exists. However, the number of refinement operations will typically be lower than the number encountered when only one variable is evaluated at a time. In both cases, the goal is to identify all statistically significant factors which might arise from variations in the sample, the environment, instrumentation, and sample presentation; eliminate those factors from consideration which respond to data pretreatment, or satisfactorily reduce their effect; control those factors which may produce greater instrument responses than those from variations in the property of interest; and incorporate into the training set of the calibration model representative data spanning a range of variations for those remaining factors which affect the property of interest.

An example of an environmental variation is temperature change which results in samples having different temperatures at different times of measurement. This variation may affect the predictability of a calibration model generated where there has been no compensation for temperature, or if the measurement occurred at a temperature outside the range of temperatures represented by data in the training set. A number of other variations which may affect the calibration model can be introduced via the measuring instrument. The nature and number of these variations are a function of the type of instrument employed. For example, the incident radiation directed toward a sample using a near-infrared spectrometer has been found to vary as a function of the orientation of the source filament relative to the sample. Also, an older lamp generally does not provide the same light intensity as a new lamp. Concerning the sample presentation variations, the rate at which a sample passes through an incident light beam during a measurement process, or differences in the amount of sample in different measurement processes, may affect the predictability of the calibration model.

It should be recognized that the multivariate calibration models of the invention can be applied to any secondary measurement technique in which a data acquisition device generates multiple data values rather than a single numeric value for each measurement. The plurality of data values may be acquired as discrete values in a digital device, or they may be acquired in continuous fashion from an analog device and then converted into digital format. For example, a spectrum consists of a multitude of intensity values over a range of wavelengths. The spectral data may be acquired continuously or digitally. If the storage location of a single data value is referred to as a data channel, then a multichannel instrument is one for which acquisition of multiple data values may be considered to occur by storing the individual data values in a multitude of individual data channels. Thus, as used herein, a spectrometer that generates a continuous spectrum is a multichannel instrument, since the spectrum could be digitized and the multitude of discrete data values resulting from digitization could be stored in a multitude of individual data channels and could not be stored as a single data value in a single data channel. Hence, the invention applies generally to secondary measurements from multichannel instruments, where a secondary measurement is the prediction of a result from a multivariate calibration model of an analytical method. As discussed below, though the invention will be described in the context of NIR spectroscopy, it should be recognized that the invention can be practiced for any analytical method based on a multichannel instrument.

The samples that will be analyzed at remote locations may not be pure single molecular species, and thus will typically contain several components of which some may be contaminants and others may be distributions of molecular species as occur in synthetic polymers and natural products. Analysis of multichannel data on impure or multi-component samples can contain peaks showing considerable overlap. Chemometric methods of multivariate analysis such as partial least squares (PLS), principal component regression (PCR), artificial neural networks (ANN), and the like allow for determining the properties of interest of multiple components in each sample simultaneously. While the present invention will be described in terms of PLS, it should be understood that other chemometric methods of multivariate analysis can be used to construct calibration models. Multivariate calibrations make use of not just a single data point, but take into account data features over a range of data values, so analysis of overlapping bands or broad peaks becomes feasible.

PLS is one of a number of factor-based methods of multivariate analysis, where a factor space is an alternative coordinate system for a data set, a factor is an axis of the alternative coordinate system or factor space, and the dimensionality of a factor space is the number of axes or factors in the factor space. In a factor-based method of multivariate analysis, the axes of a factor space are selected to most efficiently span the data values in a manner that will capture as much as possible of the systematic variation in the data along a subset of axes or factors.

The total variation in a set of multivariate data is composed of two parts, the part caused by systematic variations in the primary and secondary variables and the part caused by random variation or experimental noise. It is usually found that some factors in a factor space contain only or mostly experimental noise, and such factors are therefore not related significantly to variations in the primary and secondary variables. Thus, it becomes possible to reduce the number of axes in a factor space relative to the number of axes in the original coordinate system of the data by omitting factors or axes that contain only or mostly experimental noise. The dimensionality of the factor space that is sufficient for predicting results to an acceptable level of precision is therefore generally smaller than that of the original coordinate system. The number of factors remaining after such a reduction in dimensionality is called the rank of the factor space. The rank characterizes the dimensionality of the fit of a calibration model to the data. It is generally preferred to avoid overfitting a model by selecting a smaller rank when possible.

The invention is also directed to a method which can support the analysis needs of customers, particularly where the materials to be analyzed are in locations geographically removed from each other and the operators are not skilled in analytical methodology. The method may also support the customer's transactions, the underlying contract agreements, material rating and billing functions, and further data analysis of material. The method utilizes the analysis method and system hardware described herein, encompassing a collection of processing, infrastructure and software components that support multiple application models that involve collection of data, transmittal of that data over a communication link, analysis of that data by appropriate software applications to derive value from the data, storage of the analyzed data in a repository for generating historical statistics, identity preservation and tracking, auditing, forecasting and model improvement, and delivery of results back to the original submitter or an alternate location over the same or different communication link.

It is therefore an object of the invention to provide a calibration model for a property of interest which can accommodate an effectively comprehensive range of variations in one or more characteristics of the material to be analyzed, the instrument, the environment, and the sample presentation without need for remedial model updating.

It is a further object of the invention to provide an analysis system which utilizes calibration models capable of compensating for a range of secondary variables.

It is a further object of the invention to provide an analysis system which provides for at least one data acquisition device and a central processor in combination with a calibration model algorithm to be able to accommodate an effectively comprehensive range of variations of primary and secondary variables, which can generate analysis data on the material to be analyzed.

It is a further object of the invention to provide an analysis system which provides for multiple remote data acquisition devices and a central processor which can generate analysis data on multiple samples of materials remote from each other but which are each analyzed using the same calibration model algorithm for the particular property being measured.

It is a further object of the invention to provide an analysis system which incorporates a user interface in combination with the data acquisition device to provide analysis information generated by the central processor for a particular sample being measured at the location where the measurement is taken.

It is a further object of the invention to provide a method of analysis which permits the measurement of one or more properties of materials utilizing a single calibration model algorithm for each property at a central processor.

It is a further objective of the invention to provide a method of analysis incorporating a calibration model algorithm that has been constructed to compensate for an effectively comprehensive set of expected variations in sample, sample presentation, environmental conditions and instrument.

It is a further object of the invention to provide a method of analysis which permits the measurement using multiple instruments of one or more properties of materials located in remote locations utilizing a single calibration model algorithm without incorporating instrument-specific parameters in the algorithm.

It is a further object of the invention to provide a method for analyzing materials at remote locations, e.g., for multiple customers, individuals, entities, or the like.

These and other objects and advantages of the invention are provided in the detailed description of the invention and in the drawings.

DETAILED DESCRIPTION OF THE INVENTION

Figure 1:
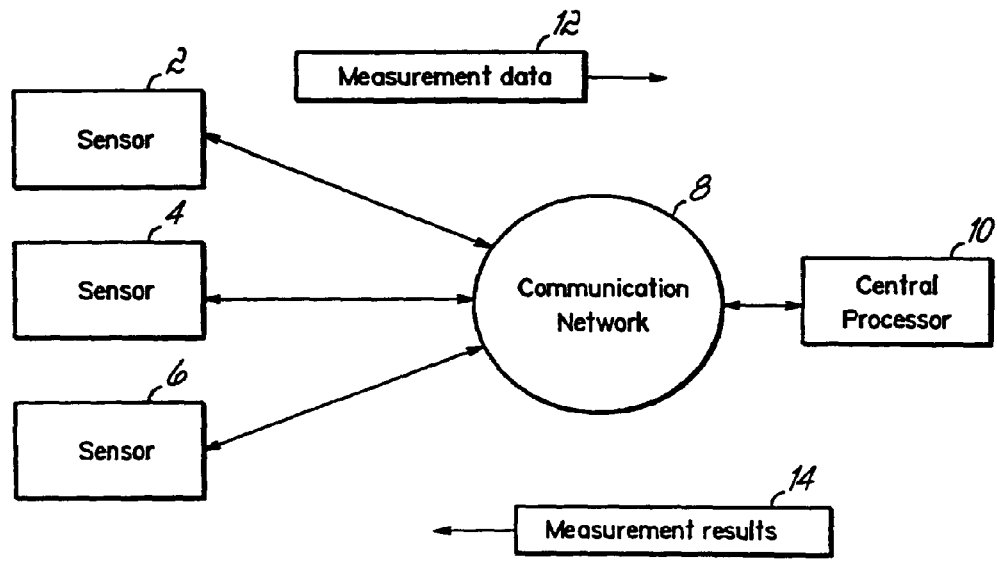
FIG. 1 is a block diagram of an on-site analytical system.

The invention is directed in part to a method of characterizing a material for at least one property of interest comprising acquiring multichannel data on at least one multichannel signal from a sample of the material using a data acquisition device at a location, transmitting the multichannel data along a communication link to a central processor wherein the central processor includes at least one algorithm for manipulating the multichannel data and evaluating at least one multivariate calibration model which can accommodate a range of variables distinct from the variation in the property of interest of the sample, manipulating the multichannel data by the central processor to generate a result predictive of the property of interest of the sample, and forwarding the result from the central processor. The result is typically forwarded to one or more locations remote from the central processor. Preferably, the calibration model can compensate for at least instrument variance. Preferably, the result is transmitted to a user-interface output device in the vicinity of the data acquisition device along the same communication link used for connecting the data acquisition device with the central processor. The result, however, can be forwarded to a different location utilizing the same or a different communication link as desired. Various user interfaces can be provided at one or more locations to enable a user to communicate with the central processor, a data acquisition device, or both. The method of analyzing can encompass a single data acquisition device in a location physically remote from the central processor, or can alternatively include a plurality of data acquisition devices which communicate with the central processor by a communication link. The calibration model loaded onto the central processor is multivariate, and preferably compensates for variations in an effectively comprehensive set of actual measurement conditions and secondary material characteristics.

In generating this calibration model the secondary variables or influential factors that can significantly impact an instrument's response are identified experimentally. These factors have the potential to influence the results predicted from the model. Generally, it is not possible to determine a priori if a particular variable will influence the results predicted from the model. Thus, these variables are described as potentially influential factors until their status is validated experimentally. It is not necessary to determine the actual physical or chemical cause of a potentially influential factor to identify such a factor experimentally or to generate calibration data resulting from systematic or random variations in the level of such a factor. The modeling process utilized herein accounts for a fundamentally wider range of potentially influential factors, while accommodating for this range of factors in a manner which substantially decreases the amount of time required to maintain the model since the need to develop remedial updates is avoided.

The invention also relates to the analytical system comprised of at least one data acquisition device in a remote location, and a central processor loaded with one or more calibration model algorithms and connectable by a communication link to the data acquisition device during the measurement process. Preferably, the system also comprises a user-interface that is connectable to the central processor over a communication link and an output device connected to the user interface to receive a result generated by the central processor. Preferably, the output device is located in the vicinity of the detector. Further, the output device preferably is connected to the central processor by the same communication link connecting the data acquisition device and the central processor.

It is known to employ multivariate calibration modeling in connection with analytical techniques to predict a result. Generally, these calibration models were generated by first determining the property of interest and focusing on variables relating to variation of material characteristics in the population of samples. Generally, attempts were made to eliminate the effects due to other influential variables by controlling those parameters which might vary. The calibration model generated in this way might maintain an acceptable degree of predictability for a period of time, but eventually would reach a point when the accuracy of the predicted values was unacceptable. At that time, the calibration model would have to be regenerated, or the instrument re-calibrated using a remediation update or adjustments to the instrument hardware.

The multivariate calibration model disclosed herein considers actual measurement conditions as they are expected to occur during future measurements and identifies an effectively comprehensive set of factors or experimental variables which can significantly impact the instrument response. Broadly, the multivariate calibration model employed in the invention is developed by identifying potentially influential factors which may significantly impact the response of the instrument. Experiments are then run to determine whether the potentially influential factors are indeed influential by recording information generated by the instrument, such as a spectrum, at different levels of individual factors or combinations of factors. If this information at different levels of factors shows no significant differences, then these factors are not influential in connection with predicting a value for the property of interest.

The on-site analytical system can be broadly depicted as shown in FIG. 1. Sensors 2, 4, 6 are examples of data acquisition devices connectable bi-directionally through communication link 8 which in turn is bi-directionally linked through the central processor 10 to pass information. Information traveling from the sensors 2, 4, 6 through the communication link 8 to the central processor 10 is generally identified as measurement data 12. Information transmitted from the central processor 10 through the communication link 8 to user interfaces (not shown) in the vicinity of one or more sensors 2, 4, 6 is generally identified as measurement results 14. Other information such as announcements, status indicators, user preferences, requests for billing information, system usage information and the like may also be transmitted to and from the central processor 10.

It has been found that utilization of a subset of acquired data from a multichannel instrument, such as a portion or subregion of the available spectrum for a NIR instrument, may generate predicted results that compensate for variations in a wider range of influential factors compared with the results generated from the entire set of multichannel data acquired from a single measurement process for a particular property of interest. A single measurement process may generate a set of multichannel data from the accumulation of multichannel data from individual repetitive runs, and the accumulated data may also be preprocessed. If one or more factors are determined to be influential by experimentation as described above, the instrument response, such as spectral data, may be pre-treated utilizing one or more of several mathematical operations. Pretreatment as used herein encompasses data transformation prior to model prediction. Pretreatment may be used to simplify the data, reduce experimental noise, and eliminate or reduce effects from some secondary variables by mathematical operations such as, but not limited to, filtering the data to reduce its size to one or more smaller subregions of interest and eliminate data from non-interesting or non-beneficial subregions, and applying one or more mathematical transformations such as, but not limited to, weighting, multiplicative scatter correction (MSC), weighted MSC baseline corrections, derivative operations, vector normalization, and standard normal variate and detrend (SNVD).

Pretreatment is performed in connection with the process of developing and using a calibration model, and may be performed before or preferably after transmission of acquired data to the central processor 10. In addition, if the instrument generates a spectrum, pretreatment generally includes filtering a spectrum by eliminating unwanted data at selected wavelengths or wave numbers for a particular property model. Each spectrum forwarded from the sensors 2, 4, 6 preferably retains the entire available spectral region. Later manipulation of the spectrum at the central processor 10 can then utilize various subregions as necessary to generate the predicted result for one or more properties of interest. In some cases, pretreatment is observed to eliminate differences between multichannel data sets that had been present in specified spectral subregions before pretreatment while maintaining sufficient information to permit prediction to a desired statistical level. Pretreatment may also be used with acquired data in forms other than as spectra. When elimination or minimization of differences in the transformed data is observed after pretreatment, the potential influence of these factors on the predicted result is eliminated or effectively reduced by the pretreatment operation. In the case of multichannel data such as spectra, filtering combined with other mathematical transformations of the data in appropriate spectral subregions may be able to compensate for variations in the level of one or more factors by eliminating these factors as variables of the calibration model.

If pretreatment does not eliminate or effectively reduce the spectral differences arising from variations in one or more factors, then the training set is expanded to include spectra corresponding to different levels of those factors, depending on the desired level of precision for the predicted result. In this instance, the properly configured expanded training set will enable a model to be developed that will compensate for variation in the level of the factors by including data in the training set relating to the dependence of the predicted result on the factor. Significantly, it is not necessary to quantify each factor being considered. Rather, a relative or semi-quantitative assessment may be made to ensure that the variation in these factors span the range from hottest to coldest, highest to lowest, and the like. The analyst needs only to include measurements taken at different levels of each factor over an expected range, where the expected range encompasses levels only in that part of the entire possible range of a factor that are expected to occur during actual measurements in the future. For example, if a particular sample was being presented to a detector and a spectrum was generated, the orientation of the sample container at the time of data acquisition by the detector might be considered a potentially influential factor in the final instrument response. Assume that different orientations of the sample container at the time of analysis will create spectral differences which either must be eliminated by pretreatment or must be compensated by extending the training set. To effect compensation, it is not necessary, and occasionally it is not even possible, to determine or establish a quantitative measure of the exact orientation of the sample container at the time when the detector is used to acquire data from the sample. Under the modeling procedure utilized herein, it is only necessary to evaluate the sample container orientation at various random positions which would be expected to span the range of orientations during future measurements.

Generally, the number of levels of a primary or secondary variable which should be selected to span the expected range of variation should correspond at least to two plus the expected complexity of a polynomial approximation of the assumed relationship between observed and predicted values. Thus an assumed, approximately quadratic relationship should have four levels of the factor at a minimum.

As used herein, a property model is an algorithm (or computational procedure) for generating the predicted value of a property of interest for pre-processed data developed from a training set. The property model algorithm is the combination of pretreatment of pre-processed data, followed by evaluation of a calibration model to generate a predicted value from the pretreated, pre-processed data. The property model may be evaluated according to a single mathematical relationship between the instrument response and the property of interest spanning the entire region of the multichannel data, or piecewise from two or more mathematical relationships in various subregions of the multichannel data. In all cases, the algorithm generates a single predicted result that does not depend on knowledge of the particular data acquisition device providing the multichannel data. A global property model is a property model developed from a global training set. Note that a global training set of a property model needs to include data spanning the expected range of only those influential factors that have not been compensated by the pretreatment operations of the property model.

Figure 2:
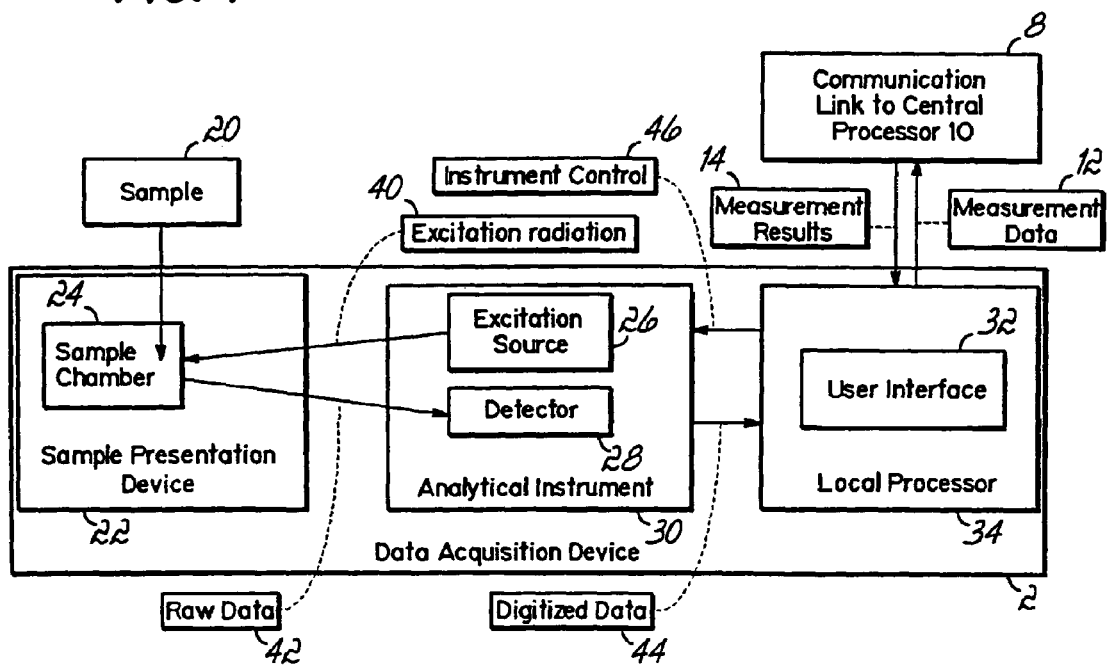
FIG. 2 is a block diagram of components and information transmission within a data acquisition device.

A block diagram showing additional detail of the components and information transmission flow within a data acquisition device is shown in FIG. 2. Sample 20 is deposited into or flows through the sample chamber 24 of the sample presentation device 22. If required by the analytical method, an excitation source 26 is utilized to supply radiation or other form of energy 40 to the sample 20 in the sample chamber 24, the resultant radiation or non-stimulated emission being raw data 42 received by the detector 28. The detector 28 and, if present, the excitation source 26 are located within the analytical instrument 30, which also includes associated components required to generate an instrument response. Information from the analytical instrument 30 is then transferred to the local processor 34 with user interface 32 in the form of digitized data 44 where pre-processing steps may be performed. The user interface 32 passes measurement data 12 to the central processor 10 (not shown) via communication link 8. Measurement results 14 are received from the communication link 8 back to the local processor 34, wherein optionally the resultant information is presented at an output device (not shown) of the user interface 32.

Pre-processing as used herein encompasses the transformation of raw data prior to communication over a communication link 8 using instrumental transduction and computation steps to a form more readily assimilated by the central processor 10. Some pre-processing steps may be performed by the analytical instrument 30 and other pre-processing steps may be performed by the local processor 34. Pre-processing is independent of the process of developing or using a calibration model.

Generally, the generation of predicted values is initiated at the sensor 2 as an example of a data acquisition device. The bi-directionality providable through the communication link 8 can permit the central processor 10 to submit a reminder or other trigger signal to the user interface 32 to initiate the acquisition of data by sending an instrument control signal 46 to the analytical instrument 30. For example, detection of a probable outlier in some measurement results 14 at the central processor 10 can cause the central processor 10 to forward a signal to a user interface 32 of the local processor 34 of a need for additional measurement data 12 on the same sample or a new sample. Alternatively, the scan of a sample may desirably be semi-automated so that additional scans are initiated at regular time periods after an initial scan. This prompt can originate at the user interface 32, or it can originate at the central processor 10 which in turn can forward the prompt to the user interface 32.

Specific combinations of analysis system components have been described. However, it is anticipated that modifications to these combinations will also perform satisfactorily, and are considered to be part of the invention. As an example, the sensor 2 has been described as including a sample presentation device component 22, an analytical instrument component 30 consisting of an excitation source (or other radiation or energy-generating unit) 26 and a detector 28, and a local processor 34 with user interface 32. The sensor 2 initiates data acquisition on the sample 20 in the sample presentation device 22 at the command of the user interface 32, and transmits the acquired measurement data 12 via a communication link 8 to the central processor 10.

It can be appreciated that the sensor 2 does not need to contain the sample presentation device 22, analytical instrument 30, and local processor 34 in a single enclosure for the system to be able to operate. The sample presentation device 22, analytical instrument 30, and local processor 34 can each be stand-alone units if this becomes necessary or desirable, and combinations of these components can be assembled. The desired method operations occurring in the vicinity of the sensor 2 include: data acquisition of a sample 20 of a material, and transmission of an optionally pre-processed form of the acquired data to the central processor 10. Preferably, the method also includes generation of a predicted result using a property model algorithm stored in the central processor 10 and transmission of the measurement results 14 to one or more user interfaces. The sample may be located in the sample chamber 24 of a sample presentation device 22, but some methods of data acquisition may not require this such as when a probe is used to acquire data from a portion of complete living organisms, such as an ear of corn or intact human skin. The data acquisition may be initiated manually by an operator or automatically from a control signal from instrument control 46 transmitted by the user interface 32. The user interface 32 may reside in the local processor 34, but various input and output devices of a user interface may reside in other locations either internal or external to the data acquisition device 2. The local processor 34 may be a stand-alone unit such as a laptop or desktop personal computer or an assembly of components including one or more computer chips, read-only memory, firmware, and the like located within or external to the data acquisition device. Pre-processing of the acquired data from the measurement process is optional. Further, the measurement results 14 are not necessarily transmitted to the user interface 32 of the local processor 34. Measurement results 14 may be forwarded to one or even several locations removed from the operator at the instruction of the customer.

For FT-NIR sensors, the raw detected data is in the form of individual scans of interferogram spectra which may be combined by accumulation of data from repeated individual scans. Instrument operation software, such as the Bruker OPUS product, installed on the local processor 34 of the sensor 2 averages the acquired multi-scan spectra in the interferogram mode, converts this average interferogram to a single-channel spectrum by fast Fourier Transform, and converts the single-channel spectrum to an absorbance spectrum according to the equation:

$$\text{absorbance spectrum} = -\log(\text{single-channel spectrum}/\text{background spectrum}).$$

This calculation removes eccentricities in the sample spectrum attributable to the background spectrum specific to that sensor 2. It is noted that a "single-channel" spectrum is an alternative representation of a spectrum that contains a plurality of data values and, thus, a single-channel spectrum is still a multichannel data set. A background spectrum is acquired by operating the instrument 30 either with no sample in the sample chamber 24 or with a data acquisition probe in direct contact with a reference material such as the reflective surface of a mirror or a spectralon composed of polytetrafluoroethylene. The acquired background spectrum provides a digitized spectrum 44 which is then used to pre-process spectral data according to the above equation. A digitized background spectrum is preferably stored in the local processor 34 of each sensor 2, 4, 6 although other storage locations may be used. Thus, a single background spectrum is generated and stored for each sensor 2, 4, 6 for use in generating a plurality of predicted results from one or more property models in the future. The single background spectrum is generally acquired from a single data acquisition device, but may be generated from an accumulation of background spectra acquired from two or more data acquisition devices. The background spectrum is generally stored in the local processor 34, but may be stored in the central processor 10 or another location remote from the data acquisition device that can be connected to the data acquisition device by a communication link 8.

A material as used herein encompasses any object for which it is desired to generate a value of a property. The value may be a measurement for which a quantitative result is desired. The value may alternatively be a qualitative one, indicating only the presence or absence of a component. The material may be in any physical form, i.e., gaseous, liquid, solid, or mixed phases, and may encompass both discrete units or components thereof, such as either a whole oilseed or the oil expressed from the seed, and may consist of mixtures of different substances, such as foreign matter in a sample of whole grain. In addition, for certain types of analyses the term may encompass living plant or animal matter, such as human tissue or fluids. The sensor 2 may optionally include an excitation source 26, a sample handling device 22 to present the sample 20 to the detector 28, and associated electronics to convert the detector output into a digitized format 44. A wide range of sensors of various types, herein called sensor-types, can be used to acquire data for subsequent analysis, including but not limited to those for NIR, mid-IR, Raman, UV, visible, and NMR spectroscopy, liquid or gas chromatography, or mass spectrometry. Other spectroscopic and non-spectroscopic types of sensors may also be used.

If sensors of different types are used for on-site analysis, sensor-type-specific property models are required. A sensor-type is a type of instrumentation that acquires multichannel data based on a specific analytical method, such as Fourier-Transform NIR or gas chromatography. It is preferred that different instruments within a single sensor-type are manufactured according to well defined design specifications as is done for specific models of an instrument, usually by a single manufacturer, such as the MATRIX Model F FT-NIR spectrometer manufactured by Bruker Optics.

In one embodiment of the present invention, the detector information acquired on a sample 20 may optionally be both pre-processed and converted into a digital format to facilitate rapid communication with the central processor 10 and subsequent data processing. While another embodiment could utilize the transmission of unprocessed multichannel data, the preferred embodiment is advantageous in that digitization and averaging occur prior to transmission of data to the central processor 10.

The user interface 32 may be installed in an apparatus physically attached to, or integrated with, the sensor 2, but this is not required. Generally, an output device of the user interface 32 is located in the vicinity of the sensor 2 because the resultant information will typically be desired at the location where the data on the particular material is acquired. For example, in the case of the characterization of a property of interest for oilseeds, the measurement data 12 may be acquired at a storage silo, or near a transport truck, and the measurement results 14 are returned to the operator at these locations. Alternatively, the measurement results 14 may be disclosed at an office near the storage silo with optional ancillary equipment such as a printer to generate a written record of the generated result. As a further alternative, however, the measurement results 14 may be disclosed at an administrative or processing location of the customer which is geographically far removed from the storage silo location where the measurement data 12 was acquired. It is possible, though not preferred, to communicate with the operator or other recipient of the result in the vicinity of the sensor 2 by a communication link independent from that of the link 8 connecting the sensor 2 and the central processor 10. Thus, measurement results 14 generated by the central processor 10 may be communicated to the operator or another designated party in an indirect manner such as telephone or facsimile transmission even where the sensor 2 and central processor 10 are linked via the Internet.

The hardware of the system architecture is characterized by an unusual master-slave relationship established between the one or more sensors 2, 4, 6 and the central processor 10. Since data acquisition is initiated at the sensors 2, 4, 6 the central processor 10 becomes a slave to the sensors 2, 4, 6 in the field. The sensors 2, 4, 6 do not operate as self-contained analyzers, but are dependent on the central processor 10 for data analysis. Thus, the sensors 2, 4, 6 are dumb masters and the central processor 10 is a smart slave in a many-to-one relationship.

In another embodiment of the system architecture, the central processor 10 sends one or more property models (as, for example, an information packet of parameters sufficient to define one or more property model algorithms) to at least one sensor, e.g., 4, over the communication link 8, at various intervals as desired to enable at least sensor 4 to perform local computations of measurement results. In this mode of operation, the sensor 4 is a self-contained analyzer, although all sensors 2, 4, 6 still use the same property model algorithm for a particular property of interest. Since the algorithm does not contain any instrument-specific parameters, this embodiment is different from calibration transfer and instrument standardization methods which attempt to compensate for instrument variance by developing and transferring instrument-specific calibration models for use by specific instruments. This embodiment is useful as an alternative strategy for situations in which it may not be possible or desirable to use a communication link 8 for real-time model calculations.

This alternative embodiment can be used as a backup strategy to enable measurements to be performed when interruptions in the communication link 8 have existed or may be expected. This embodiment can also be used for measurements in remote locations where it is impossible, difficult, expensive, or inconvenient to use a communication link 8 to the central processor 10. This mode of operation may enable alternative productive analysis methods as electronic components get smaller and faster, particularly for situations where very rapid response times are desired or when it is desirable to avoid sending data or results over a communication network 8. Presently, this embodiment is less preferred because an update to the property model is not automatically available to the sensor 4. Nonetheless, this embodiment retains the advantage of a single property model algorithm at a point in time from which predictions are made.

In another embodiment, the current version of the property model algorithm is transmitted to the sensor 4 immediately prior to the data acquisition step of each measurement process to ensure that the measurement results are computed from the most recent update to the property model. In these alternative embodiments, the measurement data and locally computed measurement results may be transmitted to the central processor 10 for storage and distribution at a later time.

The user interface 32 located near the sensor 2 can provide a selectable menu of properties of interest that are available at the central processor 10. Prior to each measurement, for example, the central processor 10 can transmit the current list of available properties of interest to the sensor 2. Then, the user will always access from the updated selectable menu displayed at sensor 2 the most current list of available properties, and thereby use the most current revision to all property models without needing to manually install software updates to replace, change, add, or delete models as would need to be done if the models were stored in computing devices individually connected to each sensor 2.

Where multiple sensors 2, 4, 6 may be used, the sensors 2, 4, 6 may be located at a variety of distances from the central processor 10 as needed to provide for on-site analysis. The sensors 2, 4, 6 are typically remote or distant from the central processor 10, where remote refers only to the existence of a physical separation between the sensors 2, 4, 6 and the central processor 10. A remote sensor 2, 4, or 6 does not in any way require that the on-site location is isolated geographically or technologically. Indeed, one or more remote sensors 2, 4, 6 can be located in a central laboratory in a large metropolitan area as well as at isolated sites far removed from population centers.

One example of a communication link 8 between sensor 2 and central processor 10 which may be utilized is the Internet. In operation using one or more NIR spectrometers as analytical instruments 30, the on-site analysis system utilizes a user interface 32 running in a browser installed in the local processor 34 which performs a security logon function, presents the operator with input fields to identify the sample being analyzed, and prompts the loading of the sample 20 into the sample presentation device 22. The security logon process requires both a password known only to the operator and a sensor 2 identified electronically by a serial number. This logon therefore requires both a specified piece of hardware and an independent password.

The user interface 32 then presents the operator with input fields to identify the sample 20 being analyzed. Examples of descriptive data collected about the sample 20, herein called sample identification data, include but are not limited to the type of sample being tested, the location where the sample was collected, and a unique identity of the sample. The operator is then prompted to load the sample 20 into the specific instrument sample presentation device 22 and to start the collection of measurement information from the multichannel analytical instrument 30, this information herein called multichannel data. In the case of a near-infrared spectrometer, the multichannel data collected is pre-processed spectral data. The measurement data 12 comprises the sample identification data and the multichannel data, which is sent over the Internet 8 to the central processor 10 for analysis. The information packet of measurement data 12 is processed through routers and firewalls where it is received by a standard web server such as the Microsoft® Internet Information Server.

The information packet is accepted at the central processor 10 by a web server which initially processes the information and forwards this information to a queuing system. The queuing system accepts near-simultaneous transmissions from multiple sensors and queues the submissions to be processed in FIFO (first in first out) order by the central processor.

The analysis engine of the central processor 10 accepts the information packet of measurement data 12 sent by the queuing system and opens the packet to find both the multichannel data to be analyzed and sufficient descriptive information entered by the operator in the sample identification data to select the proper property model to be used for analysis. After calculating the predicted results through the proper property model, the measurement results 14 are then passed back to the queuing system for communication over the Internet to the operator at the user interface 32, or optionally to another user interface at a location in the same vicinity, a field office of the customer, or another alternate location. The measurement data 12 and the processed measurement results 14 are preferably stored in a database, called the data repository, where they may be retrieved for later reference if desired.

The communication link 8 used in transmitting data and results, briefly discussed above, is considered in more detail. The communication link 8 may encompass any device or communication system which can provide for information transfer within acceptable limits for signal degradation and transmission speed. For example as discussed above, the on-site location sensor 2 and central processor 10 may be connected to one another via a global, public network such as the Internet. Alternatively, a local or global private network or combination of public and private communication links may be employed. Communication between the sensor 2 and central processor 10 can be enabled by a user interface 32 consisting of an emulated instrument panel or graphical user interface which runs on a standard Internet browser executing in the local processor 34. The local software component of the instrument panel is a set of HTML-based code that includes additional code such as Java® as an example of client-based software that communicates with the instrument 30. This set of software code is configured to be able to communicate with instruments from multiple manufacturers, or multiple instrument designs from a single manufacturer. Thus, though the sensor 2 may include a near-infrared device, the host-based software component of the instrument panel executing in the central processor 10 is designed to accept input from other spectroscopic and non-spectroscopic devices. The user interface 32, running within a standard Internet browser, is an interactive software application that can be run from any platform that can host a browser, including but not limited to desktop personal computers and laptops, as well as various wireless devices.

Within a sensor 2, the data acquisition portion of the system is generally the detector 28 of the analytical instrument 30 and the user interface 32. Note that the local processor 34 may be a separate, stand-alone device or may be integrated into the device 2. In either case, the sensor 2 is generally considered to comprise at least the detector component 28 of the analytical instrument 30 and the local processor 34 that runs the user interface 32. The user interface 32 contains the entry point to the system sign-on, input fields for customer authentication and system usage authorization, and other miscellaneous interfaces such as system status, announcements, access to authorized portions of information in a data storage unit to provide additional information reporting capability, and help text to provide users with specific operating instructions. The user interface 32 running on the browser of the local processor 34 of the sensor 2 connects to an analytical instrument 30 such as a NIR detector, in which case the user interface 32 controls data acquisition from instrument 30 and the transmittal of that data over a communication link 8, i.e., the Internet in this instance, to the central processor 10.

Figure 3:
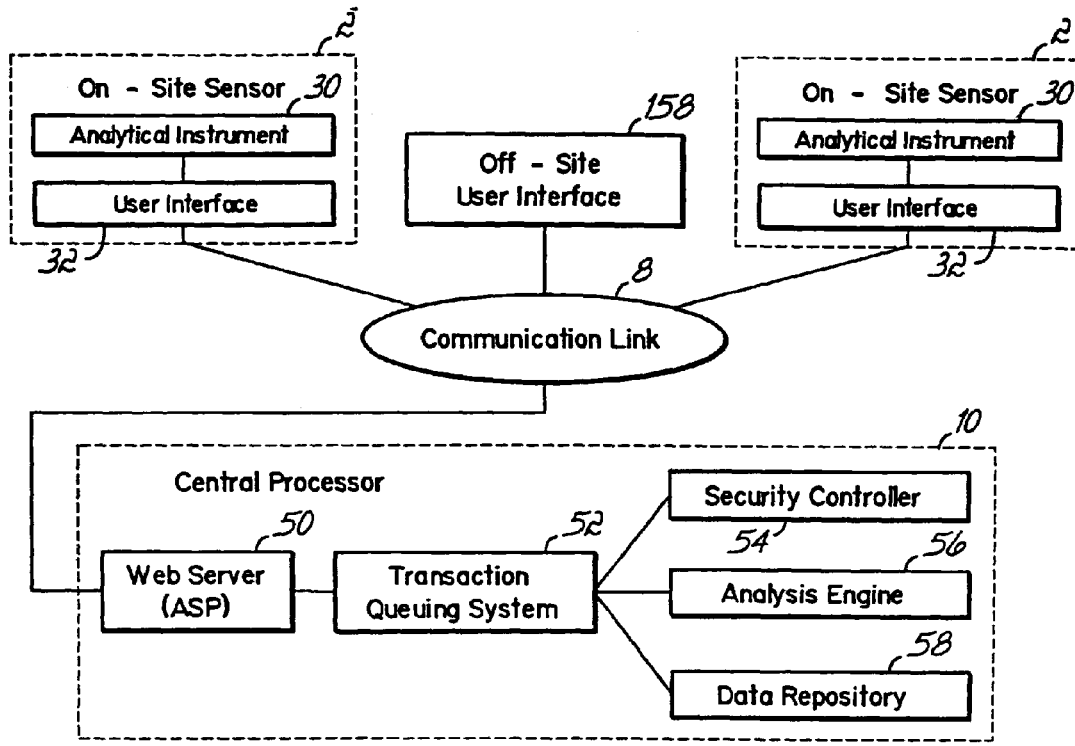
FIG. 3 is a block diagram of system architecture.

The system architecture based on use of the Internet as the communication link is shown in FIG. 3. This diagram shows software components of the hardware illustrated in FIG. 1. Data acquisition by the analytical instrument 30 is initiated by the user interface 32. Connection between the user interface 32 and the central processor 10 is provided by the ASP (active server page) 50 running on a web server and controlling the communications. The central processor 10 is comprised of the ASP 50, a transaction queuing system 52 that provides scalability for transaction volume, the security controller 54 for authenticating and granting processing rights to incoming transactions, the analysis engine 56 which requests parameters of property models from the data repository 58, performs pretreatment operations, and computes the predicted value for each property requested, and the data repository 58 which stores transaction input information, or measurement data 12, and transaction output information, or measurement results 14, for providing potential added informational value to the customer. The data repository 58 may be a SQL database, although other types of databases may be used. It is preferred that the database be relational. Integrated into the central processor 10 is a security architecture that protects proprietary rights to the various data types stored in the data repository 58 of the central processor 10 and delivers information only to those properly authorized to receive the information.

The queuing system 52 forwards the measurement data 12 to the analysis engine 56, upon which the analysis engine 56 requests and obtains the parameters defining one or more property models from the data repository 58 as specified by the descriptive information in the measurement data packet 12. The analysis engine 56 performs calculations comprising pretreatment, property prediction, and associated statistical measures of the property prediction such as the Mahalanobis distance. The queuing system 52 requests that the data repository 58 accept the measurement results 14 for storage and requests that the web server 50 accept the returned measurement results 14 for transmission to the user interface 32, to one or more other user interfaces, or both.

To enable multiple sensors 2 to communicate with the central processor 10, the transaction queuing system 52 of the central processor 10 performs a function of accepting a high volume of near-simultaneous communications from multiple locations over the communication link 8 and controlling the communication flow to the analysis engine 56 and relational database 58. The queuing system 52 is described in detail in a separate patent application, entitled "Extensible Modular Communication Executive With Active Message Queue And Intelligent Message Pre-Validation, by James Thomas Kent, et al., filed on even date herewith, Ser. No. 60/307,347, which is incorporated herein by reference.

In preparing to conduct an analysis of a material at a variety of remote locations, it is necessary to generate a calibration model which addresses all factors that may significantly influence the measured properties. As noted above, such modelable factors occur in the following areas: the material to be analyzed; the instrument; the environment; and the material presentation. Operator-to-operator variations in the measurement process are generally captured by influential factors associated with the material presentation. The desired reliability of the analysis dictates the number of factors within each of these areas which should be anticipated and modeled.

The development of calibration models is generally done using one or more sensors that are not necessarily connected to the central processor 10. Furthermore, the calibration models are developed and validated using chemometric software such as OPUS Quant-2 and (dent on a computer that may be different from the local processor 34 of a sensor. Validated calibration models are loaded into the data repository 58 of the central processor 10 to enable on-site measurements by remote sensors 2. In the course of generating an instrument response relating to the property of interest of a sample 20 of a material, using one or more sensors not necessarily connected to the central processor, a univariate calibration would be used if the instrument response was dependent only on the property of interest. Unfortunately, it is rarely possible to obtain ideal measurements of a property where the measurement process is selective for just the property of interest. Realistically, particularly to build models suitable for use by non-specialists, additional variables must be taken into account to reflect the realities of generating a calibration model where variations may be expected to occur in the instrument, the environment and in the sample presentation, in addition to variations between and within samples of material. In addition to random measurement noise, the data may be affected by chemical and physical interferences. Chemical interferences alter the instrument response due to the presence of chemical impurities in the material being tested, inhomogeneities in the distribution of chemicals in a mixture, and the like. Physical interferences alter the instrument response due to, for example, light scattering effects and instrument variances.

Figure 4:
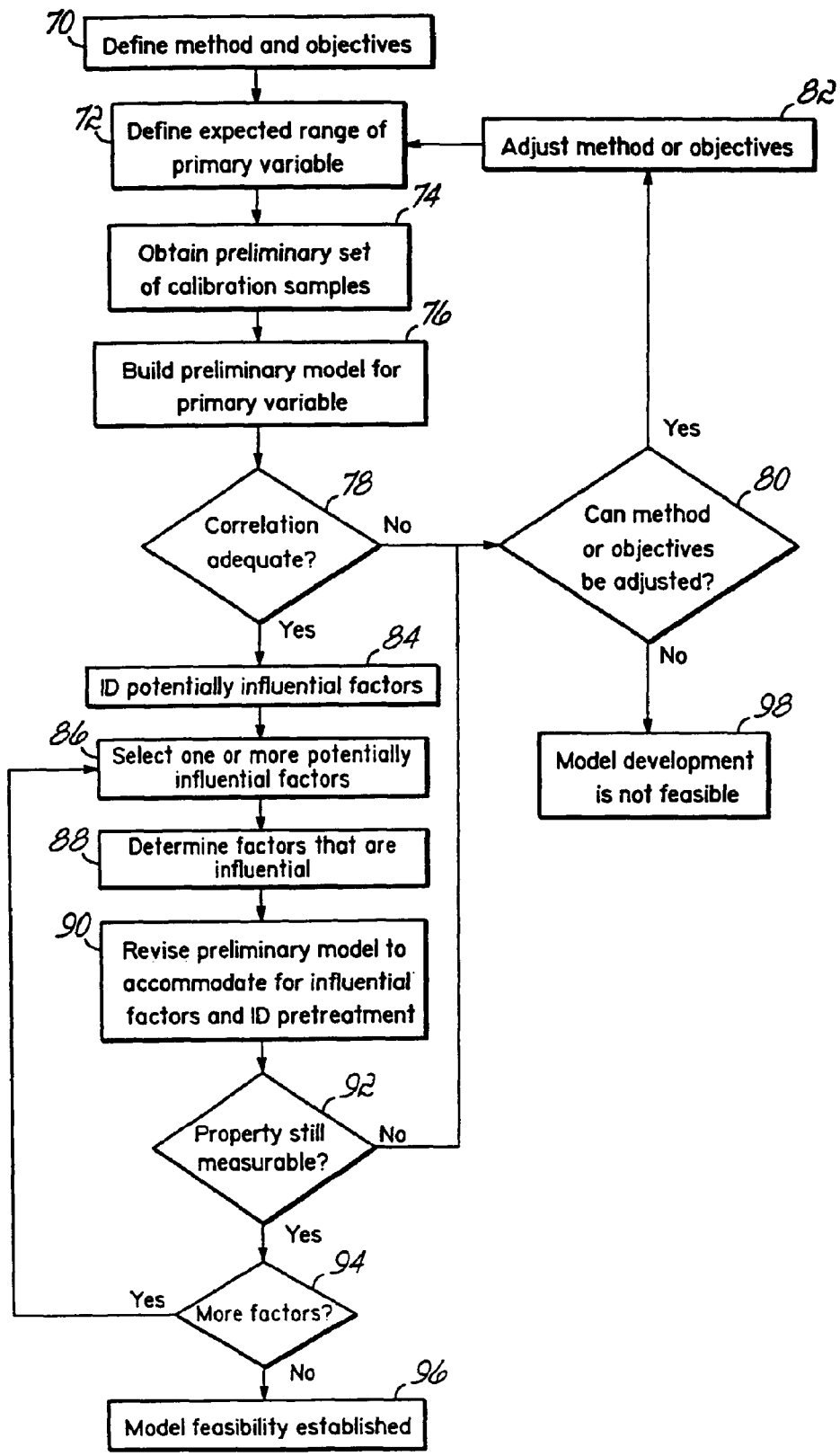
FIG. 4 is a flowchart to establish model feasibility.

A flowchart for establishing the feasibility of developing a property model is provided in FIG. 4. This process is used to determine if a selected measurement method using a specific sensor-type is capable of being used to predict a property of interest over a desired range of that property. Initially, as shown in block 70, the method and objectives are defined. The method of block 70 refers to the analytical method, such as FT-NIR or gas chromatography, and includes specifying the analytical instrument, such as a Bruker MATRIX Model F FT-NIR spectrometer, and the sample presentation, such as 0.5 to 1.5 mL of liquid contained in a metal closure cap with an 18 mm diameter. The objectives of block 70 define expectations for a property model. These objectives identify the property of interest, the desired precision for predictions of the property of interest, the calibration set upon which a feasibility assessment will be made, and the expected ranges of the secondary variables related to the samples and measurement conditions as specified by the customer and as recommended by the analyst responsible for model development. Then, as shown in block 72, the expected range of the primary variable is defined from the objectives of block 70, and a preliminary set of calibration samples is obtained that span the expected range of the primary variable as shown in block 74. The number of samples in this preliminary calibration set typically ranges from about 5 to about 50.

Next, a preliminary model is built for the primary variable, shown in block 76. At this initial stage of model development, the potentially influential factors are not intentionally varied. Measurements at this stage are taken under ambient conditions with a single instrument as defined by the method and objectives 70. The training set used in block 76 may be generated by taking a single measurement of each sample in the calibration set of block 74 or the training set may be expanded to include repeated measurements of some or all of the calibration set of block 74. Each instrument response in a training set may be generated from the multichannel data acquired during a single multichannel measurement or during two or more multichannel measurements. In some cases, it may be desirable to combine or accumulate the multichannel data acquired from two or more multichannel measurements of different samples, different measurement conditions, or both, into a single set of multichannel data comprising the instrument response.

Using the symbol "y" to denote the property of interest, the following definitions apply in further considering the calibration process:

$y_{obs(i)}$=the $i^{th}$ observed or known value of property y. This is also called the true or expected value.

$y_{pred(i)}$=the $i^{th}$ predicted value of property y. This is also known as the measured value.

$Res_i = y_{pred(i)} - y_{obs(i)}$, and is known as the $i^{th}$ residual or deviation between predicted and observed results.

M=the number of predicted values in the instrument response set.

$$SSE = \sum_{i=1}^{M} (Res_i)^2$$

= sum of squared errors.

RMSECV=square root of SSE/M for the training set
=root mean square error of cross-validation wherein the calibration model is generated with a training set and predictions from this model were made using the same training set.
RMSEIR=Square root of SSE/M for the instrument-response set
=root mean square error of predictions from the instrument-response set.
RMSEP=square root of SSE/M for the validation set
=root mean square error of prediction wherein the calibration model is generated with a training set and predictions were made on a validation set.
$r^2$=coefficient of determination; or square of the correlation coefficient (r), which provides a measure of the degree of correlation between $y_{obs(i)}$ and $y_{pred(i)}$.
$R^2=100\, r^2$ Using commercially available chemometric modeling software such as HOVAL software (such as Version 1.6, 1992), AIRS software (such as Version 1.54, 1999) or Bruker OPUS-NT Quant-2 software (such as Version 3.01, 2000), the initial version of the calibration model is generated, as indicated in block 76, from a training set in which the primary variable spans the anticipated range over which this variable is expected to vary during actual measurements in the future. The coefficient of determination, $r^2$, is used to determine whether the correlation is adequate to measure the property, as shown in block 78. Generally, if $r^2$ is less than about 0.6, or equivalently if $R^2$ is less than about 60, it will be necessary to consider adjusting the method or objectives as shown in block 80. During this adjustment step, a procedure for sample preparation or impurity reduction may be defined or refined, the preliminary calibration set may be modified, or a different method may be selected. If the method or objectives can be altered, then the new definitions are adopted as shown in block 82 and, according to the expected range of block 72 and using a preliminary set of calibration samples from block 74, another preliminary model is developed in block 76. The coefficient of determination, $r^2$, of the training set of block 76 is used to decide whether the property of interest is measurable according to the method and objectives of block 82. As long as the property is not measurable (block 78) and the method or objectives can be adjusted (block 80), blocks 82, 72, 74, 76, and 78 are repeated. If the method or objectives cannot be adjusted (block 80), then model development is not feasible (block 98) in accordance with the definitions of block 70 as adjusted by block 82.

If it is determined that the correlation is adequate (block 78), specifically if $r^2$ is greater than about 0.6, although smaller or larger values can be used depending on specific objectives in blocks 70 and 82, it is considered feasible to begin testing for potentially influential factors. The next step is to identify the types and expected ranges of the potentially influential factors as shown in block 84. Next, as shown in block 86, one or more potentially influential factors are selected for experimental investigation. In block 88 experimentation is conducted to determine whether the factors are indeed influential using a small validation set. In block 90 the preliminary model is revised to compensate for secondary variables that have been experimentally demonstrated to be influential factors and appropriate methods of pretreatment are identified when possible. A decision is then made in block 92 to determine if the property of interest is still measurable in the presence of variations in the secondary variables. The measurability of block 92 is determined by comparing the RMSEP of the validation set of block 88 with the desired precision specified in the objectives of blocks 70 and 82. The property is considered measurable in block 88 if the RMSEP is less than or approximately equal to the desired precision value. If not measurable, the method or objectives for developing the calibration model are adjusted as in block 82, if possible (block 80), and the process is repeated beginning again with block 72. If, in block 92, the property of interest is still measurable to the limit of desired precision specified in the objectives of blocks 70 and 82, and if there are more factors in block 94 that have not been investigated experimentally, then the feasibility process returns to block 86 where one or more additional, potentially influential factors are selected, experimentation is conducted in block 88 to determine those additional factors that are influential, the model is revised, methods of data pretreatment are identified in block 90, and a determination is made in block 92 whether the property of interest is still measurable to the limit of desired precision. The process of selecting potential factors (block 86), experimentally determining influential factors (block 88), revising the model and identifying pretreatment methods (block 90), and determining if the property is still measurable to the limit of desired precision (block 92) is repeated until there are no more potentially influential factors to consider in block 94. If the property of interest is ultimately determined to be measurable (block 92) in the presence of variations in the secondary variables identified in the objectives of block 70 as adjusted by block 82, and if there are no more potentially influential factors to consider in block 94, then model feasibility is established as shown in block 96.

The process for identifying influential factors and revising the calibration model to accommodate secondary variables that are demonstrated to be influential factors experimentally is considered in detail below.

To determine if a factor has an influence on the predicted result of a model (block 88), a small validation set is developed which includes measurements at some different levels of the potentially influential factor. Specifically, one or more samples with $y_{obs(i)}$ for the property of interest in the presence of a range of values for the secondary variable being considered are measured with the instrument 30 (FIG. 3), and the $i^{th}$ instrument response is used to generate $y_{pred(i)}$ using a previously generated calibration model. The RMSEP of this validation set is then calculated using this previously generated calibration model to serve as an estimate of the level of precision of the property model in the presence of variations in secondary variables. During this feasibility assessment process, it may be sufficient to use a validation set containing a single pair of observed and predicted values, and use the absolute value of the difference between these values as a single-point estimate of RMSEP. It can be appreciated that different factors will have different degrees of influence on the property of interest values being predicted by the property model. In some applications the desired level of precision as specified in the objectives of blocks 70 and 82 will be very high, and factors having even a very minor influence will be considered in generating the model. In other instances where the desired level of precision is lower, the factors having low levels of influence may be ignored, with consequent losses in precision.

One method of quantifying an acceptable or desired level of precision involves consideration of a confidence interval for predictions of a property of interest. A confidence interval is a range of predicted values that includes the true average value of the property of interest a specified percentage of the time. Thus, for example, if the average value of a property is 3.5±0.6 at the 95% confidence level, then 95% of the time the predicted value of the property is expected be in the interval from 2.9 to 4.1. Since the average value of a number of measurements tends to follow a Gaussian distribution, the confidence interval can be expressed as an average value plus or minus a multiplicative factor times the standard deviation of the average value, where the multiplicative factor can be obtained from statistical tables that relate this factor to the area under a standard Gaussian distribution curve. For example, when the multiplicative factor has a value of 1, 2 or 3, the corresponding area under the standard Gaussian distribution is about 68%, 95% or 97.7%, respectively. So, if it is desired to have about 95% of the future predicted values fall in the interval from +0.6 to −0.6 of the true average value of a property, then the multiplicative factor would be 2 and the standard deviation of the average value should be 0.3, which is one-half of the desired precision of 0.6. The standard deviation of the average value can be estimated, for example, by the RMSEP of a validation set. As a result, the desired precision can be expressed as a multiplicative factor times RMSEP. Thus, a desired precision of ±0.6 at the 95% confidence level is equivalent to specifying that the RMSEP should be less than or equal to 0.3. This is equivalent to specifying the desired precision of ±0.6 as 2 times an RMSEP of 0.3 at the 95% confidence level. This is also equivalent to specifying the limit of desired precision as a RMSEP of 0.3 at the 95% confidence level.

In general, varying the level of a potentially influential factor produces instrument responses for the validation set that, after pretreatment and evaluation by the calibration model, predict values of the property that differ numerically from the corresponding known values. The numerical differences may or may not be statistically significant. If the RMSEP value computed from these numerical differences is less than or approximately equal to the value used to specify the limit of desired precision, the numerical differences are not statistically significant to that limit of desired precision. Alternatively, if the RMSEP value is greater than the limit of desired precision, the numerical differences are considered to be statistically significant. In those cases when the numerical differences are not statistically significant as measured by RMSEP, the results predicted from the property model are considered to be statistically equivalent. Thus, when varying the level of a potentially influential factor to generate a validation set in block 88 produces statistically equivalent results, the factor is considered to be non-influential for that property model to within the limit of desired precision. Alternatively, if the numerical differences as measured by RMSEP are statistically significant, then the factor is influential and the property model needs to be revised in block 90. If the revised model generated in block 90 then produces results that are not statistically different from the known values, the property is still measurable to the desired precision in block 92.

Acceptable levels of precision as measured by RMSEP fall within the range of values defined by the particular client acquiring the predicted results as established in blocks 70 and 82. If acceptable precision is obtained in the experimentation of block 88, predictions can be made with that calibration model independent of changes in the secondary variable, the associated factor is considered to be non-influential for that model, and the model does not need to be revised in block 90. The RMSEP is one calculated value which is used to evaluate the level of influence of a factor. A greater increase in RMSEP from a validation set relative to the RMSECV of a training set indicates a greater level of influence. If the RMSEP from the validation set of block 88 does not meet the objectives of blocks 70 and 82, then the model will need to be revised in block 90. Again, the ultimate desired precision of the model will determine if the influence due to a particular factor will require compensation in the development of the model.

It can be appreciated that a factor which is ultimately determined to be influential in connection with predicting one property of interest of a sample may not influence the prediction of another property of interest. Thus, the determination of whether a factor is influential is dependent on the specific circumstances of the acquisition of data. Furthermore, it is not required to quantify each of the secondary variables. Thus, it is not necessary to determine the actual humidity inside the measuring instrument, or determine the actual age of the excitation source, such as a light used in a near-infrared spectrometer, as long as data points spanning the expected ranges of humidities and light ages are included in the training set or the validation set, unless pretreatment eliminates such factors. Quantifiable values for the secondary variables are not required but may be recorded if the description of a value is desired.

The model considers a range of variables wherein the range is defined by the type of analysis being made and the expected range of measurement conditions for the particular property of interest. The primary variable is directed to the particular property of interest. The secondary variables may include but are not limited to the following directed to secondary material characteristics of the sample: impurities or other components in the material to be tested; the form of the sample, i.e., solid, liquid, gas or mixed phases; the presence of turbulence in a gaseous or liquid sample; the presence of multiple phases in a sample, such as gas in a liquid, liquid in a solid, hydrophilic and lipophilic liquids combined as an emulsion, or solids dispersed in a liquid or a gas; the particle size distribution of a solid sample; the presence of inhomogeneities in a sample regardless of form; the distribution of shapes of solid particles; the degree of compaction of a sample of solid particles; the tendency of a sample to alter its composition and structure during the measurement process, such as by the formation of hydrates or oxides in a humid air environment; the tendency of a sample or components thereof to evaporate, sublime or decompose; and the tendency of one or more components of a liquid or gaseous sample to settle, or stratify.

The secondary variables also may include but are not limited to the following directed to the instrument: changes in one or more mechanical, optical or electrical components which would impact signal detection or conversion of the input signal into a format suitable for subsequent processing. These changes include inter-relationships between components such as positional and orientation relationships, and electrical, optical or mechanical interactions in the assembly of the components. For many of the instrument components the effect of age is negligible or unlikely to affect the instrument response, such as regarding the instrument housing or the overload protection circuitry. Other components will create a more dramatic and definite effect on the sample output signal over time, such as a light source in a spectrometer.

The secondary variables further may include but are not limited to the following directed to the environment and the sample presentation: temperature of the sample; temperature, humidity and atmospheric pressure of the environment in the vicinity of the test instrument; humidity inside the test instrument; airflow in the vicinity of the test instrument; background radiation in the vicinity of the test instrument; the dimensions of the sample container or detector chamber as they affect the pathlength of the excitation beam through the sample; the distance between sample and detector; the presentation speed or flow of the sample relative to the detector and relative to the data acquisition rate of the detector; and the amount of sample presented to the detector, expressed as volume, weight, surface area, pressure, and the like.

Each of the above variables are considered as potentially influential factors. The actual significance of a secondary variable is determined during the process of developing the calibration model for a particular property of interest.

Figure 5:
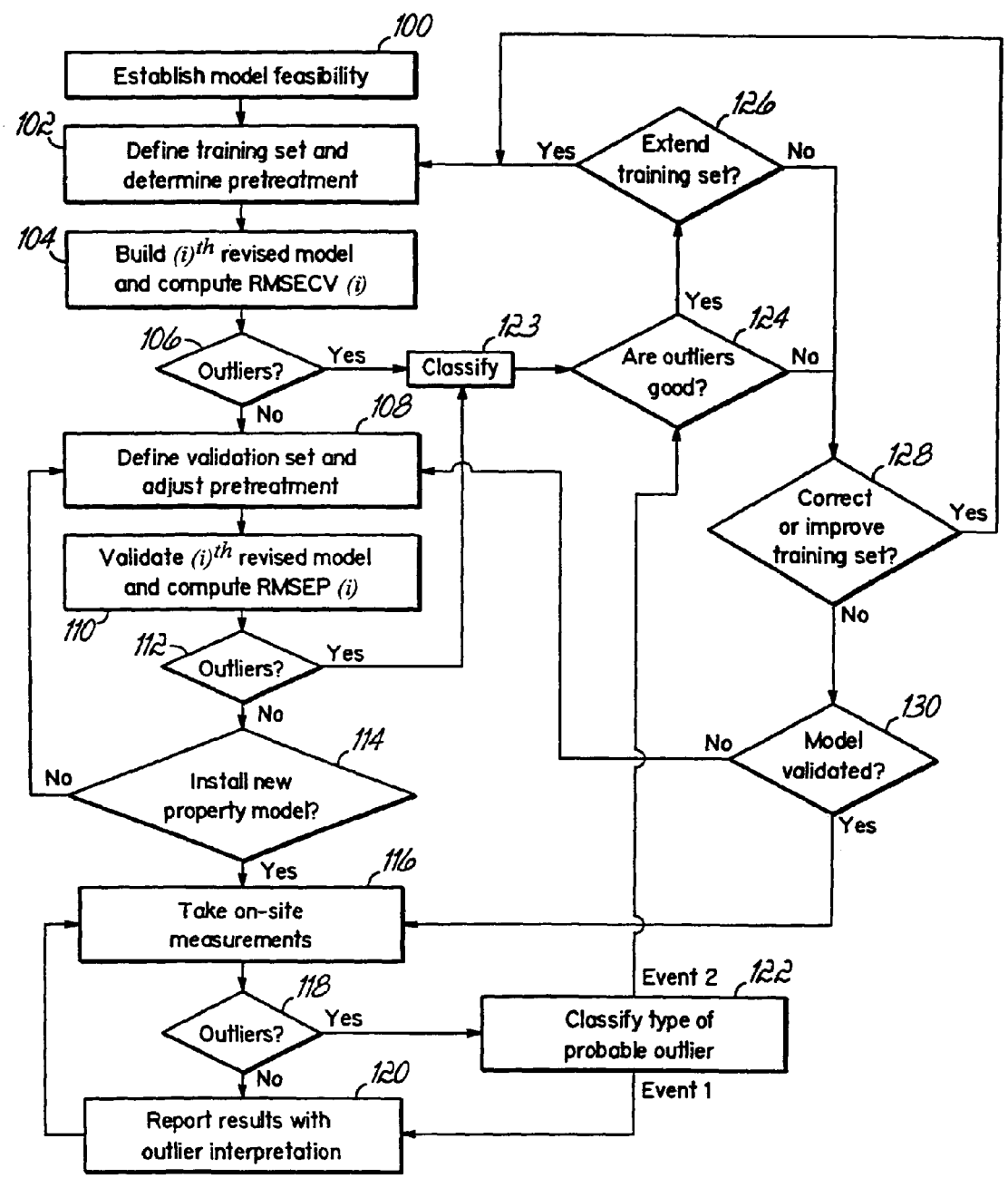
FIG. 5 is a flowchart of model development and use.

In connection with developing and using a calibration model, reference is made to the flowchart in FIG. 5. Initially, the feasibility of establishing a calibration model is determined in block 100, which consists of at least blocks 70, 72, 74, 76, and 78, as well as blocks 80 and 82 as required, of FIG. 4. In addition, after the property is determined to be measurable in block 78, one or more potentially influential factors is investigated experimentally as indicated in blocks 84, 86 and 88. Revisions to the preliminary model in block 90 can be undertaken either by making several stepwise adjustments for one or a small number of factors determined to be influential in block 88, or by adjusting for all experimentally determined influential factors at one time. During these feasibility steps, essential characteristics are identified for the training set along with preliminary methods of pretreatment. The essential characteristics of a training set include the range of material characteristics that must be represented by samples in the calibration set, and the levels of influential factors that must be represented by instrument responses generated from the calibration set. The preliminary methods of pretreatment are those mathematical operations that must be used on optionally pre-processed instrument responses to compensate for influential factors that are not necessarily represented by instrument responses in the training set.

Considering this information, in block 102 of FIG. 5, a training set is defined and a method of pretreatment is determined in order to begin the process of revising the preliminary model. Then, in block 104 the $i^{th}$ revised model is built and RMSECV(i) is computed, where i equals one for the first revision and i is incremented by one for each subsequent revision. In block 106, if no outliers are found in the training set, then a validation set is defined and the methods of pretreatment are adjusted as shown in block 108. The $i^{th}$ revised model is then validated and RMSEP(i) is calculated in block 110. Next, if outliers are not found in the validation set using this model as indicated at block 112, then a decision is made at block 114 whether to install the new property model in the data repository (block 58, FIG. 3) of the central processor 10. The outcome of block 114 depends on whether the model has been constructed to compensate for an effectively comprehensive set of influential factors. If no, then the process returns to block 108, the validation set is defined to include variations of one or more additional influential factors, the pretreatment is adjusted, and the process continues at block 110. If yes, then the new property model is installed, and on-site measurements can be taken using the new property model as indicated at block 116.

If probable outliers are found in the training set at block 106 or the validation set at block 112, then the outliers are classified at block 123 and a determination is made if the probable outliers are good outliers at block 124. If any detected outliers are good, then a decision is made to determine whether to extend the training set at block 126. If yes, then the process returns to defining which good outliers will be added to the training set and an appropriate method of pretreatment is determined for this training set, as indicated in block 102. After building the next, or $i^{th}$, revised model and computing RMSECV(i) in block 104, the process continues forward with block 106. If the decision is made not to extend the training set in block 126, or if the probable outlier is not good at block 124, then a decision is made whether to correct or improve the training set in block 128. If erroneous data are found in the training set or the validation set, or if improved known values become available, then the training set is re-defined with the improved or corrected data and the process resumes at block 102. If the decision is made not to extend the training set in block 126, and if there are no corrections or improvements to be made in block 128, then if the current, $i^{th}$ revised model has not been validated in block 130, the process resumes at block 108. The validation steps in blocks 108, 110, and 112 are repeated until no outliers are found in block 112, and a decision is made at block 114 whether to install the new property model. Alternatively, if the decision is made not to extend the training set in block 126, and if there are no corrections or improvements to be made in block 128, and if the current, $i^{th}$ revised model has been validated in blocks 108, 110, and 112, and if it is decided to install the new property model in block 114, the next step is to proceed with taking on-site measurements at block 116.

While taking on-site measurements, block 116, as well as while building at block 104 and validating at block 110 a property model, the Mahalanobis distance, MAH, is computed for each predicted value. If the MAH is greater than the threshold value for good outliers of that property model, the predicted value is considered to be a probable outlier. Thus, the determination of whether a predicted value of an on-site measurement at block 116 is a probable outlier at block 118 leads to two possible outcomes. If yes, then the predicted result is probably invalid and MAH is used to classify the prediction as a particular type of probable outlier at block 122. If no, then the prediction is presumably valid at block 120. In either case, the results are reported. If a probable outlier is detected, the results include a descriptive interpretation of the type of probable outlier at block 120. The analysis system is then ready to process the next on-site measurement at block 116.

The descriptive text categorizing the predicted results at block 120 depends on the MAH of the predicted result and on a set of previously determined threshold values of a property model. If, for a particular property model, the threshold value for good outliers is 0.4, the threshold value for bad outliers is 1.0, and the threshold value for extremely abnormal multi-channel data is 100, then the descriptive interpretations could be "Possible new type of sample" if MAH is greater than or equal to 0.4 and less than 1.0, "Unexpected result" if MAH is greater than or equal to 1.0 and less than 100, and "Sample not detected" if MAH is greater than or equal to 100. If MAH is less than 0.4, the predicted result is presumably valid and no descriptive interpretation is required. Help text is also provided at an output device of the user interface 32 in the vicinity of the sensor 2 that gives a recommended course of action as specified, for example, by an administrator of the operator's company. Thus, for example, if a predicted result is accompanied with the message "Possible new type of sample," the help text can instruct the operator to forward the sample to a laboratory for further characterization. If a predicted result is labeled as "Unexpected result," the operator can be instructed to verify that a sufficient quantity of sample is available, to verify that the type of material is identified correctly in the input fields of the user interface 32, and to take another measurement of the sample. In this case, if a second measurement of the sample gives an "Unexpected result," then the operator can be instructed to consider the material to be unacceptable. If MAH is greater than 100, the invalid prediction value can be omitted from the measurement results 14, and the message "Sample not detected" can be accompanied by help text that instructs the operator to contact the provider of the on-site measurement service to help investigate and remedy the problem.

When outliers are detected during on-site measurements in block 118 and a classification is made of the type of probable outlier in block 122, two events occur. First, the results are reported in block 120 and second, an investigation of the outliers is initiated in block 124. If the outliers are good in block 124, then there is an opportunity to extend the property model to compensate for a wider range of variations in the sample and the measurement conditions. If the outliers are not good in block 124, and if the training set does not need to be corrected or improved in block 128, then there is no opportunity to enhance the model and, since the current property model has not been altered, the current model is considered to be validated in block 130 and on-site measurements continue to be taken in block 116 with no intervention from these two events. If the outliers are good in block 124, then the customer can consult with the provider of the on-site measurement service to decide whether to extend the training set as indicated in block 126. This decision can be based on requirements or preferences of the customer, time and personnel resources of the provider, and economic considerations from both parties.

The ability of the on-site analysis system to detect probable outliers during on-site measurements at block 118, classify the type of probable outlier at block 112, and identify good outliers at block 124 provides the continual opportunity to adapt the property model to compensate for an effectively comprehensive set of influential factors which may change at some unpredictable time in the future. The outlier detection and classification occur on a real-time basis, so the customer is notified of probable outliers at the earliest opportunity. Furthermore, since the measurement results are stored in the data repository 58 of the central processor 10, the occurrence of probable outliers can trigger an automatic notification to the responsible parties, which can be the provider of the on-site analysis system, one or more administrative personnel at the customer's company, or both. This notification can begin the process of investigating the cause of the outliers and, in cases when one or more detected outliers are good, a decision can be made to extend the training set at block 126, and revise the property model (beginning with block 102 and continuing forward) so it will compensate for an effectively comprehensive set of a wider or different range of influential factors that occur during actual measurements.

Alternatively, it can be decided that one or more good outliers are not appropriate for inclusion in an extended training set. This decision can result from a situation in which the occurrence of the good outlier will probably be a rare occurrence or a situation in which the good outlier is caused by a type of material or an unusual measurement condition that the customer wants to avoid classifying as a valid measurement. Hence, the "effectiveness" of an effectively comprehensive set of influential factors can be defined or refined for a particular property model. The set of influential factors of a property model is considered to be effectively comprehensive until one or more good outliers is detected during on-site measurements, whereupon either the model is revised to accommodate a wider or different range of influential factors or a decision is made to exclude one or more types of good outliers as valid measurements. The on-site measurement system is adaptable both in its ability to accommodate a potentially changing set of influential factors based on real-time detection of probable outliers and to refine the definition of valid measurements according to established criteria.

Generation of a global calibration model involves the development of a global training set, which is then validated. The process of validating the calibration model is not only important in establishing the calibration model initially; the validation process attains even greater importance in maintaining the predictability of the calibration model over time to implement enhancement updates.

In generating global training sets for developing a property model, it is preferred to exercise discretion in selecting the data used in the training set. Data indiscriminately incorporated into the training set may introduce bad outliers, unwanted good outliers, and essentially duplicative information which, while increasing the size of the training set, does not necessarily improve its quality of prediction.

Desirably, relative to the total number of observed values of a property of interest available for development of a training set, a first subset of values is selected and used to generate instrument responses such that the property of interest is spanned over its expected range and the values typically span the range at approximately regular intervals. After this subset of values is used to generate a preliminary or a revised version of the calibration model, these observed values and the predicted values from the training set are used to compute the RMSECV. A separate subset of observed and predicted values from a validation set is then used to validate this version of the model and compute the RMSEP. The subset used for validation is generally less than the remainder of the original set of observed values less the first subset. If bad outliers are identified in an instrument-response set, those values are discarded. If a number of good outliers are identified, then consistent with the practice of incorporating minimal numbers of additional calibration data to avoid substantially duplicative or incrementally indistinct data, only a portion of the good outliers may be used to develop an extended training set.

The process of developing a calibration model that will compensate for an effectively comprehensive set of influential factors includes an investigation of pretreatment operations. Pretreatment consists of filtering a data set from a multichannel instrument to one or more subregions within a data set, operating on the data set with one or more mathematical transformations, or both. The combination of filtering and transforming multichannel data is observed to compensate for variations in some types of influential factors. Filtering may be performed before or preferably after the other data transformations. For other types of influential factors, an effective method of pretreatment may not be identified. In many such cases, compensation for those influential factors is possible by extending the training set with observations that span the expected ranges of the corresponding secondary variables. In some other cases, a combination of extended or partially extended training sets and pretreatment is found to be effective, where a partially extended training set includes observations that span some but not all of the expected range of variations of one or more influential factors. In the remaining cases, pretreatment and enhancement training sets will not provide effective compensation, and it will be necessary to control variations in one or more influential factors in order for the property to be measurable to the level of precision specified in the method and objectives (blocks 70 and 82 of FIG. 4) for the model. In those cases where either pretreatment or extension of a training set is possible, consistent with the practice of incorporating minimal numbers of additional calibration data, pretreatment is preferred.

Figure 6:
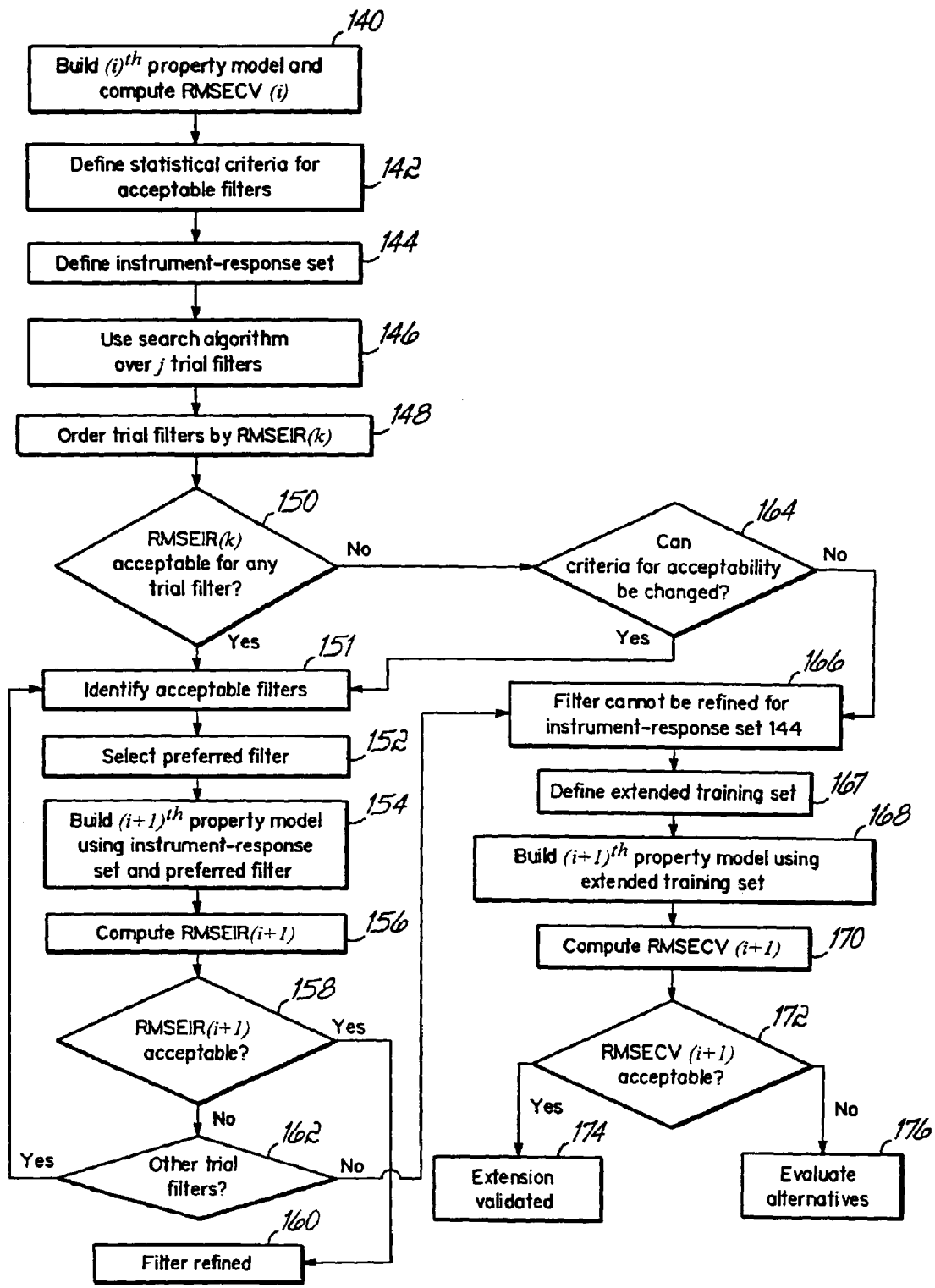
FIG. 6 is a flowchart of filter refinement.

The procedure for filtering an instrument response by selecting one or more subregions from the entire region of the instrument response as part of a pretreatment method to improve the predictive capabilities of a calibration model is defined as filter refinement. A flowchart of the filter refinement process is shown in FIG. 6. First, a preliminary property model, labeled the $i^{th}$ property model in block 140, is obtained or developed for the property of interest, and RMSECV(i) is calculated. The $i^{th}$ property model in block 140 can be the preliminary model of block 76 in FIG. 4, a revised preliminary model of block 86 in FIG. 4, the $i^{th}$ revised model of block 104 in FIG. 5, or the $i^{th}$ validated revised model of block 110 in FIG. 5. Filter refinement may be used to adjust the pretreatment in block 108 of FIG. 5.

Next, in block 142, statistical criteria for acceptable filters are defined in terms of the RMSECV of a preliminary property model that will satisfy the objectives of blocks 70 and 82 in FIG. 4, specifically the maximum value of RMSEP and the maximum absolute value of the offset of the validation curve of predicted versus observed results. For example, it may be determined that the objectives of blocks 70 and 82 for a property of interest will be satisfied if the RMSEP is not greater than 1.5 times the RMSECV of the preliminary model and the maximum absolute offset between predicted and observed values can be allowed to be as great as 50% of this RMSECV in order to compensate for the influential factors, where the offset can be calculated as the absolute value of the difference between the average predicted value and the average observed value.

Next, after such statistical criteria are defined, an instrument-response set is defined in block 144 by recording instrument responses acquired as the level of one or more influential factors is varied over a range. As used herein, a global instrument-response set is one for which the range spans the expected range of variations in each of the experimentally determined influential factors, and a partial instrument-response set is one for which the range spans part but not all of the expected range of variations of one or more factors. In the feasibility stage of model development, it is acceptable to use partial instrument-response sets. In the development of a model that is suitable for on-site measurements, it is preferred to use global instrument-response sets.

Next, in block 146, a procedure involving a search algorithm is used to compute RMSEIR for a number of trial filters containing one or more subregions, where the number of trials j is typically from 50 to 300 for a particular property model, although greater or lesser numbers can be used. Thus, from a number of subregions in a plurality of trial filters comprising discrete combinations of subregions, the multichannel data from applying each trial filter to an instrument response contains at least one subregion of data within the entire available region of data. The instrument-response set for this procedure can be partial or global, although it is preferred that the set be global. The specific subregions evaluated by the search algorithm can be selected by commercial software such as the Bruker OPUS Quant-2 product. These subregions can also be selected manually. The output from the search algorithm can be summarized in a table of trial filters that lists the corresponding RMSEIR and rank of the PLS model for each trial filter, where a trial filter comprises one or more subregions selected from the available multichannel region of a sensor-type. It is convenient to order the trial filters according to RMSEIR(k), where k ranges from 1 to j, as shown in block 148, such that RMSEIR(k) is less than RMSEIR(k+1) for each k from 1 to j−1, but this step is optional.

Next, in block 150, a decision is made whether one or more trial filters from block 148 satisfies the statistical criteria defined in block 142. If no such trial filter can be identified, then in block 164 the customer can be consulted to determine if less precise predictions will be acceptable. If the customer will change the criteria of block 142 such that at least one trial filter exists that satisfies these criteria and thereby adjusts the objectives defined in blocks 70 or 82 of FIG. 4, or if the outcome of block 150 is yes, then any of these trial filters may be selected as an acceptable filter in block 151. A preferred filter may be selected in block 152 from a group of acceptable filters by the following decision criteria. Criterion A: The acceptable filter that produces the smallest value of RMSEP is most preferred. Criterion B: If an acceptable filter is found that is composed of a smaller number of sub-regions than that identified by Criterion A, then the acceptable filter composed of a smaller number of sub-regions is preferred. If two or more such acceptable filters are identified, Criterion A is applied for those filters. Criterion C: If two or more acceptable filters composed of the same number of subregions are found from applying Criterion B, then acceptable filters corresponding to the smallest PLS rank are preferred. If two or more such acceptable filters are identified, Criterion A is applied for those filters.

In an alternative embodiment of the procedure for selecting the preferred filter, Criterion C may be used before Criterion B. It is also possible to select a preferred filter by using either Criterion B or Criterion C alone.

Next, in block 154 the $(i+1)^{th}$ property model is built from the preliminary $(i)^{th}$ property model by using the preferred filter of block 152. RMSEIR(i+1) is computed in block 156. In block 158, the RMSEIR of the $(i+1)^{th}$ property model must also meet the criteria of block 142, specifically the RMSEIR of the instrument-response set for the $(i+1)^{th}$ revised model must meet the same criteria as the RMSEIR of the instrument-response set for the $(i)^{th}$ property model for the preferred filter. If the RMSEIR of the revised model fails these criteria, and therefore is not acceptable in block 158, then a decision is made in block 162 whether some other acceptable filters of block 151 have not yet been considered. If yes, then the next most preferred filter is selected in step 152, and steps 154, 156, and 158 are repeated. If the RMSEIR of a revised property model satisfies these criteria, then RMSEIR(i+1) is acceptable in block 158, filter refinement is complete in block 160, and the identified preferred filter is called the refined filter.

Returning to block 164, if the customer criteria cannot be altered, then the filter cannot be refined for the instrument-response set of block 144, and it becomes necessary to extend the global training set in block 167 by including calibration data generated over a range of variations in the influential factors that are expected to occur during future measurements using the property model. The $(i+1)^{th}$ property model is built from this training set in block 168, and RMSECV(i+1) is computed in block 170. The decision in block 172 of whether RMSECV(i+1) is acceptable is based on the same criteria as used for block 158. If RMSECV(i+1) is acceptable in block 172, then the calibration model developed from the extended training set is validated in block 174. If RMSECV(i+1) is not acceptable in block 172, then it is necessary to evaluate alternatives in block 176. These alternatives include searching over additional trial filters in block 146 and continuing forward, using the $(i+1)^{th}$ property model of block 168 as the $i^{th}$ property model in block 140 and continuing forward, or selectively omitting calibration data in the training set of block 167 to define a partially extended training set for developing the $i^{th}$ property model in block 140 and continuing forward. This latter case corresponds to controlling one or more influential factors by deciding to redefine the objectives of the on-site analysis (blocks 70 and 82 of FIG. 4) to exclude measurements under conditions where the property is not measurable to the desired precision or to hold those measurement conditions constant. If none of the above alternatives is acceptable, it may be decided to use a different analytical method in blocks 70 and 82 for on-site analysis.

The calibration model described herein is generally capable of predicting values for the property of interest by compensating for variations in an effectively comprehensive set of measurement conditions and secondary material characteristics. Secondary variables which potentially influence instrument response can each be evaluated to generate one of three outcomes: the secondary variable has no effect or a minimal effect on instrument response; the secondary variable has an influential effect on instrument response, which can be entirely or substantially compensated by pretreatment; or the secondary variable has an influential effect on instrument response which cannot be compensated adequately by pretreatment, but can be compensated by extension of the training set. Note that pretreatment can include filter refinement. There is also a fourth outcome which does not involve prediction by the calibration model. This fourth outcome may result from determining if a property is measurable in the presence of variations of a secondary variable. In this determination, the variation in the property due to variations in the secondary variable over its expected range is compared with the limit of desired precision for predictions of the property of interest. If the range of this variation is a substantial percentage, or greater, of the limit of desired precision of a predicted result, the ability of the calibration model to predict values for the property of interest is hampered, and may prevent the prediction of usable values. The ability for the model to predict values is a function of the rate of change of the property of interest with respect to each secondary variable. For a particular secondary variable, if this rate of change is relatively small, variations in the secondary variable can be compensated by the property model. If this rate of change is relatively large compared with the limit of desired precision, then the secondary variable must be controlled by restricting the possible range of variation during data acquisition and the objectives of blocks 70 and 82 redefined accordingly, or an acceptable property model cannot be generated.

The generation of a calibration model according to the invention involves the consideration of experimental factors over a wide range in connection with predicting a property of interest, with testing for potential influence on the predicted result and, when effective methods of pretreatment can be identified, no longer requiring that the training set be expanded by including observations taken at different levels of influential factors. The result of this procedure is a calibration model which accounts for an effectively comprehensive range of influential factors. It is possible that a combination of pre-processing, pretreatment and calibration model revision may be employed in connection with a single variable, either primary or secondary.

An advantage of the calibration model developed as described herein is the ability to compensate for secondary variables previously considered too significant to overcome in a single calibration model across a group of two or more instruments of a particular sensor-type. One such set of secondary variables is the characteristic influential factors attributable to each measuring instrument in a group of similar instruments, where the collection of variations in these variables is described herein as instrument variance. Because of the complexities of manufacture, and the tolerances which necessarily exist in connection with the manufacture of the component parts, measuring instruments constructed from these component parts will not provide identical output in response to the same sample. Further, the response of each such measuring instrument will differ one from the other over time, as age will have a varying effect on the instrument collectively and the component parts individually. For example, component parts within manufacturing tolerances but produced in different batches may demonstrate different output properties over time. Two different instruments, even though manufactured at the same time, may be used to different degrees, effectively wearing out one instrument faster than the other.

Instead of generating a calibration model on one instrument, then necessarily transferring that model for use by another and developing instrument-specific correction algorithms, the calibration model generated herein compensates for variations of the characteristics of each instrument within a sensor-type and between such instruments by use of a sensor-type-specific property model. Thus, a single property model is generated for all instruments of a particular sensor-type, not multiple property models which must be replicated and corrected or adjusted individually for each instrument within a sensor-type and which must take into account the individual characteristics of each instrument. Significantly, for a collection of instruments of a particular sensor-type, the property model of the invention does not require any individual identification of the specific sensor in use for the purpose of building or using the model. Identification of the on-site location, and thus the instrument, may be important for billing, forecasting or archival purposes, among others, but the model operates without the need for actually identifying the particular instrument and thus the instrument's characteristics. In this sense, the instrument variance is considered in the same way as variation in temperature or sample presentation.

Instruments of a particular sensor-type must be sufficiently similar. To determine if discrete instruments of some sensor-type are sufficiently similar, the calibration set or a subset of the calibration set that had been used to build a multivariate model for one instrument is used to validate a second instrument over a range of measurement conditions. The set of predictions from the second instrument using this validation set is obtained from the model developed for the first instrument. If the RMSEP of the validation set is within an acceptable tolerance of RMSECV, for example, less than 1.5 times RMSECV of the training set used to develop the calibration model for the first instrument, the second instrument is determined to be sufficiently similar to the first instrument, and both instruments can use the same property model, that model being the model as developed for the first instrument without any modifications. Therefore, a group of instruments of a particular sensor-type are determined to be sufficiently similar by validating each instrument with one or more global property models. The group of such validated instruments produce results from each instrument that are statistically equivalent using a single property model for each property of interest. An acceptable tolerance of RMSECV of the training set for the property model can be specified as the desired precision value in the objectives of block 70 and/or 82 of FIG. 4.

The filter refinement procedure of FIG. 6 can be used to develop a property model that will compensate for instrument variance. First, in step 140, a global property model is obtained or developed to compensate for all influential factors except for instrument variance, and RMSECV(i) is calculated. This model is called a single-instrument global property model. After defining statistical criteria in block 142 as previously described, an instrument-response set is defined by taking a number of measurements on one or more instruments different from that used to develop the single-instrument property model. Then, additional steps are performed as indicated in blocks 146, 148, 150, 152, 154, 156, 158, as well as those in block 162 and 164 if required, until one of two outcomes occurs. In the first outcome, the filter is refined (160) and the model of step 154 is a multi-instrument global property model, while in the second outcome, it is found that the filter cannot be refined (166). As an alternative to the first outcome, an acceptable multi-instrument global property model can be built by using any acceptable filter. If the filter cannot be refined to at least the level of an acceptable filter, but the extended training set of block 168 leads to a successful validation in step 174, the model of block 168 is an acceptable multi-instrument global property model.

In reference to the alternatives previously described for block 176, in the case of instrument variance it is possible to selectively omit calibration data in the training set of block 168 acquired from one or more instruments to define a partially extended training set based on two or more instruments, develop the $i^{th}$ property model in block 140 based on this partially extended training set, and continue forward. If this procedure leads to the successful development of a multi-sensor global property model, it is likely that some aspect of the hardware of the omitted analytical instrument is flawed and that instrument should be rejected for use in an on-site sensor. It is also possible to test and accept or reject specific components of an instrument using this procedure.

Predicted values from a multi-instrument global property model can be used in a quality control procedure to accept or reject analytical instruments or components for use in the sensor devices of an on-site analytical system. In such a quality control procedure, predicted values are generated from one or more untested instruments or components using a previously established multi-instrument global property model. The quality-control data set is the instrument-response set formed from these new predictions. If the RMSEP of this instrument-response set satisfies the criteria of block 158 in FIG. 6, the new instrument or component is acceptable. If not, the training set can be extended in block 167 and a new multi-instrument global property model can be built in block 168. If the resulting RMSECV computed in block 170 is acceptable according to the criteria of block 172, then the property model developed from this extended training set (block 168) is adopted as the multi-instrument global property model. If the RMSECV is not acceptable according to the criteria of block 172, then the instrument is rejected and the new property model built in block 168 is not adopted. Generally, this quality control procedure is performed for all new or untested instruments that will be installed for on-site measurements. In addition, this quality control procedure can also be performed for new or untested components used in generating measurements, such as but not limited to probes, interferometers, and detectors.

The multi-instrument global property model is able to predict values of properties using single algorithms that do not contain any instrument-specific parameters. The multichannel data acquired from different instruments produce statistically equivalent results without using instrument-specific correction factors. Generally, only one instrument-specific computational data transformation is undertaken during the computation of measurement results 14 from measurement data 12, specifically during pre-processing in the local processor 34 of an individual sensor 2, at which time eccentricities in the sample spectrum attributable to the background spectrum unique to the sensor 2 are removed. No instrument-specific information for use by the modeling algorithms is transmitted to or stored at the central processor 10.

Though individual instrument characteristics can be compensated in practicing the invention, there are limits to the extent of compensation which can be performed. For example, it is not presently possible to generate a calibration model which can accept instrument responses from different types of spectrometers, such as NIR and Raman, and compensate for the different characteristics of each. The instruments should preferably be of the same sensor-type, usually from the same manufacturer, and be the same model. The instruments within a sensor-type should be sufficiently similar to generate statistically equivalent results, as described earlier. Most preferably, the instrument should exhibit narrow manufacturing tolerances as to those components which affect the instrument's data acquisition performance and its performance over time. Thus, in the case of a NIR spectrometer, it is important for the instruments to exhibit good interferometer alignment. Over time, it is important for the instruments to exhibit good light source reproducibility and data acquisition probe reproducibility. In the case of instruments utilizing other portions of the electromagnetic spectrum or instruments which generate a response non-spectroscopically, reproducibility of the component or components which interact with the sample, and the component or components which register the response, is desired.

As noted above, the invention also encompasses a method of generating measurement results for a customer and supplying information of value to the customer based on these results. The method incorporates a hardware infrastructure, software and data processing to create a material analysis service which encompasses the collection, transmission and manipulation of data, with delivery of information of value to the customer, to the original submitter of data or to an alternate location. The data and information are transmitted along a communication link.

EXAMPLES

The following detailed examples describe various aspects of the invention in greater detail. The examples are intended to enable one skilled in the art to practice the invention, not to limit the scope thereof. Numerous variations are possible without deviating from the spirit and scope of the invention.

Example 1

A feasibility study was done to determine if a property model could be developed to measure the concentration of squalane in squalene. In accordance with block 70 of FIG. 4, the method was defined as FT-NIR using the MATRIX Model F instrument manufactured by Bruker Optics, with sample presentation for liquid samples provided by closure caps with dimensions of 18-mm diameter×10-mm high manufactured by Cincinnati Container Corporation. The objectives for the property model included measurements of squalane in squalene having concentrations ranging from trace amounts to about 10 weight percent with a limit of desired precision of 0.10% or smaller as measured by RMSEP. The objectives further indicated that the measurements will be taken by non-skilled operators who will dispense about 1 mL of liquid samples into separate, disposable caps, and the sample temperature may vary from about 0 C to 60 C. In accordance with the block 72 of FIG. 4, the expected range of the concentration of squalane in squalene was defined as 0 to 10%, where the % symbol indicates a percentage calculated from the weight of solute and the weight of the solution.

A set of six samples with 0.00%, 2.00%, 4.00%, 6.00%, 8.00% and 10.00% of squalane (99%, Aldrich Chemical Company) in squalene (97%, Aldrich Chemical Company) were prepared to serve as calibration samples to generate a training set, shown as block 74 (FIG. 4), to assess model feasibility. The known values were determined by calculation of the concentrations expressed as weight percentages using the weights measured by an analytical balance. 1.0 mL of each sample was transferred to a separate, disposable cap. For each sample, one FT-NIR spectrum was acquired in the transflectance mode at ambient temperature (20 C).

The type of FT-NIR spectrometer used for all of the examples was MATRIX Model F instrument manufactured by Bruker Optics equipped with an InGaAs detector and a fiber optic probe approximately 91 cm long. The fiber optic probe was bundled with 200 optical fibers, 100 for illumination and 100 for collection. Each fiber was 100 μm in diameter, and the total illuminating area was about 3-mm in diameter. The spectral resolution of the spectrometer was 8 cm$^{-1}$ and the available spectral region of the spectrometer was from 4500 cm$^{-1}$ to 10,000 cm$^{-1}$. The spectra were acquired within a relatively brief period of time. Individual averaged spectra for a single sample were generated each within typically less than about one minute.

Figure 7:
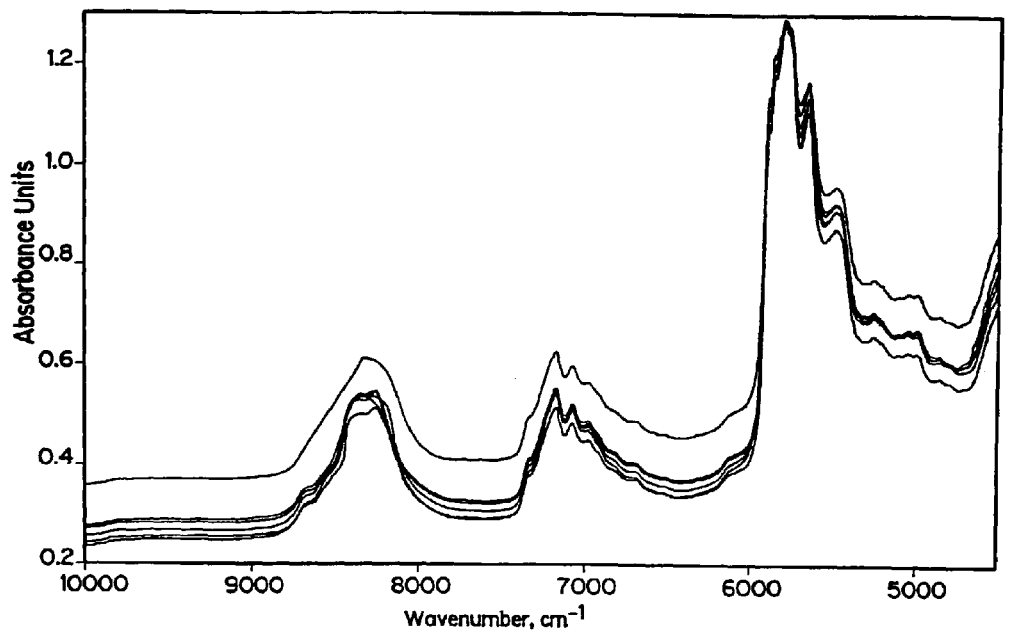
FIG. 7 is superposed NIR spectra of six samples of squalane in squalene at different concentrations.

A button on the fiber optic probe, serving as an input device of the user interface, was depressed to initiate data collection of 20 spectra at a scanning speed of 20 kHz and about 2 scans per second. The spectra were averaged in interferogram mode, converted to single-scan mode by fast Fourier Transform, and then converted to an absorbance spectrum for spectroscopic analysis according to absorbance spectrum=−log(single-channel spectrum/background spectrum)

wherein the reference or background spectrum for transflectance measurement was the average of 20 scans measured by direct contact of the fiber optic probe on a mirror surface. The six observed NIR spectra are shown in FIG. 7.

Figure 8:
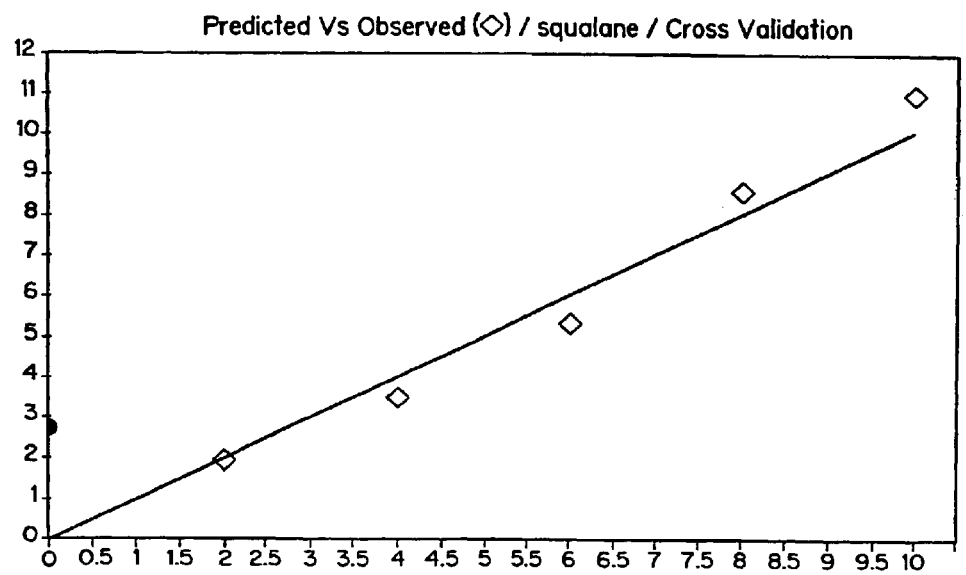
FIG. 8 is predicted versus observed values from the cross-validation of Model 1.0.

As indicated in block 76 of FIG. 4, these 6 spectra were the pre-processed instrument responses in the training set used to build an initial calibration model, herein called Model 1.0, according to the PLS method using Bruker OPUS Quant-2 software. In Examples 1 through 15, the calibration models were generated using a computer operating independently of the central processor, though this was not required. Model 1.0 was built using the entire available [Again question on use of "available"] spectral region from 4500 to 10,000 cm$^{-1}$ and with no data pretreatment. The feasibility of predictive measurements was assessed by cross-validation of the training set, which produced values of 86.95 for R$^2$ and 1.23% for RMSECV with a rank of 3. No outliers were detected in the training set. The observed and predicted values from the training set for Model 1.0 are given in Table 1, and the corresponding calibration curve is shown in FIG. 8. These results, specifically since the coefficient of determination was greater than 60, demonstrated that the property was measurable (block 78) and it was feasible to develop a model (block 100, FIG. 5) to predict the concentration of squalane in squalene.

TABLE 1

| Sample No. | Observed (%) | Predicted (%) | Residual (Obs − Pred) |
|---|---|---|---|
| 1 | 0.00 | 2.71 | −2.71 |
| 2 | 2.00 | 1.92 | 0.08 |
| 3 | 4.00 | 3.50 | 0.50 |
| 4 | 6.00 | 5.33 | 0.67 |
| 5 | 8.00 | 8.54 | −0.54 |
| 6 | 10.00 | 10.89 | −0.89 |

Figure 9:
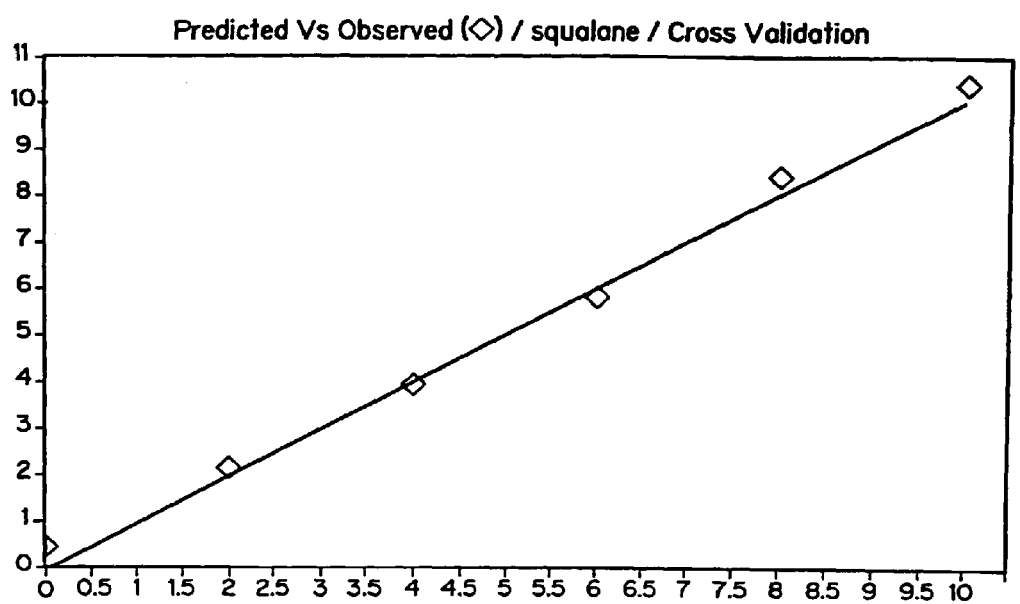
FIG. 9 is predicted versus observed values from the cross-validation of Model 1.1.

To increase the sensitivity of the method for the identification of influential factors (block 84) in the following examples, it was preferred to use a refined filter (block 160, FIG. 6) as the pretreatment of block 86. Filter refinement, using the OPUS Quant-2 software to select trial filters, yielded Model 1.1, which was a property model with a refined filter of 4597.5 to 5025.6 cm$^{-1}$. Model 1.1 gave 99.1 for R$^2$ and 0.325% for RMSECV with an optimal rank of 3. The resulting calibration curve and the table of observed and predicted values from the training set for Model 1.1 are shown in FIG. 9 and Table 2. No outliers were detected in the training set.

TABLE 2

| Sample No. | Observed (%) | Predicted (%) | Residual (Obs − Pred) |
|---|---|---|---|
| 1 | 0.00 | 0.49 | −0.49 |
| 2 | 2.00 | 2.19 | −0.19 |
| 3 | 4.00 | 3.94 | 0.06 |
| 4 | 6.00 | 5.80 | 0.20 |
| 5 | 8.00 | 8.39 | −0.39 |
| 6 | 10.00 | 10.40 | −0.40 |

Example 2

Figure 10:
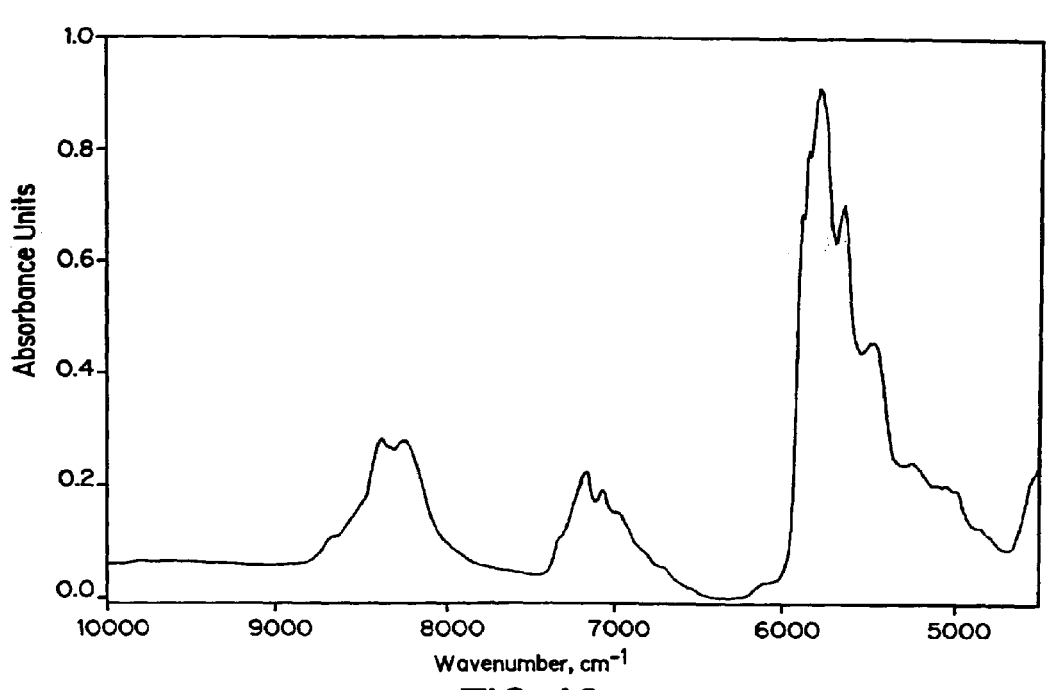
FIG. 10 is superposed NIR spectra for different environmental light intensities.

The light intensity of the environment is a potentially influential factor (block 84). The lights are expected to be either on or off. To determine if a difference in the intensity of background light in the room will affect the concentrations predicted by Model 1.1 (block 88), the spectrum of a single sample with an observed value of 2.00% of squalane in squalene was acquired four times with the overhead fluorescent room lights on and four times with the lights off without changing any other measurement conditions. FIG. 10 shows the superposition of the resulting eight spectra. Since no measurable differences are observed between the spectra, variations in the light intensity of this particular environment will not affect the predicted concentrations.

To further demonstrate that the light intensity is not an influential factor, Model 1.1 was used to compute predicted values of the concentrations corresponding to each of the eight spectra for the 2.00% squalane samples. As shown in Table 3, the residuals between the observed and predicted values from the validation set each expressed in percent are each less than the RMSECV of Model 1.1. Specifically, since each residual value in percent is much less than the RMSECV of 0.325%, and since each residual value is less than the desired precision value of 0.10%, the results were statistically equivalent. Thus, variation in the light intensity of the environment was not an influential factor (block 88) in the prediction of concentrations of squalane in squalene by FT-NIR measurements to a precision within the limit of desired precision, and no revision to the preliminary model (block 90) was required.

TABLE 3

| Spectrum No. | Light | Observed (%) | Predicted (%) | Residual (Obs − Pred) |
|---|---|---|---|---|
| 1 | Off | 2.00 | 2.01 | 0.01 |
| 2 | Off | 2.00 | 1.99 | −0.01 |
| 3 | Off | 2.00 | 2.02 | 0.02 |
| 4 | Off | 2.00 | 2.01 | 0.01 |
| 5 | On | 2.00 | 2.01 | 0.01 |
| 6 | On | 2.00 | 2.01 | 0.01 |
| 7 | On | 2.00 | 2.01 | 0.01 |
| 8 | On | 2.00 | 2.01 | 0.01 |

Example 3

Figure 11:
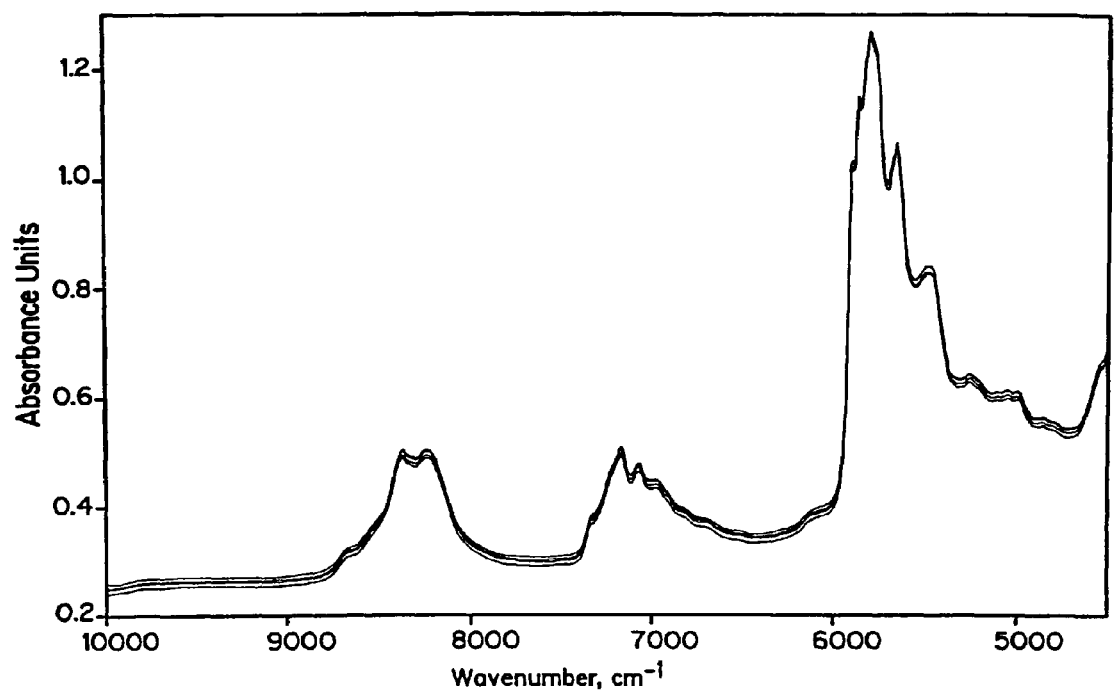
FIG. 11 is superposed NIR spectra for different sample cap orientations.

The orientation of the sample cap is a potentially influential factor (block 84). The orientations are expected to be random. To determine if variation in the orientation of the sample cap (block 86) will affect the predicted concentrations (block 88), a sample of 1.00% of squalane in squalene was prepared and measured with four different cap orientations. The initial orientation of the cap was selected at random, and additional orientations were attained by successively rotating the cap by approximately 90 degrees about an axis perpendicular to the bottom of the cap between measurements. As shown in FIG. 11, measurable differences were observed in these spectra, indicating that orientational variance is probably an influential factor.

Figure 12:
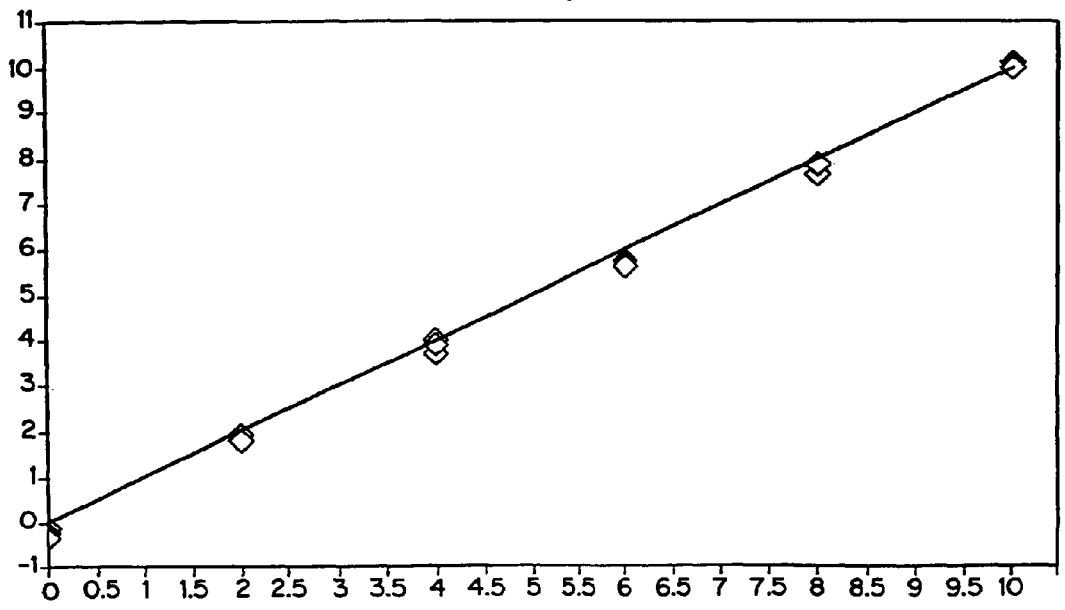
FIG. 12 is predicted versus observed values from the validation of Model 1.1 for different sample cap orientations.

The six calibration samples in the training set of Example 1, each with a sample cap orientation labeled as orientation 1, were then measured with three additional orientations selected at random, labeled as orientations 2, 3, and 4, each rotationally differing by about 90. It should be understood that a particular numbered orientation, such as orientation 3, indicates only the order in which a particular random orientation was generated in a sequence of random orientations for a sample measurement, so orientation 3, for example, indicates only that this was the third random orientation measured. The resulting additional 18 spectra were used as a validation set to predict squalane concentrations according to Model 1.1 with the refined filter of Model 1.1 for pretreatment (block 90). RMSEP was 0.234%, $R^2$ was 99.53, and the validation curve is shown in FIG. 12. The observed and predicted values from the validation set are listed in Table 4.

Since the RMSEP of the preliminary model in the presence of variations in sample cap orientation exceeded the limit of desired precision, the residuals were statistically significant, and orientational variance was determined to be an influential factor (block 88). It was therefore necessary to build a revised model (block 90) to compensate for orientational variance.

TABLE 4

| Sample No. | Orientation | Observed (%) | Predicted (%) | Residual (Obs − Pred) |
|---|---|---|---|---|
| 1 | 2 | 0.00 | −0.19 | 0.19 |
| 1 | 3 | 0.00 | −0.36 | 0.36 |
| 1 | 4 | 0.00 | −0.38 | 0.38 |
| 2 | 2 | 2.00 | 1.87 | 0.13 |
| 2 | 3 | 2.00 | 1.80 | 0.20 |
| 2 | 4 | 2.00 | 1.77 | 0.23 |
| 3 | 2 | 4.00 | 4.02 | −0.02 |
| 3 | 3 | 4.00 | 3.70 | 0.30 |
| 3 | 4 | 4.00 | 3.90 | 0.10 |
| 4 | 2 | 6.00 | 5.76 | 0.24 |
| 4 | 3 | 6.00 | 5.67 | 0.33 |
| 4 | 4 | 6.00 | 5.66 | 0.34 |
| 5 | 2 | 8.00 | 7.65 | 0.35 |
| 5 | 3 | 8.00 | 7.84 | 0.16 |
| 5 | 4 | 8.00 | 7.81 | 0.19 |
| 6 | 2 | 10.00 | 10.08 | −0.08 |
| 6 | 3 | 10.00 | 10.06 | −0.06 |
| 6 | 4 | 10.00 | 10.02 | −0.02 |

Figure 13:
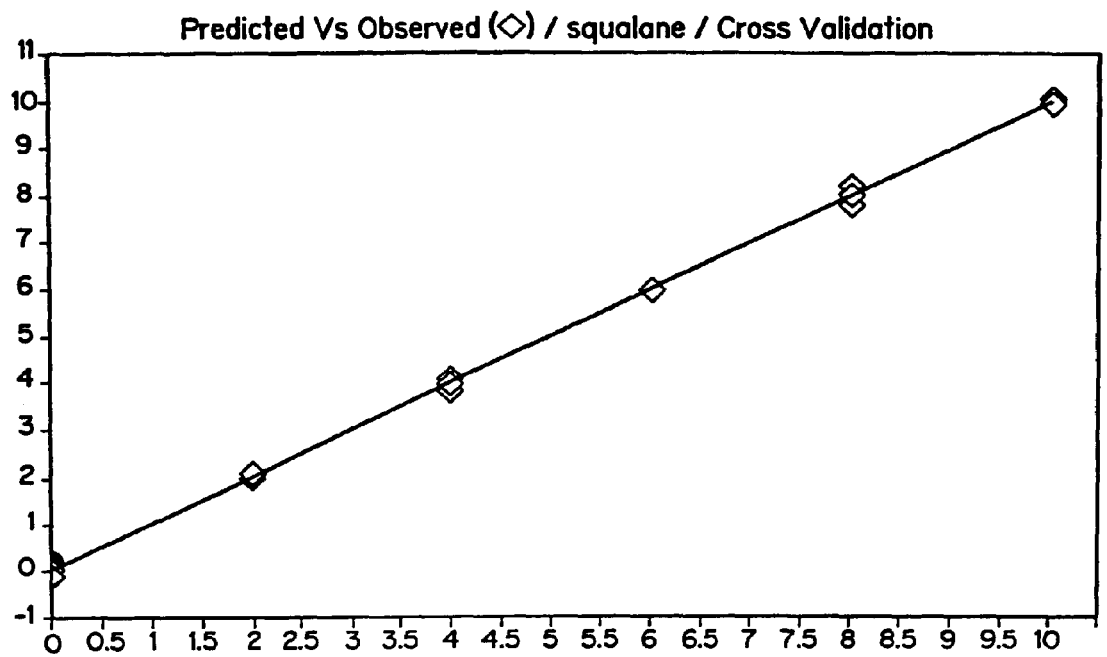
FIG. 13 is predicted versus observed values from the cross-validation of Model 3.0.

In order to revise the preliminary model so it would compensate for orientational variance, the twenty-four spectra obtained from measurements of the four different orientations at each concentration, which were the spectra used to generate the predicted values listed in Tables 1 and 4, were then used as the training set (block 102, FIG. 5) to build Model 3.0. Assuming there was an approximately quadratic relationship in the observed versus predicted values in FIGS. 9 and 12, four different levels were used for the orientations in the training set. Using the same refined filter identified for Model 1.1, namely 4597.5 to 5025.6 cm$^{-1}$, Model 3.0 was a property model that yielded values of 99.92 for $R^2$ and 0.098% for RMSECV with a rank of 5 (block 104). No outliers were detected (block 106). It is noted that to compensate for orientational variance, Model 3.0 required two additional PLS factors compared with Model 1.1. The calibration curve for Model 3.0 is shown in FIG. 13.

Figure 14:
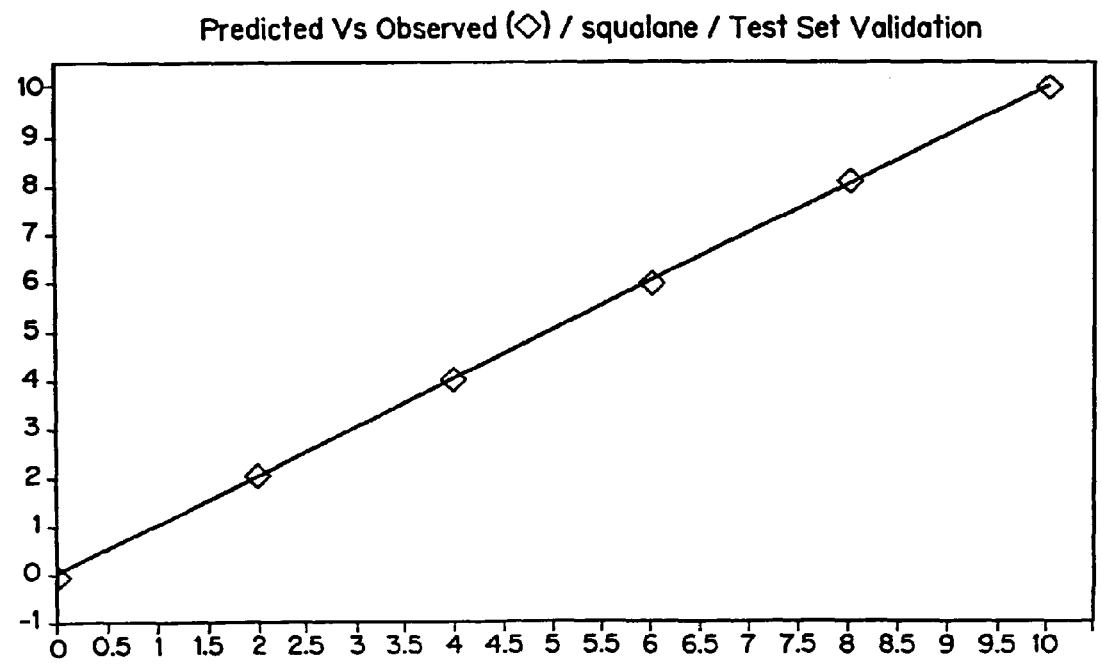
FIG. 14 is predicted versus observed values from the validation of Model 3.0 for different sample cap orientations.

Model 3.0 was validated using the same calibration set but with validation measurements taken at new random orientations, labeled as orientation 5 for each sample (block 108). The validation gave RMSEP of 0.046% (block 110) which showed a significant improvement in the predicted results compared with the RMSEP of 0.234% obtained using Model 1.1. No outliers were detected (block 112). The validation curve is shown in FIG. 14. The observed and predicted values from the validation set are in Table 5. Since RMSEP was less than the desired precision value of 0.10%, the residuals were statistically insignificant and the revised preliminary model demonstrated that the property was still measurable (block 92) to the limit of desired precision in the presence of variations in orientation.

TABLE 5

| Sample No. | Orientation | Observed (%) | Predicted (%) | Residual (Obs − Pred) |
|---|---|---|---|---|
| 1 | 5 | 0.00 | −0.07 | 0.07 |
| 2 | 5 | 2.00 | 2.05 | −0.05 |
| 3 | 5 | 4.00 | 3.98 | 0.02 |
| 4 | 5 | 6.00 | 5.94 | 0.06 |
| 5 | 5 | 8.00 | 8.02 | −0.02 |
| 6 | 5 | 10.00 | 9.98 | 0.02 |

Example 4

The sample pathlength for the squalane-squalene mixture, which is twice the distance from the air-liquid interface at the top of the sample volume to the reflective surface of the sample cap at the bottom of the sample, is a potentially influential factor (block 84) since the intensity of the NIR absorbance by the sample is proportional to the sample pathlength. The pathlength for a particular measurement is determined by the dimensions of the cap and the volume of sample dispensed into the cap.

Additional aspects of the method and objectives of block 70 are now defined. Suppose that the disposable caps of Examples 1 to 3 are to be used as economical sample holders for remote measurements. Since these caps are not manufactured identically, variations in the dimensions of the caps, and hence of the sample pathlength for a uniform volume of material, are inevitable. Further suppose that disposable pipettes with 0.25 mL graduations will be used as economical sample dispensers for remote measurements. Variations in sample volume are expected to occur under actual measurement conditions due to variations in operator technique in measuring and dispensing sample volumes. Therefore, pathlength variance is expected to occur during future measurements due to variations in at least two experimental factors involved in sample presentation consisting of dispensing material into different disposable caps using a disposable pipette with 0.25 mL graduations.

Figure 15:
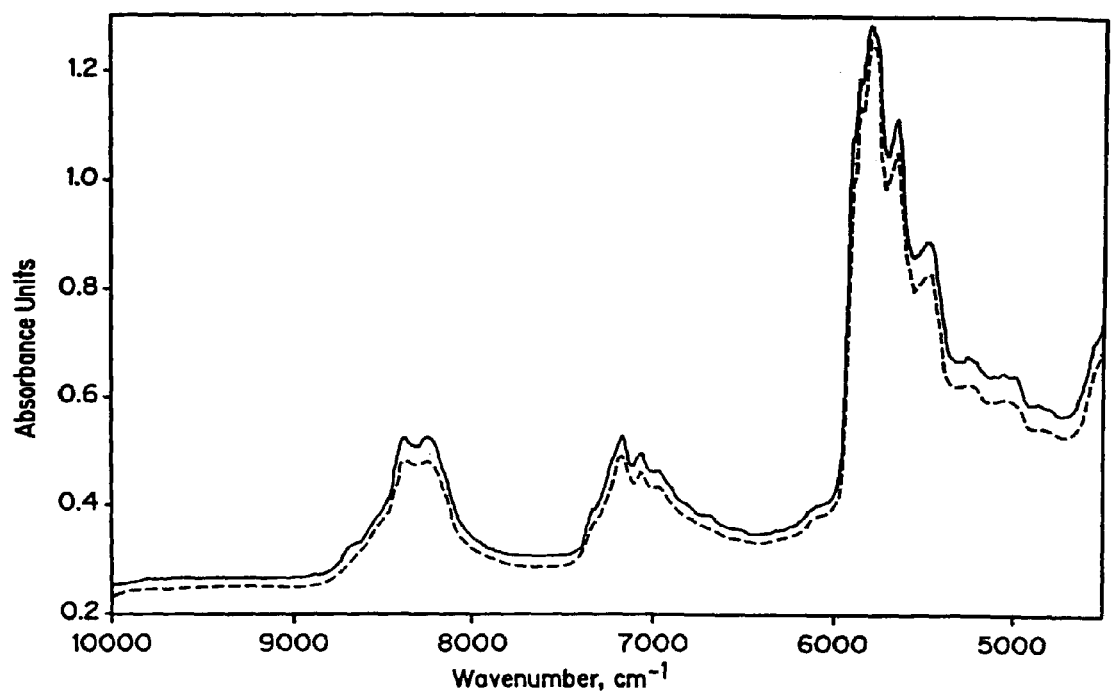
FIG. 15 is superposed NIR spectra for different sample pathlengths.

To determine whether dispensing material into different caps can affect the predicted concentrations (block 88), 1.0 mL of 1% squalane in squalene was dispensed into two different caps using a pipette with 0.25 mL graduations. The FT-NIR spectra obtained on these two subsamples, each in a different random orientation, showed observable differences in intensities at various wavenumbers as shown in FIG. 15, so pathlength is probably an influential factor.

Figure 16:
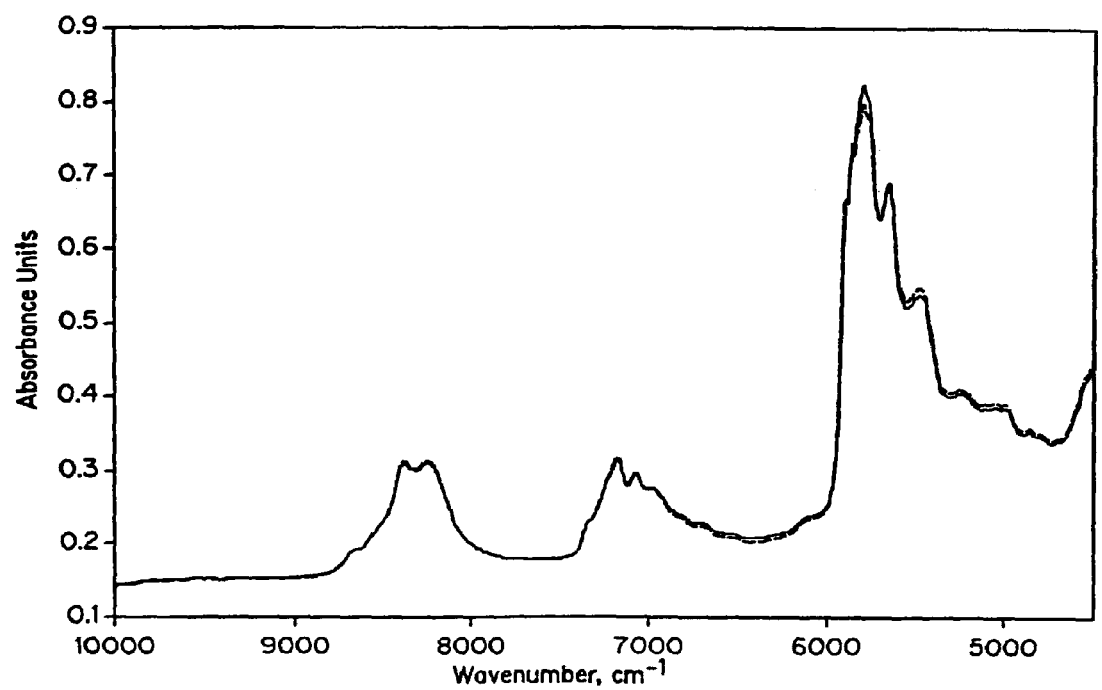
FIG. 16 is superposed transformed spectra after vector normalization pretreatment of the FIG. 15 NIR spectra.

Mathematical transformations were next considered for the definition of pretreatment as indicated in block 102. Normalization techniques, such as min-max normalization, vector normalization (VN) and multiplicative scattering correction (MSC), can be used to compensate for at least some of the variation in signal intensity. For example, vector normalization transformed the spectra of FIG. 15 into the spectra of FIG. 16.

To compensate for differences in spectral intensities which remain after pretreatment, additional calibration data can be included in the training set 102 which intentionally produce a range of spectral intensities if further improvement in the precision of the model is desired. Variations in pathlength can be intentionally introduced by using a selection of different sample volumes to span the range of pathlengths that are expected to occur during future measurements.

To compensate for shorter pathlengths, for example, a sample volume of 0.5 mL was tested. Model 3.0 predicted that a validation set generated from the instrument responses from 0.5 mL of a 1.00% squalane validation sample in two random orientations contained 2.93% and 2.94% squalane. These predictions were poor because Model 3.0 did not include training measurements or data pretreatment that would compensate for variations in pathlength. Since the residuals of the validation results, 1.93% and 1.94%, were greater than the desired limit of precision, the residuals were statistically significant, pathlength variance was determined to be an influential factor, and it was necessary to build a revised model (block 86).

Figure 17:
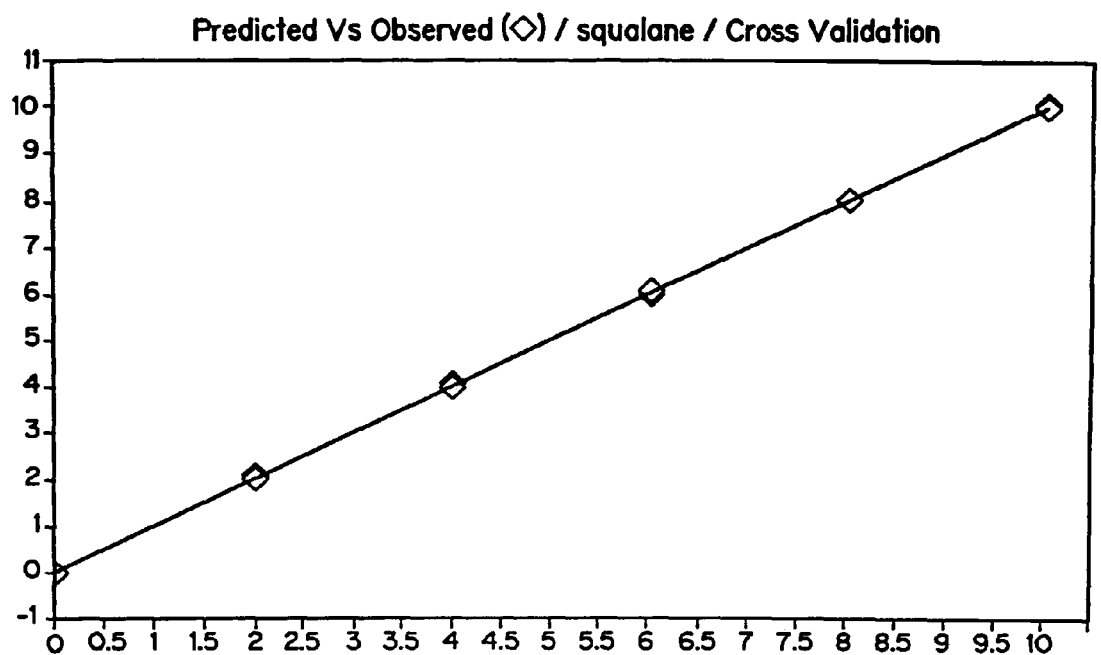
FIG. 17 is predicted versus observed values from the cross-validation of Model 4.0.

Model 4.0 was built (block 104) as a property model by pretreatment of the calibration spectra with vector normalization and a refined filter (block 160, FIG. 6) of 5195.3 cm$^{-1}$ to 6398.7 cm$^{-1}$. Model 4.0 produced values of 99.99 for $R^2$ and 0.0313% for RMSECV with a rank of 6. The calibration curve from the training set of Model 4.0 is shown in FIG. 17. No outliers were detected (block 106).

The predicted values for the 0.5 mL 1.00% squalane validation sample in two random orientations (block 108) using Model 4.0 became 1.35% and 1.44%, compared with the corresponding values of 2.93% and 2.94% that had been predicted from Model 3.0 with no adjustments in pretreatment. Since the residuals of the validation measurements using Model 4.0, 0.35% and 0.44%, were greater than the desired precision value, the defined pretreatment was not adequate to compensate for pathlength variance and it was necessary to extend the training set.

Figure 18:
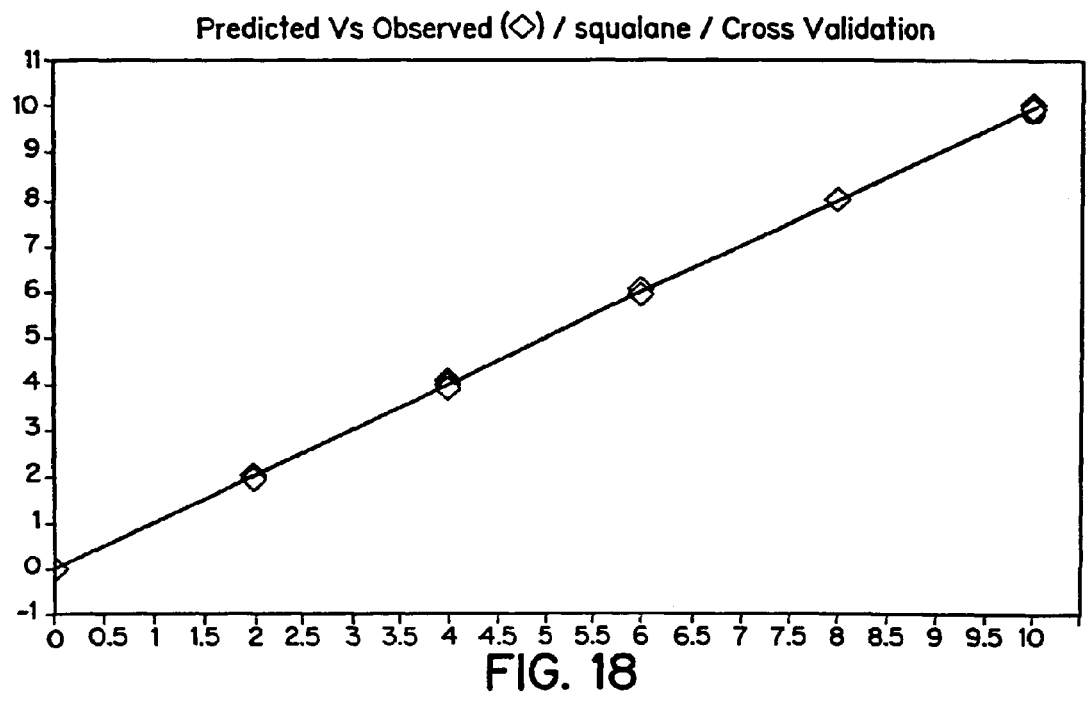
FIG. 18 is predicted versus observed values from the cross-validation of Model 4.1.

To make further improvements in the accuracy and precision of predicted results for 0.5 mL sample volumes, three additional calibration samples were prepared using low, middle, and high levels of concentrations to span the range of concentrations in the training set. Assuming that the calibration curve for FIG. 17 was linear, three levels were sufficient to span the expected range. Specifically, 0.00%, 6.00% and 10.00% samples were prepared with 0.5 mL sample volumes to build an extended training set (block 102) for Model 4.1. The data pretreatment was the same as that used for Model 4.0, but the training set was extended to include 12 additional spectra of the samples with 0.00%, 6.00% and 10.00% concentrations, taking spectra for each sample in four different random orientations. Model 4.1 (block 104) was a property model that produced values of 99.98 for $R^2$ and 0.052% for RMSECV with a rank of 7. No outliers were detected (block 106). The calibration curve of Model 4.1 is shown in FIG. 18.

The predicted values of concentration for the 1.00% validation sample then became 1.01% and 1.04% for two different random orientations (block 108) using Model 4.1. Since point estimates of RMSEP, taken as the residuals 0.01% and 0.04%, were each less than the desired precision value, the residuals were statistically insignificant and the revised preliminary model demonstrated that the property was still measurable (block 92) in the presence of pathlength and orientational variations. This process can be continued to extend the training set to span the particular range of sample volumes and, hence, pathlengths that are anticipated to occur during actual measurements in the future.

Example 5

Sample temperature is a potentially influential factor (block 84). A validation sample was prepared with 1.00% of squalane in squalene. FT-NIR spectra were obtained on two subsamples each at sample temperatures of 0 C, 20 C and 60 C. Predicted values of the squalane concentration in the two validation samples were computed for each spectrum using Model 4.1 and listed in Table 6. Since the residuals at 60 C are greater than the limit of desired precision (block 88), temperature was determined to be an influential factor (block 88), and it was necessary to revise the preliminary model (block 90).

TABLE 6

| 1.00% squalane | 20 C. | | 0 C. | | 60 C. | |
| --- | --- | --- | --- | --- | --- | --- |
| Subsample Number | Predicted (%) | Residual | Predicted (%) | Residual | Predicted (%) | Residual |
| 1 | 1.03 | −0.03 | 0.94 | 0.06 | 1.28 | −0.28 |
| 2 | 1.04 | −0.04 | 0.96 | 0.04 | 1.14 | −0.14 |

Figure 19:
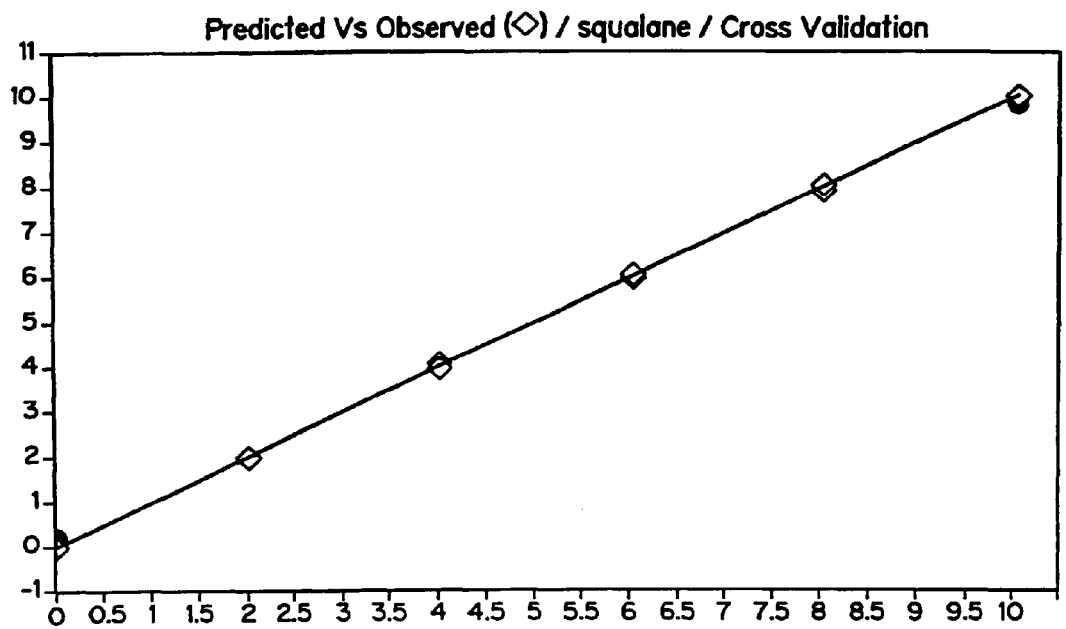
FIG. 19 is predicted versus observed values from the cross-validation of Model 5.0.

To compensate for variations in sample temperature, the training set for Model 4.1 was extended (block 102). The additional calibration spectra were generated by measuring three 1.0 mL calibration samples, with 0.00%, 6.00% and 10.00% squalane concentrations in squalene, each at a low temperature (0 C) and a high temperature (60 C), generating spectra using four random cap orientations at each temperature and concentration. Model 5.0 was a property model built from this extended training set (block 104), which was constructed to predict squalane concentration in the range from 0 to 10% with compensation for variations in temperature, cap orientation and pathlength. The refined filter (block 160, FIG. 6) for Model 5.0 was identified as the subregion from 5449.9 cm$^{-1}$ to 7501.8 cm$^{-1}$ using vector normalization as the pretreatment transformation (block 102). Model 5.0 produced values of 99.99 for R$^2$ and 0.042% for RMSECV (block 104) with a rank of 9. The calibration curve from the training set of Model 5.0 is shown in FIG. 19. No outliers were detected in the training set (block 106). The observed and predicted values are given in Table 7.

TABLE 7

| Sample No. | Volume | Temperature | Observed (%) | Predicted (%) | Residual (Obs − Pred) |
|---|---|---|---|---|---|
| 1 | 1.0 mL | Ambient | 0.00 | 0.01 | −0.01 |
| 2 | 1.0 mL | Ambient | 0.00 | 0.01 | −0.01 |
| 3 | 1.0 mL | Ambient | 0.00 | −0.03 | 0.03 |
| 4 | 1.0 mL | Ambient | 0.00 | 0.00 | 0.00 |
| 5 | 1.0 mL | Ambient | 2.00 | 1.98 | 0.02 |
| 6 | 1.0 mL | Ambient | 2.00 | 2.01 | −0.01 |
| 7 | 1.0 mL | Ambient | 2.00 | 1.99 | 0.01 |
| 8 | 1.0 mL | Ambient | 2.00 | 1.96 | 0.04 |
| 9 | 1.0 mL | Ambient | 4.00 | 4.08 | −0.08 |
| 10 | 1.0 mL | Ambient | 4.00 | 4.02 | −0.02 |
| 11 | 1.0 mL | Ambient | 4.00 | 4.01 | −0.01 |
| 12 | 1.0 mL | Ambient | 4.00 | 4.04 | −0.04 |
| 13 | 1.0 mL | Ambient | 6.00 | 5.94 | 0.06 |
| 14 | 1.0 mL | Ambient | 6.00 | 5.93 | 0.07 |
| 15 | 1.0 mL | Ambient | 6.00 | 5.98 | 0.02 |
| 16 | 1.0 mL | Ambient | 6.00 | 5.94 | 0.06 |
| 17 | 1.0 mL | Ambient | 8.00 | 7.90 | 0.10 |
| 18 | 1.0 mL | Ambient | 8.00 | 8.03 | −0.03 |
| 19 | 1.0 mL | Ambient | 8.00 | 7.99 | 0.01 |
| 20 | 1.0 mL | Ambient | 8.00 | 8.05 | −0.05 |
| 21 | 1.0 mL | Ambient | 10.00 | 10.01 | −0.01 |
| 22 | 1.0 mL | Ambient | 10.00 | 10.02 | −0.02 |
| 23 | 1.0 mL | Ambient | 10.00 | 10.01 | −0.01 |
| 24 | 1.0 mL | Ambient | 10.00 | 10.06 | −0.06 |
| 25 | 0.5 mL | Ambient | 0.00 | 0.00 | 0.00 |
| 26 | 0.5 mL | Ambient | 0.00 | −0.01 | 0.01 |
| 27 | 0.5 mL | Ambient | 0.00 | 0.01 | −0.01 |
| 28 | 0.5 mL | Ambient | 0.00 | 0.02 | −0.02 |
| 29 | 0.5 mL | Ambient | 6.00 | 6.04 | −0.04 |
| 30 | 0.5 mL | Ambient | 6.00 | 6.05 | −0.05 |
| 31 | 0.5 mL | Ambient | 6.00 | 5.97 | 0.03 |
| 32 | 0.5 mL | Ambient | 6.00 | 5.91 | 0.09 |
| 33 | 0.5 mL | Ambient | 10.00 | 10.05 | −0.05 |
| 34 | 0.5 mL | Ambient | 10.00 | 9.98 | 0.02 |
| 35 | 0.5 mL | Ambient | 10.00 | 10.01 | −0.01 |
| 36 | 0.5 mL | Ambient | 10.00 | 9.98 | 0.02 |
| 37 | 1.0 mL | Low | 0.00 | −0.02 | 0.02 |
| 38 | 1.0 mL | Low | 0.00 | −0.03 | 0.03 |
| 39 | 1.0 mL | Low | 0.00 | −0.01 | 0.01 |
| 40 | 1.0 mL | Low | 0.00 | 0.03 | −0.03 |
| 41 | 1.0 mL | Low | 6.00 | 6.10 | −0.10 |
| 42 | 1.0 mL | Low | 6.00 | 6.01 | −0.01 |
| 43 | 1.0 mL | Low | 6.00 | 5.99 | 0.01 |
| 44 | 1.0 mL | Low | 6.00 | 6.03 | −0.03 |
| 45 | 1.0 mL | Low | 10.00 | 9.99 | 0.01 |
| 46 | 1.0 mL | Low | 10.00 | 9.93 | 0.07 |
| 47 | 1.0 mL | Low | 10.00 | 10.00 | 0.00 |
| 48 | 1.0 mL | Low | 10.00 | 9.98 | 0.02 |
| 49 | 1.0 mL | High | 0.00 | 0.12 | −0.12 |
| 50 | 1.0 mL | High | 0.00 | −0.05 | 0.05 |
| 51 | 1.0 mL | High | 0.00 | 0.00 | 0.00 |
| 52 | 1.0 mL | High | 0.00 | 0.02 | −0.02 |
| 53 | 1.0 mL | High | 6.00 | 5.98 | 0.02 |
| 54 | 1.0 mL | High | 6.00 | 6.03 | −0.03 |
| 55 | 1.0 mL | High | 6.00 | 6.00 | 0.00 |
| 56 | 1.0 mL | High | 6.00 | 6.04 | −0.04 |
| 57 | 1.0 mL | High | 10.00 | 9.96 | 0.04 |
| 58 | 1.0 mL | High | 10.00 | 10.04 | −0.04 |
| 59 | 1.0 mL | High | 10.00 | 9.96 | 0.04 |
| 60 | 1.0 mL | High | 10.00 | 9.96 | 0.04 |

As shown in Table 8A, the results predicted from Model 5.0 for the two original validation samples showed no significant differences from the known value at each measured temperature and a considerable improvement in predictability compared with Table 6.

TABLE 8A

| 1.00% squalane | 20° C. | | 0° C. | | 60° C. | |
|---|---|---|---|---|---|---|
| Subsample Number | Predicted (%) | Residual (Obs − Pred) | Predicted (%) | Residual (Obs − Pred) | Predicted (%) | Residual (Obs − Pred) |
| 1 | 0.99 | 0.01 | 0.99 | 0.01 | 1.02 | −0.02 |
| 2 | 1.01 | −0.01 | 1.02 | −0.02 | 0.98 | 0.02 |

A 2.00% squalane in squalene sample was then measured at two other temperatures within the anticipated 0-60 C range to create a small validation set (block 108). Spectra were acquired for this sample at 5 C and 40 C, and concentrations were predicted based on Model 4.1 without temperature compensation and Model 5.0 with temperature compensation. The predicted values from the validation set are shown below in Table 8B. Since the residuals of Model 5.0 were each less than the desired limit of precision, the revised model was able to compensate for variations in sample temperature, pathlength, and orientation measured within the expected range, and the property was still measurable (block 92).

TABLE 8B

| 2.00% Squalane | Model 4.1 | | Model 5.0 | |
|---|---|---|---|---|
| Subsample Number | Predicted (%) | Residual (Obs − Pred) | Predicted (%) | Residual (Obs − Pred) |
| 1 (5° C.) | 1.87 | 0.13 | 2.02 | −0.02 |
| 2 (5° C.) | 1.92 | 0.08 | 2.04 | −0.04 |
| 1 (40° C.) | 2.13 | −0.13 | 2.03 | −0.04 |
| 2 (40° C.) | 2.12 | −0.12 | 2.03 | −0.03 |

Example 6

Humidity of the atmosphere is a potentially influential factor (block 84). Although a NIR instrument may be tightly sealed, moisture may still get into the interior of the instrument over an extended time. Furthermore, part of the light path between the probe and the sample may be open to the environment. Humidity in the air either inside or outside the instrument may affect the obtained NIR spectrum of a sample.

In general, there are two approaches to overcoming potential variations in environmental humidity. A traditional approach, one that would typically be practiced in a laboratory by trained scientists, would be to measure a background spectrum under the actual environmental conditions immediately before each sample measurement. Then, pre-processing the acquired spectrum of the sample with the background spectrum would eliminate environmental factors such as moisture interference automatically. However, this approach is not convenient or reliable for on-site measurements by non-skilled operators. This traditional approach may also be inadequate in compensating for unexpected short term changes in ambient humidity that could occur, for example, if an operator were to breathe moist air into the environment near the light path to the detector of the instrument.

The second approach is to include a small number of spectra in the training set that are generated with a range of humidities that would be expected to occur under actual conditions during remote testing. Since the NIR spectral features of water are much sharper than most other types of NIR features from condensed phase samples, variations in humidity can be readily discriminated and compensated by the PLS calibration model. Therefore, the potential interference from variations in humidity can be avoided by extending the training set to include some spectra that span a range of humidities.

Figure 20:
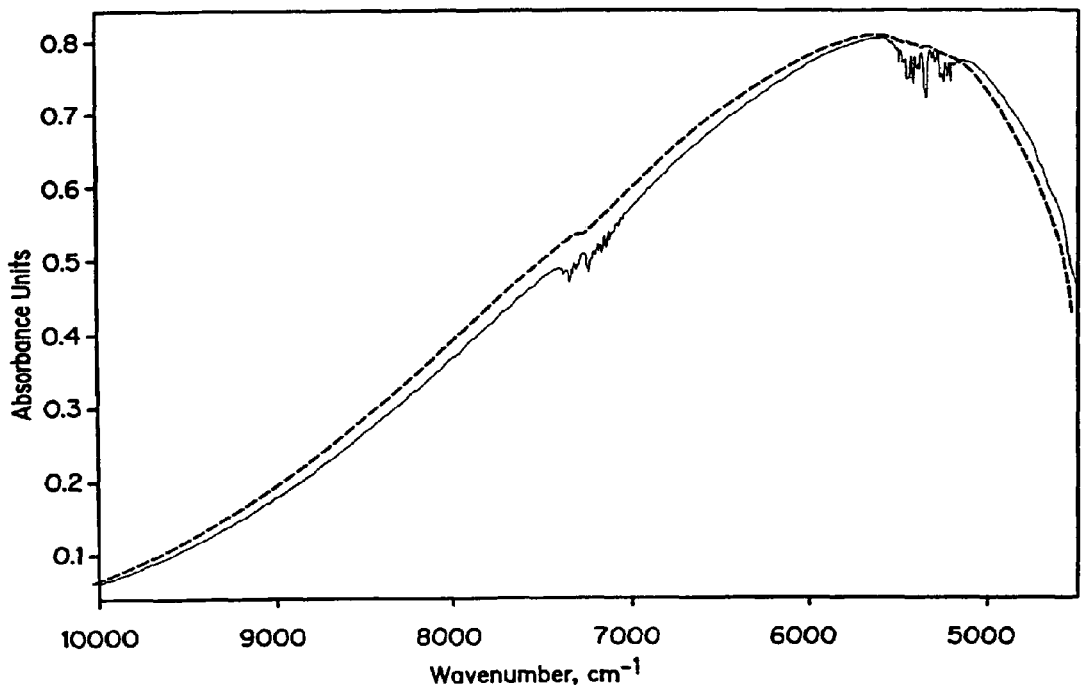
FIG. 20 is background spectra at different humidities.

FIG. 20 shows two background spectra, the upper spectrum being taken under conditions of relatively low humidity and the lower spectrum under relatively high humidity. For the purpose of practicing the present invention, it is not necessary to know or quantitate the magnitudes of these humidities, but only to ensure that the range of humidities included in the training set spans the range that is expected to be encountered in the environment under future measurement conditions. Since measurable differences were observed in these spectra, humidity was probably an influential factor.

Figure 21:
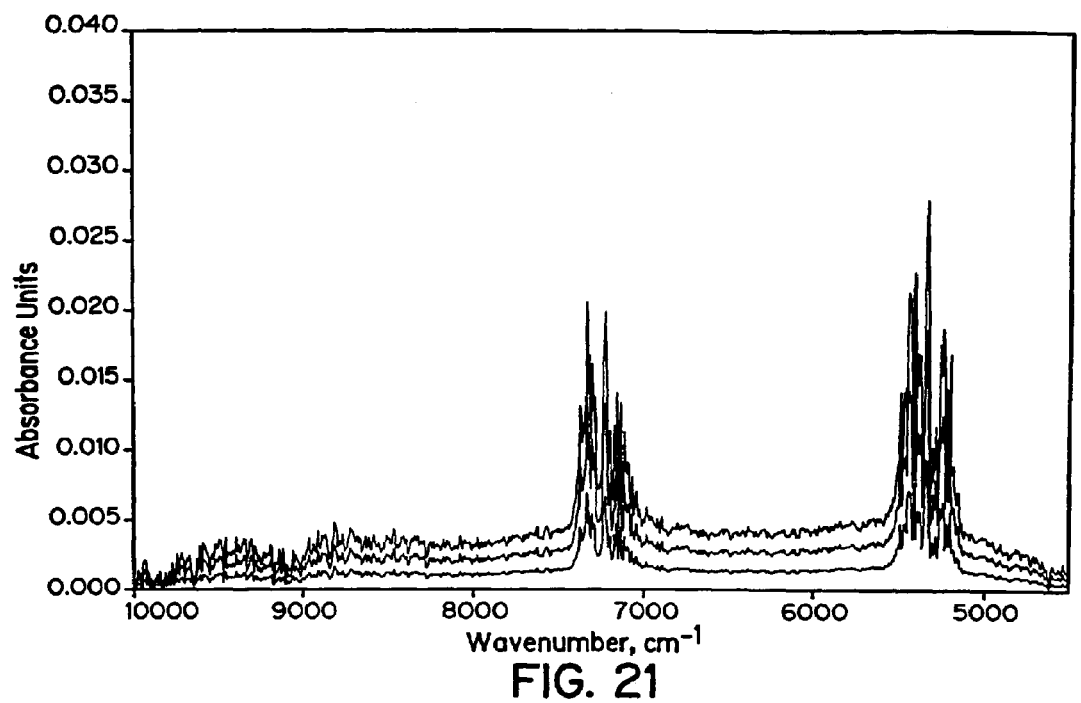
FIG. 21 is superposed NIR spectra of vapor phase water at different generated levels of humidity.

To generate spectra of samples for the training set at various levels of humidity, an initial moisture spectrum was required, typically at a relatively low humidity value. First, a background measurement was taken under very dry conditions after desiccant had remained in the tightly sealed instrument for a period of time. Next, the desiccant inside the instrument was removed to allow the internal humidity to increase to a stable value, and an absorbance spectrum at a higher humidity was measured. As shown in FIG. 21, the acquired moisture spectrum (bottom spectrum) was then used to generate two higher humidity spectra by multiplying the acquired spectrum by factors of 2 and 3.

The spectra used to expand the training set (block 102) were generated mathematically by adding these three moisture spectra to low humidity spectra of samples (taken with the desiccant inside the spectrometer) at 0.00%, 6.00% and 10.00% concentrations in the training set. Model 6.0 was a property model built from this expanded training set using the pretreatment of Model 5.0 (block 104). No outliers were detected (block 106).

Figure 22:
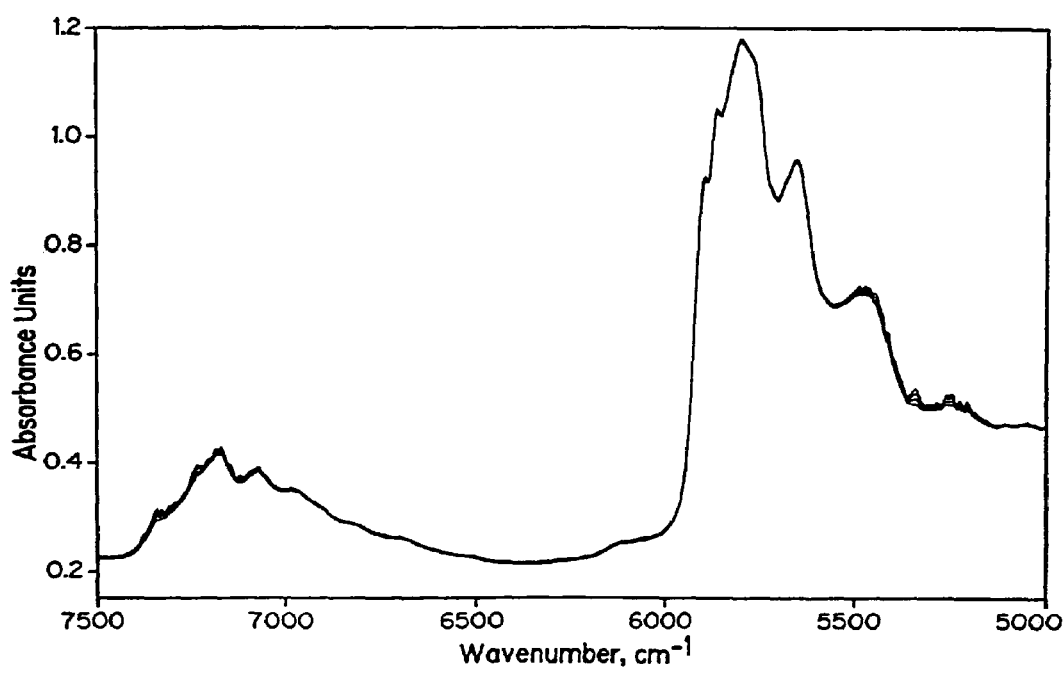
FIG. 22 is superposed NIR spectra of 1.00% squalane in squalene at different generated levels of humidity.

FIG. 22 shows the superposition of the four spectra of a validation sample prepared with 1.00% squalane before and after the mathematical addition of the moisture spectra at multiplicative scaling factors of 1, 2 and 3. When the spectrum with the highest moisture content of FIG. 22 (block 108) was used as a validation set to predict squalane concentration using Model 5.0, the predicted value was 0.67%. Since the absolute value of the residual, 0.33%, was greater than the desired precision value, this residual was statistically significant, and humidity was determined to be an influential factor. It was therefore necessary to revise Model 5.0 (block 90) to compensate for humidity variance. The predicted value from the validation spectrum using Model 6.0 was 1.02%. Since the residual of 0.02% was less than the limit of desired precision, the property was still measurable (block 92) in the presence of variations in humidity.

Example 7

The intensity of the excitation light source of the spectrometer is a potentially influential factor (block 84).

It was found possible to extend a calibration model to compensate for possible variations that can arise over time as a spectroscopic sensor unit ages or, equivalently for the purpose of developing calibration models, for differences in the performance between different spectroscopic sensor units at an arbitrary time. Specifically, it was found that variations in the performance of a small number of components in FT-NIR spectrometers account for most of the variations in the spectra that occur over time or that exist between different spectrometers. Some of these components are the excitation source and the mechanical alignment of the internal optics. Degradation of intensity of the light source or replacement of a light source after failure as well as a shift in the alignment of optical components may cause changes in the instrument responses and, therefore, of the predicted values. Traditionally, correction of such instrument variation would be achieved by re-calibration of each instrument using a remediation update or by adjusting the instrument hardware. The present invention uses a new approach to eliminate the need for frequent remediation updates or to reduce significantly the frequency of re-calibrations and to avoid the need for individual or custom adjustments of instrument-specific calibration transfers on particular equipment.

Figure 23:
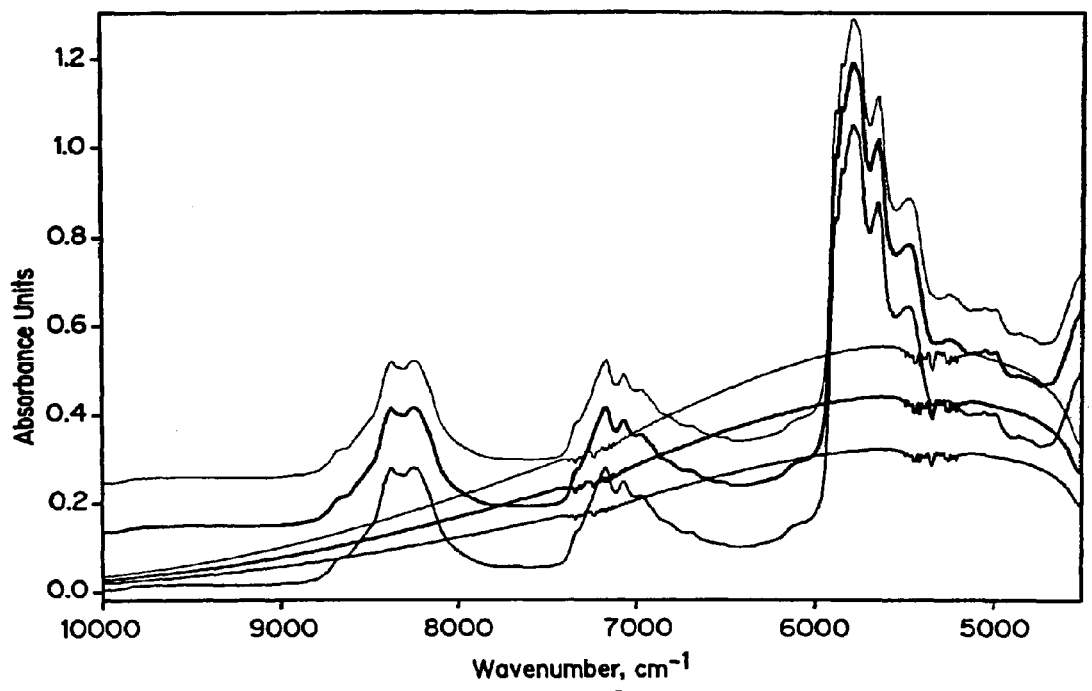
FIG. 23 is superposed NIR background and absorbance spectra of 1.00% squalane in squalene.

FIG. 23 shows the background spectra and the absorbance spectra of a 1.00% squalane validation sample measured by the same FT-NIR instrument but using three different light sources covering a range of performance from a strong, new source to weaker, older sources. The predicted values from these three validation spectra of squalane using Model 6.0 were 1.10%, 1.23% and 1.30%, and RMSEP was 0.226%. Since RMSEP was greater than the limit of desired precision, it was necessary to revise the model to compensate for variance of the excitation source.

Figure 24:
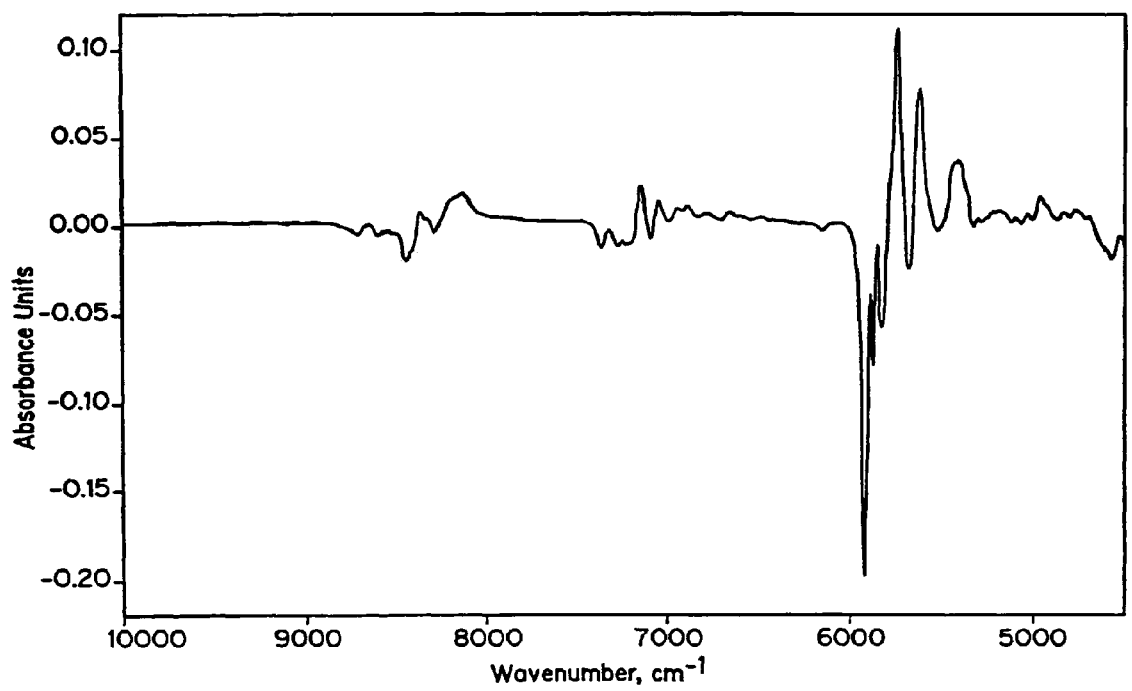
FIG. 24 is superposed transformed spectra after first derivative and vector normalization pretreatment of the FIG. 23 NIR spectra.

The uppermost spectrum in FIG. 23 was obtained using the same light source as that used in Examples 1 through 6, and the two lower spectra were obtained using weaker light sources. Since there were offset, ramp and non-linear relationships between these spectra, pretreatment transformations (block 102) could be used to reduce significantly the corresponding spectral differences. In the present example, a first derivative transformation effectively eliminated the effects from offset and ramp, and vector normalization or multiplicative scattering correction suppressed the intensity variances due to the non-linear effects from different light intensities. For example, first derivative and vector normalization pretreatment of the three squalane FT-NIR spectra of FIG. 23 effectively reduced the differences between spectra as shown in FIG. 24.

Figure 25:
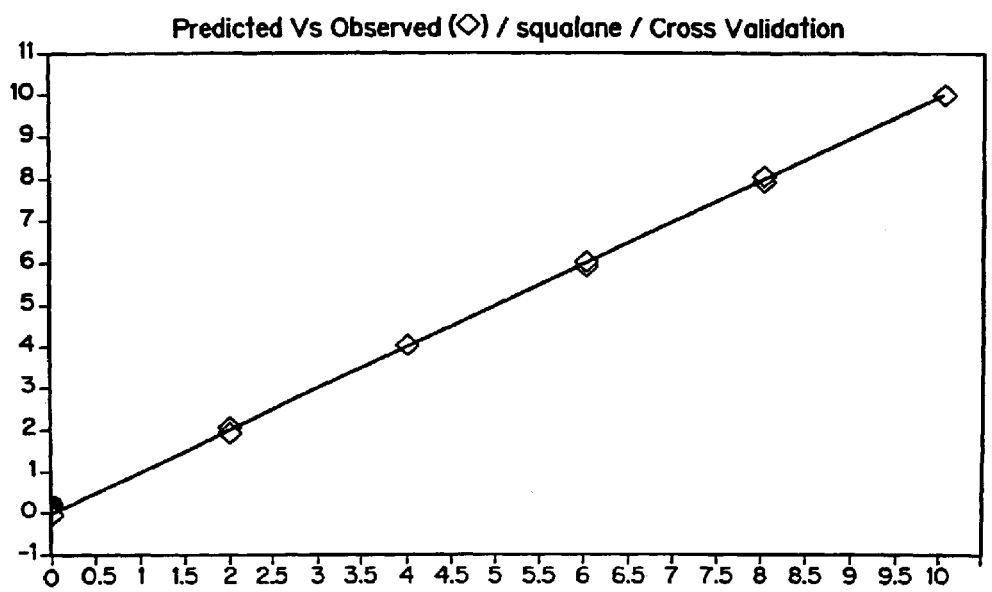
FIG. 25 is predicted versus observed values from the cross-validation of Model 7.0.

Calibration Model 7.0 was a property model built with a refined filter (block 160, FIG. 6) from 5199.2 cm$^{-1}$ to 8797.7 cm$^{-1}$ using pretreatment transformations (block 102) consisting of a first derivative transformation with 17 smoothing points followed by vector normalization. Cross-validation of this calibration model gave values of 99.99 for $R^2$ and 0.042% for RMSECV (block 104) with a rank of 8. The calibration curve from the training set of Model 7.0 is shown in FIG. 25. No outliers were detected (block 106).

The predicted values of concentration from the three validation spectra in FIG. 23 using Model 7.0 were 1.02%, 1.02% and 1.03%. The residuals of the predicted values from these spectra, 0.02%, 0.02% and 0.03%, were each less than the limit of desired precision of 0.10%, so the property was still measurable (block 92) in the presence of variation in the excitation source. Furthermore, this example demonstrates that it was possible to compensate for variations in the intensity of the excitation light source by data pretreatment.

The training set used to develop Model 7.0 is now considered to be a global training set for a single instrument, and Model 7.0 is a single-instrument global property model.

Example 8

Replacement of a fiber optic probe is a potentially influential factor (block 84).

It has been found possible to extend a calibration model to compensate for effects from changing certain hardware components as could occur during instrument maintenance. The most likely hardware components that could be replaced in a FT-NIR system over time include the desiccant, the excitation light source, the laser source, and the fiber optic probe. The method for compensating for the variances from aging desiccant and from decay of the excitation light source was described in Examples 6 and 7. The laser is used to track the wavelength accuracy and will be re-calibrated after replacement of a laser source, so the spectra will not be affected significantly if the laser source is replaced. The current example demonstrates how to compensate for future replacement of a fiber optic probe, which may be needed if it becomes accidentally damaged.

Figure 26:
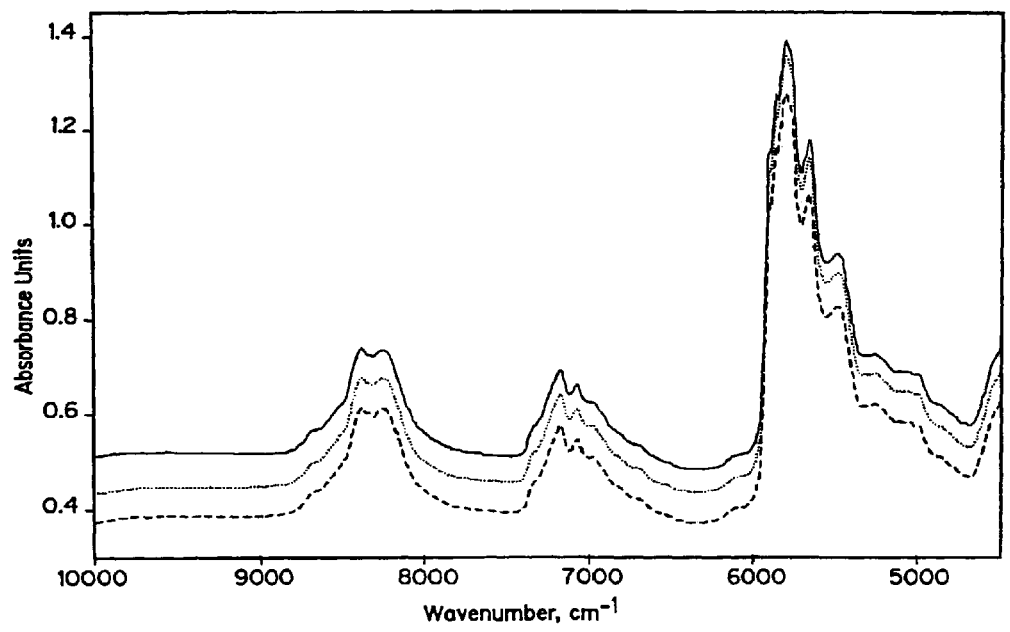
FIG. 26 is superposed NIR spectra of 2.00% squalane in squalene using different fiber optic probes.
Figure 27:
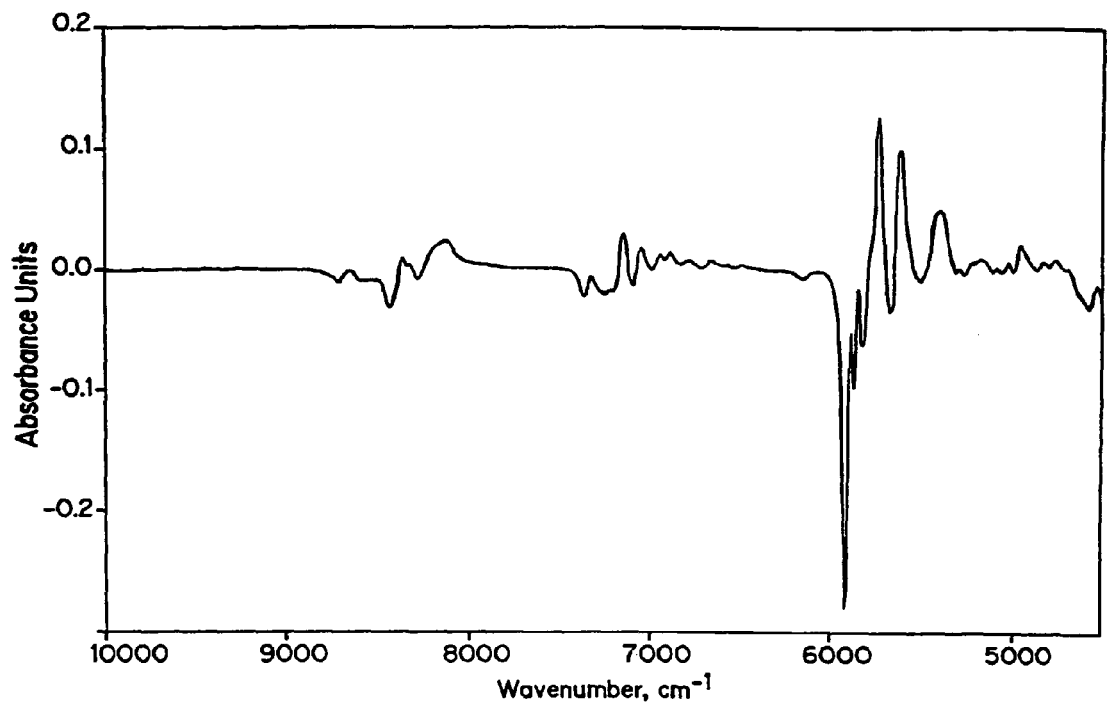
FIG. 27 is superposed transformed spectra after first derivative and vector normalization pretreatment of the FIG. 26 NIR spectra.

FIG. 26 shows the spectra of a 2.00% squalane validation sample measured by the FT-NIR instrument described in Example 1 using three different fiber optic probes selected to cover a range of fiber optic performances (block 86). The lower spectrum was obtained using the same fiber optic probe as used in Examples 1 through 7, while the other two spectra were obtained using two different fiber optic probes. Since measurable differences were observed among these spectra, probe variance is probably an influential factor. The nature of these spectral differences were similar to those in FIG. 23, so data pretreatment as done to correct for light source decay in Example 7, namely first derivative followed by either vector normalization or multiplicative scattering correction (block 102), would also compensate for transmission differences from different fiber optic probes. The effectiveness of first derivative and vector normalization pretreatment on the spectra of FIG. 26 is shown in FIG. 27.

The predicted values of the three validation spectra shown in FIG. 26 using Model 6.0, which was a property model that did not include a first derivative transformation, were 2.02%, 4.22% and 4.39%. The residuals, i.e., 2.22% and 2.39%, from the two additional probes were each greater than the limit of desired precision, and probe variance was determined to be an influential factor (block 88). The corresponding values predicted from Model 7.0, which was a property model that included the first derivative and vector normalization data pretreatment (block 90), were 1.99%, 2.03% and 2.02%. Since the absolute values of the residuals, 0.01%, 0.03% and 0.02%, were each less than the desired precision value, the property was still measurable (block 92). Furthermore, the identified pretreatment effectively eliminated the impact on the predicted results from changing fiber optic probes. Thus, Model 7.0 was confirmed to be a single-instrument global property model and validated for a wider range of instrument variance.

Example 9

The use of different analytical instruments is a potentially influential factor (block 84).

It has been found possible to share a calibration model among two or more NIR instruments without having to develop individual calibrations for each instrument or having to use instrument standardization or calibration transfer methods. To build models that would compensate for variance between instruments, it was necessary to use a set of instruments that are sufficiently similar.

A real spectrum can be considered as the end result obtained from the combination of a hypothetical equipment-independent spectrum with spectral features that arise from equipment-dependent optical parts and alignment, which include the light source, interferometer, mirrors, lens, windows, fiber optics and detectors. Since it is impossible for a manufacturer to produce identical instruments, differences will arise, for example, in the light source intensity, the quality of the optical parts, the alignment of the optical paths, and the response of the detectors.

One method of extending a single-instrument global property model to multiple instruments is to extend the training set with spectra acquired from several calibration samples that span the expected range of the property of interest over a range of measurement conditions as measured by other instrument systems. This method directed to two instruments is illustrated below.

Figure 28:
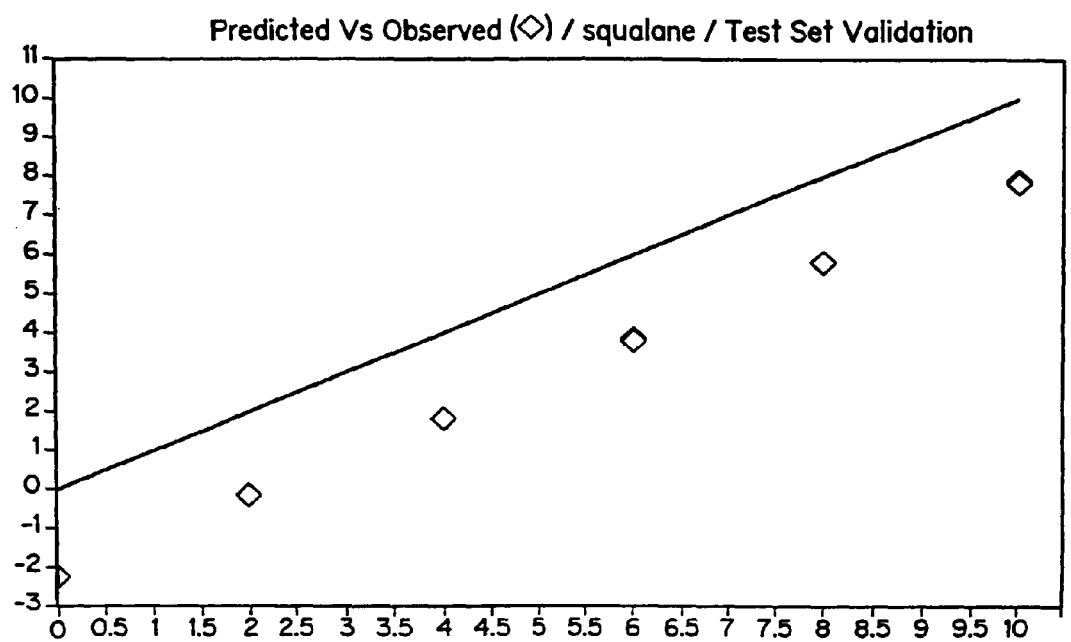
FIG. 28 is predicted versus observed values from the validation of Model 7.0 for different instruments.

For this example, the particular instrument that was used to take measurements in Examples 1 through 8 was labeled as Instrument A, and a second instrument as Instrument B (block 86). When Instrument B was used to measure the samples from the training set of Example 7 taking measurements at four different, random orientations, and when the concentrations were predicted using the single-instrument global property Model 7.0, the RMSEP of the validation set was 2.19% and the predicted values exhibited a systematic offset of about 2.2% as shown in FIG. 28. The observed and predicted values from the validation set are shown in Table 9. Since the RMSEP was greater than the limit of desired precision, it would be necessary to revise Model 7.0 to compensate for variance between instruments (blocks 88 and 90).

For illustrative purposes, the procedure of FIG. 6 was used to build a revised property model from an extended training set (block 167) without using a search algorithm (block 146) to select a refined filter (block 160). The property model and RMSECV of block 140 were obtained from Model 7.0. It was determined that the criteria of blocks 70 and 82 of FIG. 4, and specifically that the desired precision for RMSEP of 0.10%, would be satisfied if the RMSEP of the revised model was not greater than 2 times the RMSECV of Model 7.0, which was about 0.042%, and if the maximum absolute offset was less than 50% of this RMSECV, or less than about 0.021%. These defined the statistical criteria of block 142, which would be used in block 172.

TABLE 9

| Sample No. | Observed (%) | Instrument | Orientation | Predicted (%) | Residual (Obs − Pred) |
|---|---|---|---|---|---|
| 1 | 0 | B | 1 | −2.21 | 2.21 |
| 1 | 0 | B | 2 | −2.24 | 2.24 |
| 1 | 0 | B | 3 | −2.25 | 2.25 |
| 1 | 0 | B | 4 | −2.20 | 2.20 |
| 2 | 2 | B | 1 | −0.20 | 2.20 |
| 2 | 2 | B | 2 | −0.18 | 2.18 |
| 2 | 2 | B | 3 | −0.16 | 2.16 |
| 2 | 2 | B | 4 | −0.19 | 2.19 |
| 3 | 4 | B | 1 | 1.83 | 2.17 |
| 3 | 4 | B | 2 | 1.82 | 2.18 |
| 3 | 4 | B | 3 | 1.81 | 2.19 |
| 3 | 4 | B | 4 | 1.79 | 2.21 |
| 4 | 6 | B | 1 | 3.79 | 2.21 |
| 4 | 6 | B | 2 | 3.85 | 2.15 |
| 4 | 6 | B | 3 | 3.86 | 2.14 |
| 4 | 6 | B | 4 | 3.79 | 2.21 |
| 5 | 8 | B | 1 | 5.82 | 2.18 |
| 5 | 8 | B | 2 | 5.83 | 2.17 |
| 5 | 8 | B | 3 | 5.81 | 2.19 |
| 5 | 8 | B | 4 | 5.79 | 2.21 |
| 6 | 10 | B | 1 | 7.87 | 2.13 |
| 6 | 10 | B | 2 | 7.89 | 2.11 |
| 6 | 10 | B | 3 | 7.82 | 2.18 |
| 6 | 10 | B | 4 | 7.79 | 2.21 |

Figure 29:
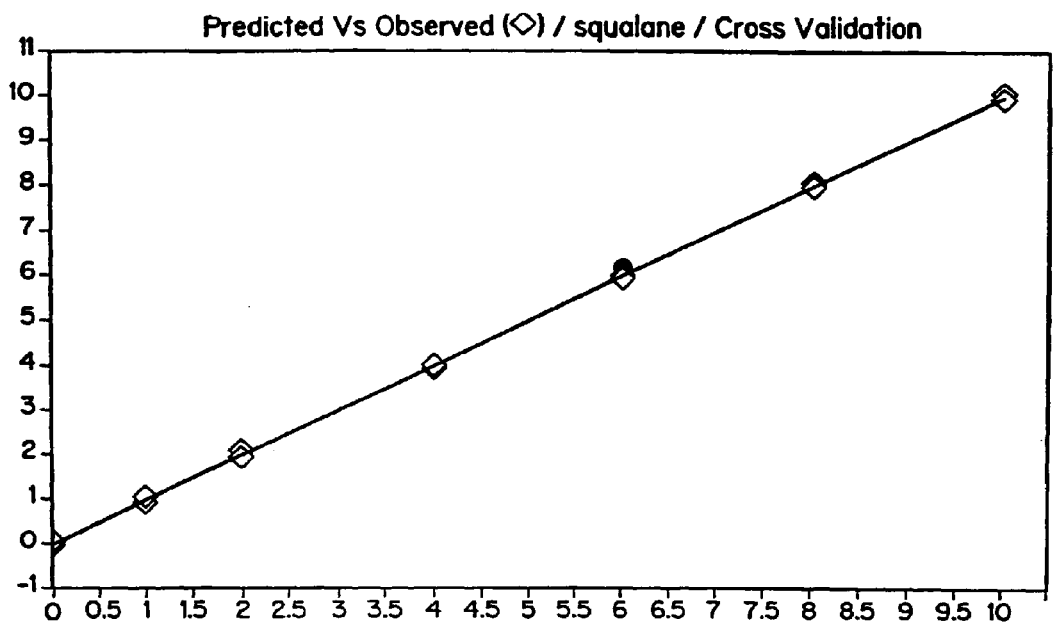
FIG. 29 is predicted versus observed values from the cross-validation of Model 9.0.

Calibration samples with concentrations of 0.00%, 6.00% and 10.00% were then measured by Instrument B and the spectra were appended to the training set that had been used to build Model 7.0 (block 102). Model 9.0 was a property model built from this extended training set (block 104). $R^2$ became 99.99 and RMSECV became 0.039% with a rank of 9. No outliers were detected (block 106). Since the RMSECV was acceptable in block 172 of FIG. 6, the extension was validated in block 174 and instruments A and B were sufficiently similar using the extended training set. The multi-instrument calibration curve for the extended training set of Model 9.0 is shown in FIG. 29.

Figure 30:
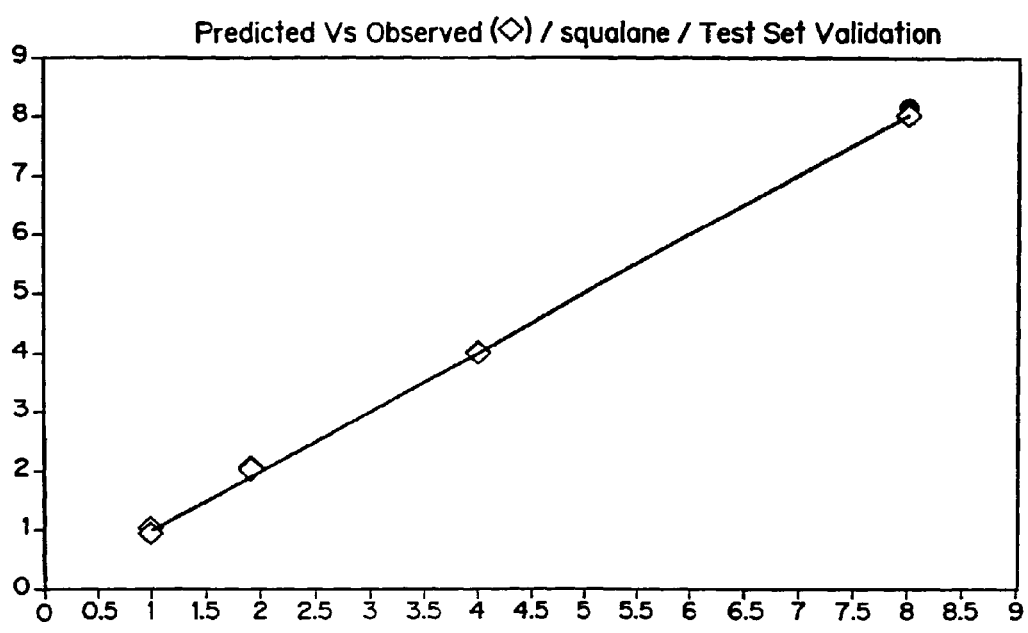
FIG. 30 is predicted versus observed values from the validation of Model 9.0 for Instrument B.

Validation of Model 9.0 using the remaining samples, 1.00%, 2.00%, 4.00% and 8.00%, taking measurements with four different, random orientations using Instrument B to generate the validation set (block 108), gave an RMSEP of 0.040% with a prediction offset of essentially zero as shown in FIG. 30 (block 110). The observed and predicted values from the validation set are given in Table 10. No outliers were detected (block 112). Model 9.0 is a multi-instrument global property model that has been validated for Instruments A and B.

TABLE 10

| Observed (%) | Instrument | Orientation | Predicted (%) | Residual (Obs − Pred) |
|---|---|---|---|---|
| 1.00 | B | 1 | 1.01 | −0.01 |
| 1.00 | B | 2 | 1.00 | 0.00 |
| 1.00 | B | 3 | 1.04 | −0.04 |
| 1.00 | B | 4 | 0.96 | 0.04 |
| 2.00 | B | 1 | 1.98 | 0.02 |
| 2.00 | B | 2 | 2.03 | −0.03 |
| 2.00 | B | 3 | 2.05 | −0.05 |
| 2.00 | B | 4 | 2.02 | −0.02 |
| 4.00 | B | 1 | 4.07 | −0.07 |
| 4.00 | B | 2 | 4.04 | −0.04 |
| 4.00 | B | 3 | 4.04 | −0.04 |
| 4.00 | B | 4 | 4.02 | −0.02 |
| 8.00 | B | 1 | 8.07 | −0.07 |
| 8.00 | B | 2 | 8.05 | −0.05 |
| 8.00 | B | 3 | 8.04 | −0.04 |
| 8.00 | B | 4 | 8.04 | −0.04 |

Example 10

Filter refinement can compensate for variations between instruments. This example demonstrates that predicted values from different instruments can be rendered statistically equivalent using a single property model although the training set for that model does not include instrument-responses from all instruments.

The selection of spectral subregions that may not necessarily minimize RMSECV or RMSEP using the filter refinement procedure of FIG. 6 is sometimes useful in compensating for instrumental variance and can avoid having to take calibration measurements on specific instruments. This technique to compensate for instrument-to-instrument variance is based on two observations. First, a FT-NIR spectrum has a very broad spectral region (4000 $cm^{-1}$ to 12,000 $cm^{-1}$ or 2.5 μm to 0.83 μm), and some narrower subregions within the entire available NIR region are found to be more sensitive to instrumental variance than others. The particular subregions of higher sensitivity are determined, at least in part, by the instrument design and by the properties of specific comprising the spectrometer. As a result, these more sensitive subregions often differ between instrument manufacturers and even between different models from the same manufacturer. Second, there is sometimes an option to choose among different spectral subregions that can be used to build a property model. It has been found that if one or more acceptable spectral subregions is chosen to build the property model using filter refinement, then compensating spectra from other instruments may do need to be added to the training set of the model.

Model 10.0 was a revised property model built by refining the filter for Model 7.0 using OPUS Quant-2 to search for acceptable filters, and changing the spectral region to the refined filter was the pretreatment adjustment of block 108. This chemometric software provided a routine based on three proprietary search algorithms called NIR, General A, and General B. Table 11A summarizes the best trial regions found by OPUS Quant-2 that contained one or two subregions. It is noted that three trial regions were identified as acceptable filters since they produced RMSEP values less than the desired precision of 0.10%, namely trial regions 3, 4, and 6. According to previously described Criterion A, trial region 6 was most preferred. According to Criterion B, however, trial region 3 was preferred over trial region 6 because it had a smaller number of subregions. Since application of Criterion B resulted in a single trial region, Criterion C was not used. Hence, the refined filter (block 160, FIG. 6) for Model 10.0 was selected according to Criterion B to be trial region 3, which was the single subregion from 4597.5 $cm^{-1}$ to 9395.6 $cm^{-1}$.

Figure 31:
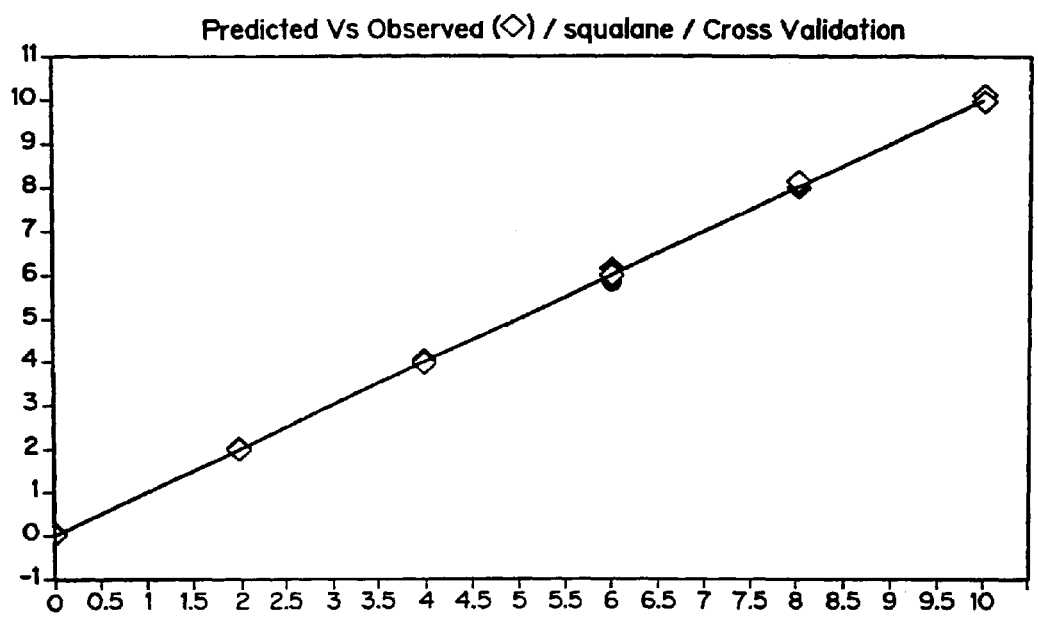
FIG. 31 is predicted versus observed values from the cross-validation of Model 10.0.

For illustrative purposes, an alternative development of Model 10.0 was then considered. Since the RMSEP of trial region 6 was much less than the limit of desired precision, there was an opportunity to improve significantly the level of predictability of the model. Suppose that during consultation with the customer, it was decided to define an improved level of predictability such that RMSEP would be less than 0.05%, thereby redefining the objectives of block 70 in FIG. 4. Then, according to the previously described procedure for filter refinement, and using first derivative (21 smoothing points) and vector normalization pretreatment (block 102), the refined filter (block 160, FIG. 6) for Model 10.0 was selected to be trial region 6, which was the composite subregion from 4597.5 $cm^{-1}$ to 6398.7 $cm^{-1}$ and 7594.4 $cm^{-1}$ to 8797.7 $cm^{-1}$. Cross-validation of Model 10.0 gave 99.99 for $R^2$ and 0.046% for RMSECV (block 104) with a rank of 8. The prediction offset was essentially zero, and no outliers were detected (block 106). The cross-validation curve for Model 10.0 is reproduced in FIG. 31.

TABLE 11A

| Trial Region | OPUS Procedure | No. Sub-Regions | Subregion 1 | Subregion 2 | Rank | RMSEP | RMSECV |
|---|---|---|---|---|---|---|---|
| 1 | NIR | 1 | 5349.6-6101.7 | | 7 | 0.118 | 0.058 |
| 2 | NIR | 2 | 4597.5-6101.7 | 7497.9-9993.4 | 7 | 0.298 | 0.052 |
| 3 | General A | 1 | 4597.5-9395.6 | | 9 | 0.0734 | 0.041 |
| 4 | General A | 2 | 4597.5-6996.5 | 8793.9-9993.4 | 7 | 0.0527 | 0.055 |
| 5 | General B | 1 | 4597.5-6398.7 | | 10 | 0.143 | 0.051 |
| 6 | General B | 2 | 4597.5-6398.7 | 7594.4-8797.7 | 8 | 0.0396 | 0.046 |

Figure 32:
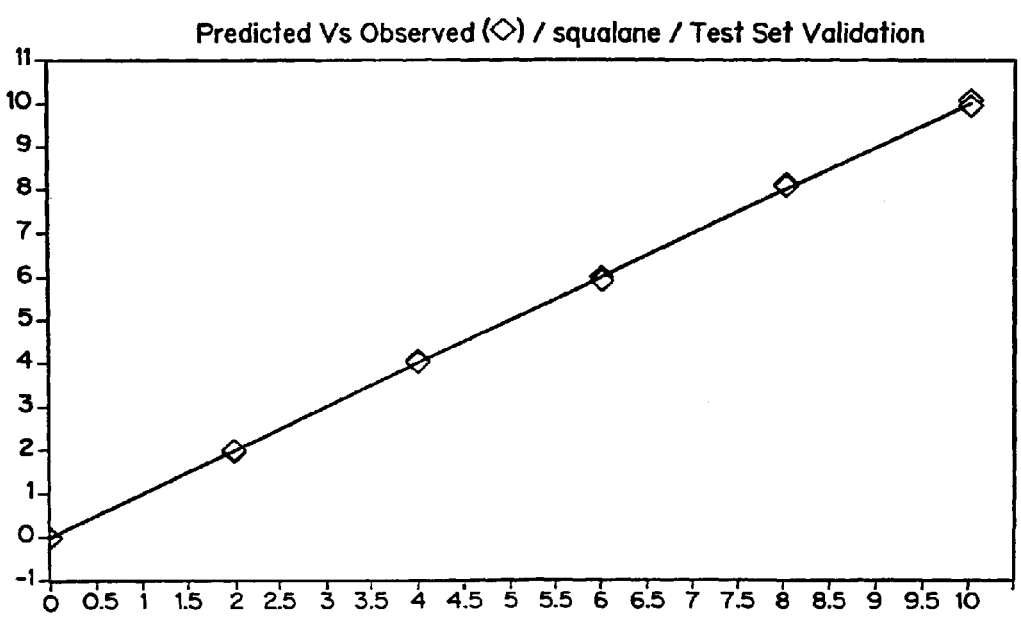
FIG. 32 is predicted versus observed values from the validation of Model 10.0 for Instrument B.

Validation of Model 10.0 using calibration samples and measurement conditions of the training set of Model 7.0 and using instrument responses measured by Instrument B generated a validation set (block 108) that produced RMSEP of 0.0396% (block 110) without a significant prediction offset as shown in FIG. 32. No outliers were detected (block 112). The observed and predicted values from the validation set are shown in Table 11 B. These results demonstrated an acceptable level of precision based on the model generated for Instrument A but used with Instrument B. Therefore, under these measurement conditions it was possible to share a single property model with multiple FT-NIR instruments. Model 10.0 was a global property model for Instruments A and B, and this model was preferred over Model 9.0 since the training set for Model 10.0 did not require training measurements from Instrument B. Model 10.0 was ready for installation in block 114 of FIG. 5.

TABLE 11B

| Sample No. | Observed (%) | Instrument | Orientation | Predicted (%) | Residual (Obs – Pred) |
|---|---|---|---|---|---|
| 1 | 0.00 | B | 1 | 0.03 | −0.03 |
| 1 | 0.00 | B | 2 | −0.03 | 0.03 |
| 1 | 0.00 | B | 3 | −0.05 | 0.05 |
| 1 | 0.00 | B | 4 | −0.03 | 0.03 |
| 2 | 2.00 | B | 1 | 1.95 | 0.05 |
| 2 | 2.00 | B | 2 | 2.00 | 0.00 |
| 2 | 2.00 | B | 3 | 2.02 | −0.02 |
| 2 | 2.00 | B | 4 | 1.99 | 0.01 |
| 3 | 4.00 | B | 1 | 4.04 | −0.04 |
| 3 | 4.00 | B | 2 | 4.00 | 0.00 |
| 3 | 4.00 | B | 3 | 3.99 | 0.01 |
| 3 | 4.00 | B | 4 | 3.97 | 0.03 |
| 4 | 6.00 | B | 1 | 5.94 | 0.06 |
| 4 | 6.00 | B | 2 | 5.96 | 0.04 |
| 4 | 6.00 | B | 3 | 5.95 | 0.05 |
| 4 | 6.00 | B | 4 | 5.91 | 0.09 |
| 5 | 8.00 | B | 1 | 8.02 | −0.02 |
| 5 | 8.00 | B | 2 | 7.99 | 0.01 |
| 5 | 8.00 | B | 3 | 7.96 | 0.04 |
| 5 | 8.00 | B | 4 | 7.96 | 0.04 |
| 6 | 10.00 | B | 1 | 9.99 | 0.01 |
| 6 | 10.00 | B | 2 | 9.98 | 0.02 |
| 6 | 10.00 | B | 3 | 9.94 | 0.06 |
| 6 | 10.00 | B | 4 | 9.94 | 0.06 |

Example 11

This example illustrates the method of developing several property models for a material after a feasibility study had been completed (block 100, FIG. 5) and an effectively comprehensive set of influential factors had been identified along with appropriate methods of data pretreatment. The method (block 70, FIG. 4) was defined as FT-NIR using the instrument and sample presentation device shown in FIG. 33. The objectives (block 70, FIG. 4) included measurements by non-skilled operators of the total oil, oleic and linolenic contents in canola seeds with measurement precisions characterized by RMSEP values less than 0.6% for each property as predicted by multi-instrument global property models.

A variety of canola was selected which had been bred to contain oleic acid with a target specification greater than 70% (present as the triglyceride and relative to the total oil content) and linolenic acid with a target specification less than 3.5% (present as the triglyceride and relative to the total oil content). The expected ranges of block 72 were 63% to 75% for oleic content, 2.5% to 7.8% for linolenic content, and 44% to 51% for total oil content. The observed values of total oil content were determined by extraction using a solvent-based extraction method, and those for oleic and linolenic oil content were obtained by analyzing the extracted oil using gas chromatography. The method for determining oil content was AOCS Official Method Am 2-93 (updated 1995). Oleic and linolenic oil content was determined using AOCS Official Method Ce 1-62 (revised 1990). All component concentrations were adjusted to a dry basis by subtracting the actual moisture content in each sample from the total sample weight.

The calibration set of block 74 comprised 45 canola samples that had been selected to cover the expected ranges of concentrations for total oil, oleic oil and linolenic oil, and to span the expected range of secondary material characteristics. The canola seeds typically had diameters ranging from about 1.5 to 2.5-mm. The grain had been partially cleaned by sieving as is commonly done as part of visual grading used to assess grain quality for grain transactions. A natural selection of foreign matter, called dockage in the grain industry, remained in the samples in amounts up to about two percent by weight.

Figure 33:
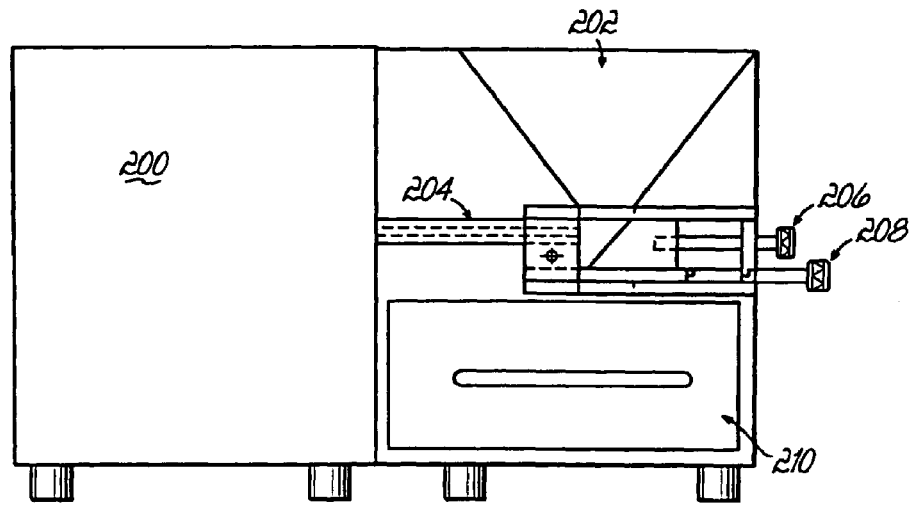
FIG. 33 is a schematic diagram of a flow-through sample presentation system attached to a FT-NIR spectrometer.

For non-destructive FT-NIR measurements of whole grain, FIG. 33 shows the flow-through sample presentation device, which was comprised of the funnel 202 for presenting grain samples, the flow rate controller 206 for the grain sample, the funnel gate 208 for initiating sample flow, and the grain collector 210, and attached to the FT-NIR instrument 200 equipped with fiber optic probe 204. This device was designed to provide a significantly larger sampling area for data acquisition than would be obtained by using a similarly configured fiber optic probe to measure a stationary sample of grain.

FT-NIR measurements were done by first pouring about 250 grams of canola into the funnel 202, the funnel having an inner cross-section of 120 mm$^2$, and then opening the funnel gate 208 half-way to permit the grain to start flowing into grain collector 210. The flow rate was set at the flow rate controller 206 to pass about 10 grams of canola per second. The fiber optic probe 204 was engaged by pressing a button on the probe trigger about one to two seconds after the grain had started to flow to initiate data collection of 40 spectra at a scanning speed of 20 kHz and about 2 scans per second. The spectra were pre-processed by averaging in interferogram mode, converting to single-scan mode by fast Fourier Transform, and then converting to an averaged absorbance spectrum for spectroscopic analysis. The averaged absorbance spectrum was evaluated by OPUS to predict values of total oil content, oleic oil content, linolenic oil content and the Mahalanobis distances from each property model.

To develop the training sets for the property models (block 102, FIG. 5), each of the 45 samples of the calibration set was first measured 3 times at ambient temperature to generate repeated measures of the instrument response. Table 12 lists five samples for the calibration set that were then used to generate additional calibration spectra for an extended training set which, in combination with data pretreatment, would compensate for an effectively comprehensive range of influential factors, including temperature, humidity, light source, fiber probe and instrument. These five calibration samples spanned the expected ranges of concentrations of total oil, oleic oil and linolenic oil contents as determined by solvent extraction and gas chromatography. It was demonstrated that the use of different sample presentation devices of the type shown in FIG. 33 was not an influential factor for the properties of interest.

TABLE 12

| Sample Label | % Oleic | % Linolenic | % Oil |
|---|---|---|---|
| S1 | 63.00 | 7.82 | 46.30 |
| S2 | 73.89 | 3.22 | 51.20 |
| S3 | 75.72 | 2.58 | 48.10 |
| S4 | 74.25 | 2.67 | 43.80 |
| S5 | 69.62 | 3.57 | 38.68 |

Temperature compensation was included in the calibration models to accommodate sample measurements over a wide range of temperatures, specifically from about −60° C. to about 50° C. This was accomplished by first cooling samples S1 to S5 in a freezer at −70° C., bringing the samples to the spectrometer area in contact with dry ice, and then measuring the samples as they warmed slightly during the flow-through sample presentation. These five samples were then heated in an oven at 60° C. and measured as they cooled slightly during flow-through sample presentation. It is conceptually important to note that it is not necessary to know the precise values of sample temperatures while they were warming or cooling during data acquisition in order to build an acceptable multivariate calibration model. Since the NIR spectra of the calibration training set included measurements at various temperatures that spanned the expected range, the PLS procedure generated multivariate models that compensated for non-quantified temperature variance within the range of temperatures used in the training set.

Humidity compensation was included in the models using the technique of Example 6 by generating spectra with a range of humidities for three canola samples, S1, S3, and S5. The models thus compensated for non-quantified humidity variance.

Figure 34:
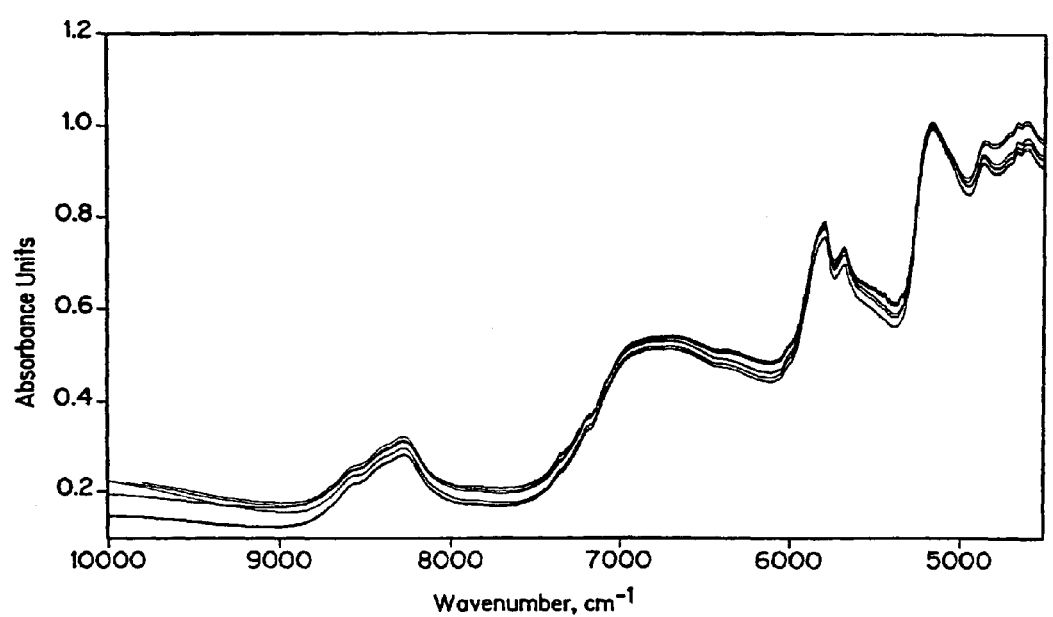
FIG. 34 is superposed NIR spectra of representative seed samples of a variety of canola.

To optimize the filter and validate the calibration models, these samples were measured by 4 additional Bruker MATRIX Model F FT-NIR spectrometers 200. Two spectra of each of the five samples of Table 12 measured by two of the spectrometers 200 were included in the extended training set, with the remaining spectra used to create a validation set for the models. The models thus compensated for non-quantified instrument variance. Some representative spectra of the canola measured by one spectrometer are shown in FIG. 34.

Figure 35:
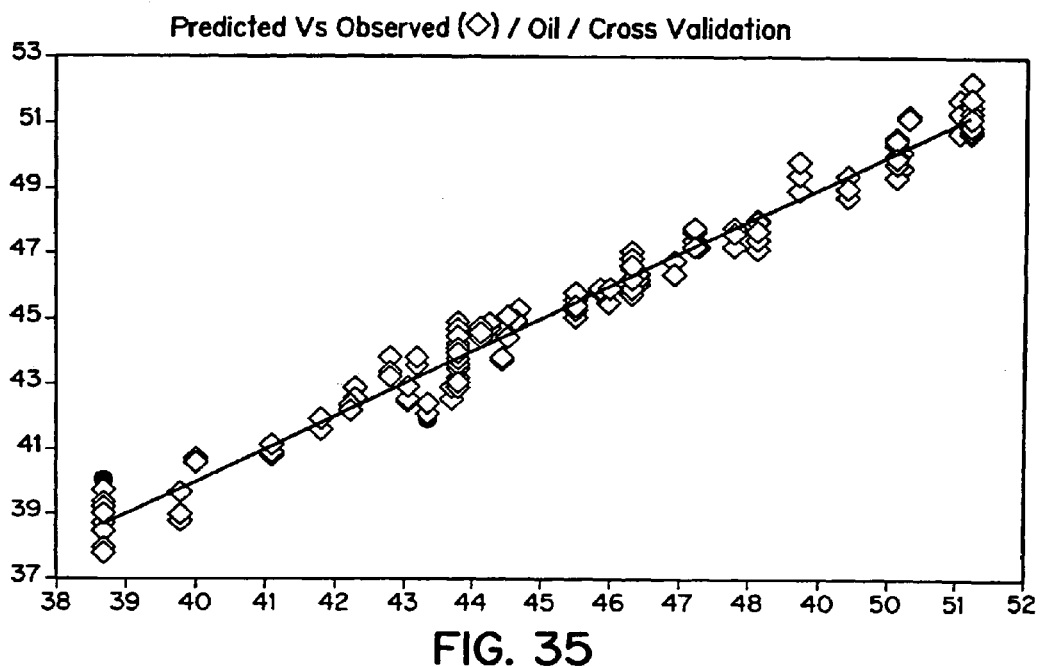
FIG. 35 is predicted versus observed values from the cross-validation of Model 11.0.

Model 11.0 was multi-instrument global a property model (block 104, FIG. 5) constructed to predict total oil content using a refined filter (block 160, FIG. 6) from 4597.5 $cm^{-1}$ to 7501.8 $cm^{-1}$. Data pretreatment also included a first-derivative transformation with 13 smoothing points followed by vector normalization. Cross-validation of Model 11.0 gave 97.89 for $R^2$ and 0.527% for RMSECV with a rank of 9 for the concentration range from 38.68% to 51.20% total oil. The calibration curve of Model 11.0 is shown in FIG. 35. The observed and predicted values from the extended training set of Model 11.0 for total oil are in Table 13.

TABLE 13

| Spectrum | Sample | Observed (%) | Predicted (%) | Residual (Obs − Pred) |
|---|---|---|---|---|
| 1 | 1 | 43.71 | 42.55 | 1.16 |
| 2 | 1 | 43.71 | 42.46 | 1.25 |
| 3 | 1 | 43.71 | 42.87 | 0.84 |
| 4 | 2 | 43.80 | 44.66 | −0.86 |
| 5 | 2 | 43.80 | 44.51 | −0.71 |
| 6 | 2 | 43.80 | 44.89 | −1.09 |
| 7 | 4 | 39.78 | 38.78 | 1.00 |
| 8 | 4 | 39.78 | 38.96 | 0.82 |
| 9 | 4 | 39.78 | 39.67 | 0.11 |
| 10 | 5 | 38.68 | 38.50 | 0.18 |
| 11 | 5 | 38.68 | 40.06 | −1.38 |
| 12 | 5 | 38.68 | 39.60 | −0.92 |
| 13 | 7 | 44.25 | 44.70 | −0.45 |
| 14 | 7 | 44.25 | 44.86 | −0.61 |
| 15 | 7 | 44.25 | 44.89 | −0.64 |
| 16 | 8 | 43.35 | 41.89 | 1.46 |
| 17 | 8 | 43.35 | 42.04 | 1.31 |
| 18 | 8 | 43.35 | 42.36 | 0.99 |
| 19 | 9 | 43.23 | 43.70 | −0.47 |
| 20 | 9 | 43.23 | 43.58 | −0.35 |
| 21 | 9 | 43.23 | 43.55 | −0.32 |
| 22 | 10 | 45.86 | 45.79 | 0.07 |
| 23 | 10 | 45.86 | 45.91 | −0.05 |
| 24 | 10 | 45.86 | 45.75 | 0.11 |
| 25 | 11 | 50.30 | 51.26 | −0.96 |
| 26 | 11 | 50.30 | 51.15 | −0.85 |
| 27 | 11 | 50.30 | 51.08 | −0.78 |
| 28 | 12 | 48.69 | 48.91 | −0.22 |
| 29 | 12 | 48.69 | 49.44 | −0.75 |
| 30 | 12 | 48.69 | 49.78 | −1.09 |
| 31 | 13 | 44.12 | 44.75 | −0.63 |
| 32 | 13 | 44.12 | 44.42 | −0.30 |
| 33 | 13 | 44.12 | 44.57 | −0.45 |
| 34 | 14 | 42.27 | 42.64 | −0.37 |
| 35 | 14 | 42.27 | 42.87 | −0.60 |
| 36 | 14 | 42.27 | 42.55 | −0.28 |
| 37 | 15 | 44.66 | 45.27 | −0.61 |
| 38 | 15 | 44.66 | 44.88 | −0.22 |
| 39 | 15 | 44.66 | 45.24 | −0.58 |
| 40 | 16 | 47.22 | 47.13 | 0.09 |
| 41 | 16 | 47.22 | 47.65 | −0.43 |
| 42 | 16 | 47.22 | 47.42 | −0.20 |
| 43 | 17 | 43.06 | 42.43 | 0.63 |
| 44 | 17 | 43.06 | 42.47 | 0.59 |
| 45 | 17 | 43.06 | 42.86 | 0.20 |
| 46 | 18 | 47.27 | 47.27 | 0.00 |
| 47 | 18 | 47.27 | 47.23 | 0.04 |
| 48 | 18 | 47.27 | 47.13 | 0.14 |
| 49 | 19 | 44.45 | 43.71 | 0.74 |
| 50 | 19 | 44.45 | 43.76 | 0.69 |
| 51 | 19 | 44.45 | 43.81 | 0.64 |
| 52 | 20 | 45.99 | 45.53 | 0.46 |
| 53 | 20 | 45.99 | 45.49 | 0.50 |
| 54 | 20 | 45.99 | 45.89 | 0.10 |
| 55 | 21 | 50.19 | 49.66 | 0.53 |
| 56 | 21 | 50.19 | 49.59 | 0.60 |
| 57 | 21 | 50.19 | 50.08 | 0.11 |
| 58 | 22 | 41.80 | 41.55 | 0.25 |
| 59 | 22 | 41.80 | 41.87 | −0.07 |
| 60 | 22 | 41.80 | 41.86 | −0.06 |
| 61 | 23 | 43.18 | 43.61 | −0.43 |
| 62 | 23 | 43.18 | 43.52 | −0.34 |

TABLE 13-continued

| Spectrum | Sample | Observed (%) | Predicted (%) | Residual (Obs − Pred) |
|---|---|---|---|---|
| 63 | 23 | 43.18 | 43.81 | −0.63 |
| 64 | 24 | 46.40 | 46.13 | 0.27 |
| 65 | 24 | 46.40 | 46.35 | 0.05 |
| 66 | 24 | 46.40 | 46.03 | 0.37 |
| 67 | 25 | 46.30 | 46.71 | −0.41 |
| 68 | 25 | 46.30 | 47.03 | −0.73 |
| 69 | 25 | 46.30 | 46.58 | −0.28 |
| 70 | 26 | 51.00 | 51.70 | −0.70 |
| 71 | 26 | 51.00 | 51.25 | −0.25 |
| 72 | 26 | 51.00 | 50.70 | 0.30 |
| 73 | 27 | 50.10 | 50.03 | 0.07 |
| 74 | 27 | 50.10 | 50.54 | −0.44 |
| 75 | 27 | 50.10 | 49.96 | 0.14 |
| 76 | 28 | 51.20 | 50.97 | 0.23 |
| 77 | 28 | 51.20 | 51.14 | 0.06 |
| 78 | 28 | 51.20 | 50.70 | 0.50 |
| 79 | 29 | 48.10 | 47.65 | 0.45 |
| 80 | 29 | 48.10 | 47.88 | 0.22 |
| 81 | 29 | 48.10 | 47.47 | 0.63 |
| 82 | 30 | 45.50 | 45.59 | −0.09 |
| 83 | 30 | 45.50 | 45.26 | 0.24 |
| 84 | 30 | 45.50 | 45.50 | 0.00 |
| 85 | 31 | 46.90 | 46.62 | 0.28 |
| 86 | 31 | 46.90 | 46.70 | 0.20 |
| 87 | 31 | 46.90 | 46.35 | 0.55 |
| 88 | 32 | 42.80 | 43.83 | −1.03 |
| 89 | 32 | 42.80 | 43.25 | −0.45 |
| 90 | 32 | 42.80 | 43.34 | −0.54 |
| 91 | 33 | 42.20 | 42.37 | −0.17 |
| 92 | 33 | 42.20 | 42.08 | 0.12 |
| 93 | 33 | 42.20 | 42.16 | 0.04 |
| 94 | 34 | 47.20 | 47.28 | −0.08 |
| 95 | 34 | 47.20 | 47.75 | −0.55 |
| 96 | 34 | 47.20 | 47.19 | 0.01 |
| 97 | 35 | 47.80 | 47.80 | 0.00 |
| 98 | 35 | 47.80 | 47.13 | 0.67 |
| 99 | 35 | 47.80 | 47.61 | 0.19 |
| 100 | 36 | 43.80 | 43.18 | 0.62 |
| 101 | 36 | 43.80 | 43.55 | 0.25 |
| 102 | 36 | 43.80 | 43.84 | −0.04 |
| 103 | 37 | 43.80 | 43.52 | 0.28 |
| 104 | 37 | 43.80 | 43.70 | 0.10 |
| 105 | 37 | 43.80 | 43.92 | −0.12 |
| 106 | 38 | 44.50 | 45.05 | −0.55 |
| 107 | 38 | 44.50 | 44.46 | 0.04 |
| 108 | 39 | 49.40 | 49.35 | 0.05 |
| 109 | 39 | 49.40 | 48.75 | 0.65 |
| 110 | 39 | 49.40 | 48.96 | 0.44 |
| 111 | 41 | 40.00 | 40.67 | −0.67 |
| 112 | 41 | 40.00 | 40.70 | −0.70 |
| 113 | 41 | 40.00 | 40.60 | −0.60 |
| 114 | 42 | 41.10 | 40.75 | 0.35 |
| 115 | 42 | 41.10 | 40.94 | 0.16 |
| 116 | 42 | 41.10 | 41.09 | 0.01 |
| 117 | 43 | 50.10 | 50.45 | −0.35 |
| 118 | 43 | 50.10 | 50.29 | −0.19 |
| 119 | 43 | 50.10 | 50.43 | −0.33 |
| 120 | 44 | 45.50 | 45.01 | 0.49 |
| 121 | 44 | 45.50 | 45.38 | 0.12 |
| 122 | 44 | 45.50 | 45.75 | −0.25 |
| 123 | 28 | 51.20 | 50.70 | 0.50 |
| 124 | 28 | 51.20 | 50.89 | 0.31 |
| 125 | 28 | 51.20 | 50.86 | 0.34 |
| 126 | 29 | 48.10 | 47.54 | 0.56 |
| 127 | 29 | 48.10 | 47.31 | 0.79 |
| 128 | 29 | 48.10 | 48.01 | 0.09 |
| 129 | 27 | 50.10 | 50.01 | 0.09 |
| 130 | 27 | 50.10 | 49.99 | 0.11 |
| 131 | 27 | 50.10 | 49.32 | 0.78 |
| 132 | 2 | 43.80 | 44.26 | −0.46 |
| 133 | 2 | 43.80 | 44.70 | −0.90 |
| 134 | 2 | 43.80 | 44.40 | −0.60 |
| 135 | 5 | 38.68 | 39.43 | −0.75 |
| 136 | 5 | 38.68 | 39.31 | −0.63 |
| 137 | 5 | 38.68 | 39.36 | −0.68 |
| 138 | 25 | 46.30 | 46.11 | 0.19 |
| 139 | 25 | 46.30 | 46.17 | 0.13 |
| 140 | 25 | 46.30 | 46.11 | 0.19 |
| 141 | 28 | 51.20 | 51.64 | −0.44 |
| 142 | 28 | 51.20 | 51.51 | −0.31 |
| 143 | 28 | 51.20 | 51.60 | −0.40 |
| 144 | 29 | 48.10 | 47.51 | 0.59 |
| 145 | 29 | 48.10 | 47.91 | 0.19 |
| 146 | 29 | 48.10 | 47.94 | 0.16 |
| 147 | 27 | 50.10 | 49.75 | 0.35 |
| 148 | 27 | 50.10 | 50.00 | 0.10 |
| 149 | 27 | 50.10 | 49.93 | 0.17 |
| 150 | 2 | 43.80 | 42.85 | 0.95 |
| 151 | 2 | 43.80 | 43.50 | 0.30 |
| 152 | 2 | 43.80 | 43.44 | 0.36 |
| 153 | 5 | 38.68 | 39.09 | −0.41 |
| 154 | 5 | 38.68 | 39.06 | −0.38 |
| 155 | 5 | 38.68 | 38.73 | −0.05 |
| 156 | 25 | 46.30 | 46.33 | −0.03 |
| 157 | 25 | 46.30 | 46.76 | −0.46 |
| 158 | 25 | 46.30 | 46.13 | 0.17 |
| 159 | 2 | 43.80 | 43.57 | 0.23 |
| 160 | 2 | 43.80 | 44.06 | −0.26 |
| 161 | 5 | 38.68 | 39.34 | −0.66 |
| 162 | 5 | 38.68 | 39.72 | −1.04 |
| 163 | 25 | 46.30 | 46.53 | −0.23 |
| 164 | 25 | 46.30 | 45.75 | 0.55 |
| 165 | 28 | 51.20 | 51.25 | −0.05 |
| 166 | 28 | 51.20 | 50.86 | 0.34 |
| 167 | 29 | 48.10 | 47.09 | 1.01 |
| 168 | 2 | 43.80 | 43.64 | 0.16 |
| 169 | 2 | 43.80 | 43.07 | 0.73 |
| 170 | 5 | 38.68 | 37.93 | 0.75 |
| 171 | 5 | 38.68 | 37.77 | 0.91 |
| 172 | 25 | 46.30 | 46.06 | 0.24 |
| 173 | 25 | 46.30 | 45.69 | 0.61 |
| 174 | 28 | 51.20 | 52.25 | −1.05 |
| 175 | 28 | 51.20 | 50.87 | 0.33 |
| 176 | 29 | 48.10 | 47.31 | 0.79 |
| 177 | 29 | 48.10 | 47.73 | 0.37 |
| 178 | 2 | 43.80 | 44.04 | −0.24 |
| 179 | 2 | 43.80 | 43.78 | 0.02 |
| 180 | 5 | 38.68 | 39.36 | −0.68 |
| 181 | 5 | 38.68 | 39.18 | −0.50 |
| 182 | 25 | 46.30 | 45.87 | 0.43 |
| 183 | 25 | 46.30 | 46.47 | −0.17 |
| 184 | 28 | 51.20 | 51.50 | −0.30 |
| 185 | 28 | 51.20 | 51.30 | −0.10 |
| 186 | 29 | 48.10 | 47.15 | 0.95 |
| 187 | 29 | 48.10 | 47.88 | 0.22 |
| 188 | 2 | 43.80 | 43.72 | 0.08 |
| 189 | 2 | 43.80 | 43.91 | −0.11 |
| 190 | 5 | 38.68 | 39.00 | −0.32 |
| 191 | 5 | 38.68 | 38.47 | 0.21 |
| 192 | 25 | 46.30 | 46.18 | 0.12 |
| 193 | 25 | 46.30 | 46.58 | −0.28 |
| 194 | 28 | 51.20 | 51.08 | 0.12 |
| 195 | 28 | 51.20 | 51.68 | −0.48 |
| 196 | 29 | 48.10 | 47.38 | 0.72 |
| 197 | 29 | 48.10 | 47.67 | 0.43 |

Figure 36:
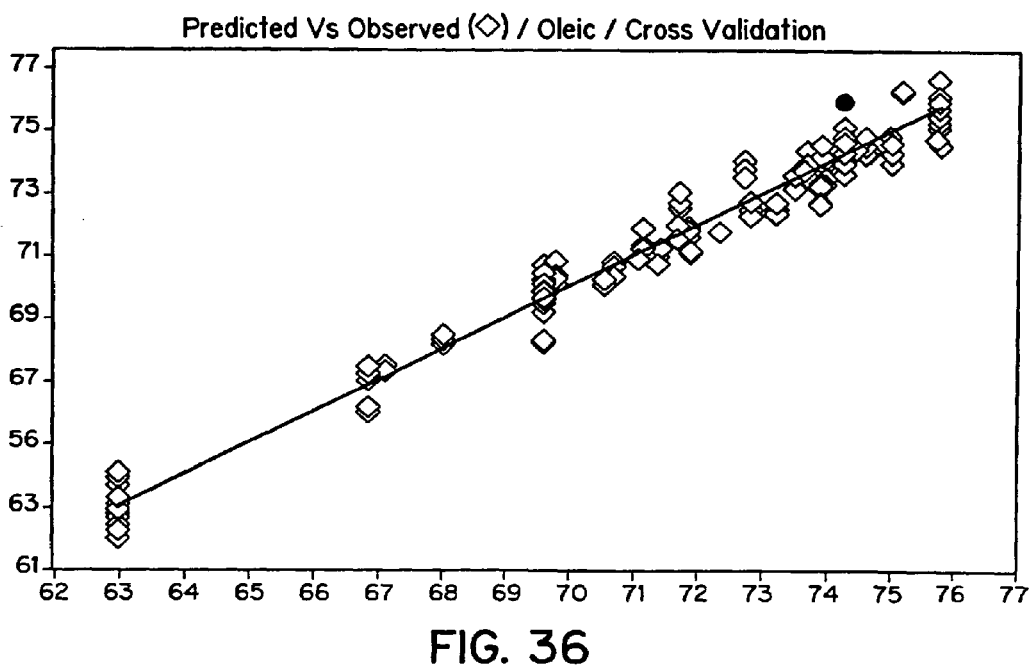
FIG. 36 is predicted versus observed values from the cross-validation of Model 11.1.

Model 11.1 was a multi-instrument global property model (block 104, FIG. 5) constructed to predict the oleic oil content using a refined filter (block 160, FIG. 6) of two spectral subregions, 4246.5 cm$^{-1}$ to 4601.4 cm$^{-1}$ and 5449.9 cm$^{-1}$ to 7501.8 cm$^{-1}$. Data pretreatment also included a first-derivative transformation with 17 smoothing points followed by vector normalization. Cross-validation of Model 11.1 gave 98.01 for $R^2$ and 0.525% for RMSECV with a rank of 14 within the concentration range from 63.00% to 75.72%. The calibration curve for Model 11.1 is shown in FIG. 36. The observed and predicted values from the extended training set of Model 11.1 for oleic oil are in Table 14.

TABLE 14

| Spectrum | Sample | Observed (%) | Predicted (%) | Residual (Obs − Pred) |
|---|---|---|---|---|
| 1 | 1 | 72.82 | 72.59 | 0.23 |
| 2 | 1 | 72.82 | 72.33 | 0.49 |
| 3 | 1 | 72.82 | 72.72 | 0.10 |
| 4 | 2 | 74.25 | 74.14 | 0.11 |
| 5 | 2 | 74.25 | 74.55 | −0.30 |
| 6 | 2 | 74.25 | 74.41 | −0.16 |
| 7 | 5 | 69.62 | 69.15 | 0.47 |
| 8 | 5 | 69.62 | 70.44 | −0.82 |
| 9 | 5 | 69.62 | 70.46 | −0.84 |
| 10 | 6 | 74.25 | 73.86 | 0.39 |
| 11 | 6 | 74.25 | 74.02 | 0.23 |
| 12 | 6 | 74.25 | 74.17 | 0.08 |
| 13 | 7 | 73.91 | 73.29 | 0.62 |
| 14 | 7 | 73.91 | 73.52 | 0.39 |
| 15 | 7 | 73.91 | 73.19 | 0.72 |
| 16 | 8 | 73.22 | 72.49 | 0.73 |
| 17 | 8 | 73.22 | 72.45 | 0.77 |
| 18 | 8 | 73.22 | 72.71 | 0.51 |
| 19 | 9 | 71.18 | 71.45 | −0.27 |
| 20 | 9 | 71.18 | 71.22 | −0.04 |
| 21 | 9 | 71.18 | 71.83 | −0.65 |
| 22 | 10 | 74.64 | 74.35 | 0.29 |
| 23 | 10 | 74.64 | 74.67 | −0.03 |
| 24 | 10 | 74.64 | 74.63 | 0.01 |
| 25 | 11 | 74.59 | 74.47 | 0.12 |
| 26 | 11 | 74.59 | 74.65 | −0.06 |
| 27 | 11 | 74.59 | 74.77 | −0.18 |
| 28 | 12 | 74.39 | 74.48 | −0.09 |
| 29 | 12 | 74.39 | 74.47 | −0.08 |
| 30 | 12 | 74.39 | 74.27 | 0.12 |
| 31 | 13 | 73.48 | 73.31 | 0.17 |
| 32 | 13 | 73.48 | 73.58 | −0.10 |
| 33 | 13 | 73.48 | 73.54 | −0.06 |
| 34 | 14 | 73.98 | 73.87 | 0.11 |
| 35 | 14 | 73.98 | 73.35 | 0.63 |
| 36 | 14 | 73.98 | 73.53 | 0.45 |
| 37 | 15 | 73.49 | 73.58 | −0.09 |
| 38 | 15 | 73.49 | 73.20 | 0.29 |
| 39 | 15 | 73.49 | 73.16 | 0.33 |
| 40 | 16 | 75.01 | 74.37 | 0.64 |
| 41 | 16 | 75.01 | 74.00 | 1.01 |
| 42 | 16 | 75.01 | 74.29 | 0.72 |
| 43 | 17 | 71.71 | 72.41 | −0.70 |
| 44 | 17 | 71.71 | 72.57 | −0.86 |
| 45 | 17 | 71.71 | 72.99 | −1.28 |
| 46 | 18 | 73.87 | 74.35 | −0.48 |
| 47 | 18 | 73.87 | 74.10 | −0.23 |
| 48 | 18 | 73.87 | 73.47 | 0.40 |
| 49 | 19 | 68.05 | 68.20 | −0.15 |
| 50 | 19 | 68.05 | 68.34 | −0.29 |
| 51 | 19 | 68.05 | 68.42 | −0.37 |
| 52 | 20 | 71.87 | 71.59 | 0.28 |
| 53 | 20 | 71.87 | 71.92 | −0.05 |
| 54 | 20 | 71.87 | 71.82 | 0.05 |
| 55 | 21 | 74.96 | 74.67 | 0.29 |
| 56 | 21 | 74.96 | 74.91 | 0.05 |
| 57 | 21 | 74.96 | 74.63 | 0.33 |
| 58 | 22 | 70.74 | 70.79 | −0.05 |
| 59 | 22 | 70.74 | 70.66 | 0.08 |
| 60 | 22 | 70.74 | 70.31 | 0.43 |
| 61 | 23 | 71.68 | 71.50 | 0.18 |
| 62 | 23 | 71.68 | 71.53 | 0.15 |
| 63 | 23 | 71.68 | 71.97 | −0.29 |
| 64 | 24 | 70.54 | 70.32 | 0.22 |
| 65 | 24 | 70.54 | 70.31 | 0.23 |
| 66 | 24 | 70.54 | 70.04 | 0.50 |
| 67 | 25 | 63.00 | 62.45 | 0.55 |
| 68 | 25 | 63.00 | 62.83 | 0.17 |
| 69 | 25 | 63.00 | 62.65 | 0.35 |
| 70 | 26 | 75.18 | 76.22 | −1.04 |
| 71 | 26 | 75.18 | 76.31 | −1.13 |
| 72 | 28 | 73.89 | 73.36 | 0.53 |
| 73 | 28 | 73.89 | 73.91 | −0.02 |
| 74 | 28 | 73.89 | 74.07 | −0.18 |
| 75 | 29 | 75.72 | 76.04 | −0.32 |
| 76 | 29 | 75.72 | 76.62 | −0.90 |
| 77 | 29 | 75.72 | 75.26 | 0.46 |
| 78 | 30 | 73.67 | 74.35 | −0.68 |
| 79 | 30 | 73.67 | 73.46 | 0.21 |
| 80 | 30 | 73.67 | 73.96 | −0.29 |
| 81 | 31 | 73.88 | 73.22 | 0.66 |
| 82 | 31 | 73.88 | 73.81 | 0.07 |
| 83 | 31 | 73.88 | 74.13 | −0.25 |
| 84 | 32 | 71.89 | 71.06 | 0.83 |
| 85 | 32 | 71.89 | 71.28 | 0.61 |
| 86 | 32 | 71.89 | 71.29 | 0.60 |
| 87 | 33 | 67.13 | 67.48 | −0.35 |
| 88 | 33 | 67.13 | 67.29 | −0.16 |
| 89 | 33 | 67.13 | 67.29 | −0.16 |
| 90 | 34 | 66.89 | 66.99 | −0.10 |
| 91 | 34 | 66.89 | 67.17 | −0.28 |
| 92 | 34 | 66.89 | 67.31 | −0.42 |
| 93 | 35 | 72.72 | 73.84 | −1.12 |
| 94 | 35 | 72.72 | 73.52 | −0.80 |
| 95 | 35 | 72.72 | 73.50 | −0.78 |
| 96 | 36 | 71.12 | 71.03 | 0.09 |
| 97 | 36 | 71.12 | 71.04 | 0.08 |
| 98 | 36 | 71.12 | 70.85 | 0.27 |
| 99 | 37 | 71.39 | 70.96 | 0.43 |
| 100 | 37 | 71.39 | 70.77 | 0.62 |
| 101 | 37 | 71.39 | 71.25 | 0.14 |
| 102 | 41 | 71.43 | 71.26 | 0.17 |
| 103 | 41 | 71.43 | 71.24 | 0.19 |
| 104 | 42 | 72.36 | 71.80 | 0.56 |
| 105 | 42 | 72.36 | 71.79 | 0.57 |
| 106 | 43 | 73.67 | 73.91 | −0.24 |
| 107 | 43 | 73.67 | 73.69 | −0.02 |
| 108 | 43 | 73.67 | 73.89 | −0.22 |
| 109 | 28 | 73.89 | 73.20 | 0.69 |
| 110 | 28 | 73.89 | 73.36 | 0.53 |
| 111 | 29 | 75.72 | 75.53 | 0.19 |
| 112 | 29 | 75.72 | 75.35 | 0.37 |
| 113 | 29 | 75.72 | 75.49 | 0.23 |
| 114 | 2 | 74.25 | 74.85 | −0.60 |
| 115 | 2 | 74.25 | 74.71 | −0.46 |
| 116 | 2 | 74.25 | 74.73 | −0.48 |
| 117 | 5 | 69.62 | 70.04 | −0.42 |
| 118 | 5 | 69.62 | 69.40 | 0.22 |
| 119 | 5 | 69.62 | 69.98 | −0.36 |
| 120 | 25 | 63.00 | 63.24 | −0.24 |
| 121 | 25 | 63.00 | 63.15 | −0.15 |
| 122 | 25 | 63.00 | 63.61 | −0.61 |
| 123 | 28 | 73.89 | 74.44 | −0.55 |
| 124 | 28 | 73.89 | 74.10 | −0.21 |
| 125 | 28 | 73.89 | 73.94 | −0.05 |
| 126 | 29 | 75.72 | 75.02 | 0.70 |
| 127 | 29 | 75.72 | 75.58 | 0.14 |
| 128 | 29 | 75.72 | 75.25 | 0.47 |
| 129 | 2 | 74.25 | 74.50 | −0.25 |
| 130 | 2 | 74.25 | 74.10 | 0.15 |
| 131 | 2 | 74.25 | 74.58 | −0.33 |
| 132 | 5 | 69.62 | 70.21 | −0.59 |
| 133 | 5 | 69.62 | 70.60 | −0.98 |
| 134 | 5 | 69.62 | 70.32 | −0.70 |
| 135 | 25 | 63.00 | 63.22 | −0.22 |
| 136 | 25 | 63.00 | 63.22 | −0.22 |
| 137 | 25 | 63.00 | 62.80 | 0.20 |
| 138 | 5 | 69.78 | 70.79 | −1.01 |
| 139 | 5 | 69.78 | 70.81 | −1.03 |
| 140 | 5 | 69.78 | 70.13 | −0.35 |
| 141 | 5 | 69.78 | 70.18 | −0.40 |
| 142 | 5 | 69.78 | 70.20 | −0.42 |
| 143 | 5 | 69.78 | 70.25 | −0.47 |
| 144 | 5 | 69.78 | 70.29 | −0.51 |
| 145 | 5 | 69.78 | 70.23 | −0.45 |
| 146 | 2 | 74.25 | 73.69 | 0.56 |
| 147 | 2 | 74.25 | 73.65 | 0.60 |
| 148 | 25 | 63.00 | 63.30 | −0.30 |
| 149 | 25 | 63.00 | 63.74 | −0.74 |
| 150 | 28 | 73.89 | 74.01 | −0.12 |
| 151 | 28 | 73.89 | 74.34 | −0.45 |
| 152 | 29 | 75.72 | 75.88 | −0.16 |
| 153 | 2 | 74.25 | 73.82 | 0.43 |
| 154 | 5 | 69.62 | 70.12 | −0.50 |

TABLE 14-continued

| Spectrum | Sample | Observed (%) | Predicted (%) | Residual (Obs − Pred) |
|---|---|---|---|---|
| 155 | 5 | 69.62 | 69.56 | 0.06 |
| 156 | 25 | 63.00 | 62.94 | 0.06 |
| 157 | 25 | 63.00 | 61.93 | 1.07 |
| 158 | 28 | 73.89 | 74.11 | −0.22 |
| 159 | 28 | 73.89 | 72.76 | 1.13 |
| 160 | 29 | 75.72 | 74.64 | 1.08 |
| 161 | 29 | 75.72 | 76.00 | −0.28 |
| 162 | 2 | 74.25 | 73.84 | 0.41 |
| 163 | 2 | 74.25 | 75.07 | −0.82 |
| 164 | 5 | 69.62 | 69.87 | −0.25 |
| 165 | 5 | 69.62 | 69.87 | −0.25 |
| 166 | 25 | 63.00 | 62.91 | 0.09 |
| 167 | 25 | 63.00 | 63.00 | 0.00 |
| 168 | 28 | 73.89 | 73.15 | 0.74 |
| 169 | 28 | 73.89 | 73.22 | 0.67 |
| 170 | 29 | 75.72 | 75.71 | 0.01 |
| 171 | 29 | 75.72 | 75.85 | −0.13 |
| 172 | 5 | 69.62 | 68.27 | 1.35 |
| 173 | 5 | 69.62 | 68.23 | 1.39 |
| 174 | 28 | 73.89 | 72.56 | 1.33 |
| 175 | 28 | 73.89 | 74.08 | −0.19 |
| 176 | 2 | 74.25 | 75.83 | −1.58 |
| 177 | 2 | 74.25 | 74.79 | −0.54 |
| 178 | 25 | 63.00 | 62.74 | 0.26 |
| 179 | 25 | 63.00 | 63.94 | −0.94 |
| 180 | 29 | 75.72 | 76.12 | −0.40 |
| 181 | 29 | 75.72 | 75.33 | 0.39 |
| 182 | 2 | 74.25 | 74.24 | 0.01 |
| 183 | 2 | 74.25 | 74.63 | −0.38 |
| 184 | 5 | 69.62 | 69.57 | 0.05 |
| 185 | 5 | 69.62 | 69.56 | 0.06 |
| 186 | 25 | 63.00 | 64.02 | −1.02 |
| 187 | 25 | 63.00 | 62.89 | 0.11 |
| 188 | 28 | 73.89 | 74.12 | −0.23 |
| 189 | 28 | 73.89 | 74.57 | −0.68 |
| 190 | 29 | 75.72 | 75.45 | 0.27 |
| 191 | 29 | 75.72 | 75.65 | 0.07 |
| 192 | 25 | 63.00 | 62.23 | 0.77 |
| 193 | 25 | 63.00 | 63.23 | −0.23 |
| 194 | 29 | 75.72 | 75.66 | 0.06 |
| 195 | 29 | 75.72 | 75.90 | −0.18 |

Figure 37:
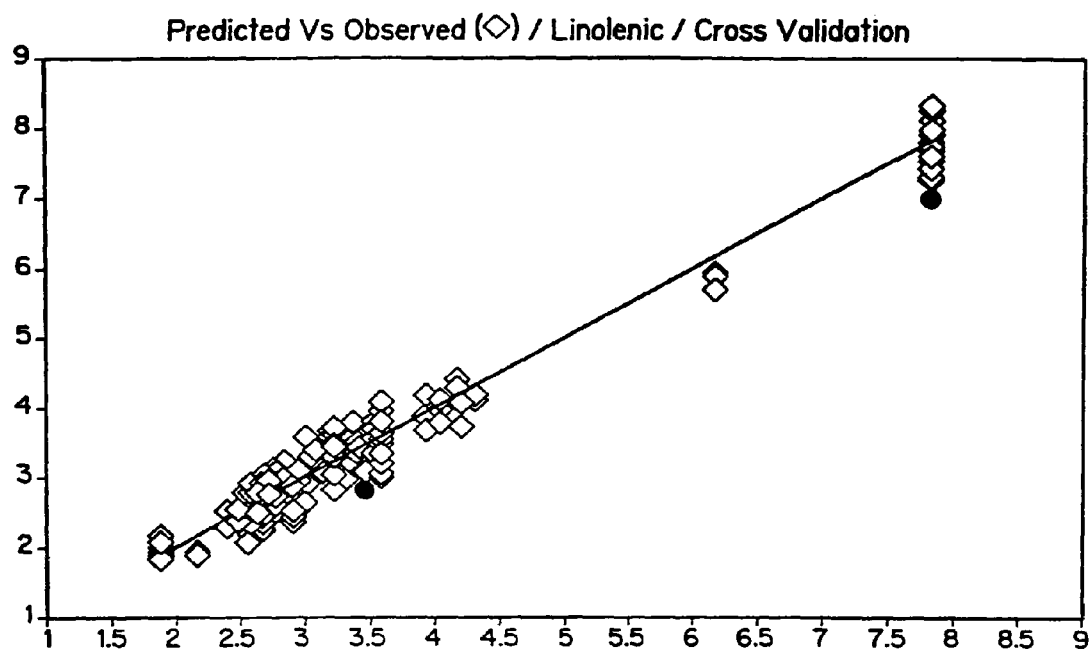
FIG. 37 is predicted versus observed values from the cross-validation of Model 11.2.

Model 11.2 was a multi-instrument global property model (block 104, FIG. 5) constructed to predict linolenic oil content using a refined filter (block 160, FIG. 6) of one spectral subregion, 4616.8 cm$^{-1}$ to 6067.0 cm$^{-1}$. Data pretreatment also included a first-derivative transformation with 17 smoothing points followed by vector normalization. Cross-validation of Model 11.2 gave 96.79 for $R^2$ and 0.262% for RMSECV with a rank of 13 within the concentration range from 1.88% to 7.82%. The calibration curve for Model 11.2 is shown in FIG. 37. The observed and predicted values from the extended training set of Model 11.2 for linolenic oil are in Table 15.

TABLE 15

| Spectrum | Sample | Observed (%) | Predicted (%) | Residual (Obs − Pred) |
|---|---|---|---|---|
| 1 | 1 | 2.75 | 3.27 | −0.52 |
| 2 | 1 | 2.75 | 2.95 | −0.20 |
| 3 | 1 | 2.75 | 3.00 | −0.25 |
| 4 | 2 | 2.67 | 2.28 | 0.39 |
| 5 | 2 | 2.67 | 2.50 | 0.17 |
| 6 | 2 | 2.67 | 2.49 | 0.18 |
| 7 | 3 | 3.92 | 4.28 | −0.36 |
| 8 | 3 | 3.92 | 3.94 | −0.02 |
| 9 | 3 | 3.92 | 3.71 | 0.21 |
| 10 | 4 | 4.05 | 4.02 | 0.03 |
| 11 | 4 | 4.05 | 4.10 | −0.05 |
| 12 | 4 | 4.05 | 3.82 | 0.23 |
| 13 | 5 | 3.57 | 3.47 | 0.10 |
| 14 | 5 | 3.57 | 3.54 | 0.03 |
| 15 | 5 | 3.57 | 3.62 | −0.05 |
| 16 | 6 | 2.93 | 2.95 | −0.02 |
| 17 | 6 | 2.93 | 2.63 | 0.30 |
| 18 | 6 | 2.93 | 2.93 | 0.00 |
| 19 | 7 | 2.79 | 2.72 | 0.07 |
| 20 | 7 | 2.79 | 2.65 | 0.14 |
| 21 | 7 | 2.79 | 2.68 | 0.11 |
| 22 | 8 | 2.86 | 2.97 | −0.11 |
| 23 | 8 | 2.86 | 2.85 | 0.01 |
| 24 | 8 | 2.86 | 3.00 | −0.14 |
| 25 | 9 | 3.19 | 3.23 | −0.04 |
| 26 | 9 | 3.19 | 3.55 | −0.36 |
| 27 | 9 | 3.19 | 3.42 | −0.23 |
| 28 | 10 | 2.40 | 2.41 | −0.01 |
| 29 | 10 | 2.40 | 2.34 | 0.06 |
| 30 | 10 | 2.40 | 2.25 | 0.15 |
| 31 | 11 | 2.68 | 2.65 | 0.03 |
| 32 | 11 | 2.68 | 2.43 | 0.25 |
| 33 | 11 | 2.68 | 2.74 | −0.06 |
| 34 | 12 | 2.65 | 2.98 | −0.33 |
| 35 | 12 | 2.65 | 2.76 | −0.11 |
| 36 | 12 | 2.65 | 2.66 | −0.01 |
| 37 | 13 | 2.54 | 2.68 | −0.14 |
| 38 | 13 | 2.54 | 2.45 | 0.09 |
| 39 | 13 | 2.54 | 2.86 | −0.32 |
| 40 | 14 | 2.70 | 2.66 | 0.04 |
| 41 | 14 | 2.70 | 2.59 | 0.11 |
| 42 | 14 | 2.70 | 2.59 | 0.11 |
| 43 | 15 | 3.00 | 2.79 | 0.21 |
| 44 | 15 | 3.00 | 2.85 | 0.15 |
| 45 | 15 | 3.00 | 2.85 | 0.15 |
| 46 | 16 | 2.48 | 2.64 | −0.16 |
| 47 | 16 | 2.48 | 2.54 | −0.06 |
| 48 | 16 | 2.48 | 2.35 | 0.13 |
| 49 | 17 | 3.16 | 2.90 | 0.26 |
| 50 | 17 | 3.16 | 3.10 | 0.06 |
| 51 | 17 | 3.16 | 2.98 | 0.18 |
| 52 | 18 | 2.92 | 2.38 | 0.54 |
| 53 | 18 | 2.92 | 2.41 | 0.51 |
| 54 | 18 | 2.92 | 2.80 | 0.12 |
| 55 | 20 | 3.19 | 3.82 | −0.63 |
| 56 | 20 | 3.19 | 3.72 | −0.53 |
| 57 | 20 | 3.19 | 3.74 | −0.55 |
| 58 | 21 | 2.59 | 2.61 | −0.02 |
| 59 | 21 | 2.59 | 2.53 | 0.06 |
| 60 | 21 | 2.59 | 2.80 | −0.21 |
| 61 | 22 | 3.37 | 3.63 | −0.26 |
| 62 | 22 | 3.37 | 3.46 | −0.09 |
| 63 | 22 | 3.37 | 3.87 | −0.50 |
| 64 | 23 | 3.33 | 3.37 | −0.04 |
| 65 | 23 | 3.33 | 3.33 | 0.00 |
| 66 | 23 | 3.33 | 3.38 | −0.05 |
| 67 | 24 | 4.31 | 4.40 | −0.09 |
| 68 | 24 | 4.31 | 3.99 | 0.32 |
| 69 | 24 | 4.31 | 4.06 | 0.25 |
| 70 | 25 | 7.82 | 7.87 | −0.05 |
| 71 | 25 | 7.82 | 7.71 | 0.11 |
| 72 | 25 | 7.82 | 7.68 | 0.14 |
| 73 | 26 | 2.57 | 2.15 | 0.42 |
| 74 | 26 | 2.57 | 2.12 | 0.45 |
| 75 | 26 | 2.57 | 2.37 | 0.20 |
| 76 | 27 | 1.88 | 2.09 | −0.21 |
| 77 | 27 | 1.88 | 1.76 | 0.12 |
| 78 | 27 | 1.88 | 1.99 | −0.11 |
| 79 | 28 | 3.22 | 3.27 | −0.05 |
| 80 | 28 | 3.22 | 3.32 | −0.10 |
| 81 | 28 | 3.22 | 3.40 | −0.18 |
| 82 | 29 | 2.58 | 2.68 | −0.10 |
| 83 | 29 | 2.58 | 2.37 | 0.21 |
| 84 | 29 | 2.58 | 2.74 | −0.16 |
| 85 | 30 | 2.77 | 2.60 | 0.17 |
| 86 | 30 | 2.77 | 2.56 | 0.21 |
| 87 | 30 | 2.77 | 2.54 | 0.23 |
| 88 | 31 | 2.79 | 2.88 | −0.09 |
| 89 | 31 | 2.79 | 3.12 | −0.33 |

TABLE 15-continued

| Spectrum | Sample | Observed (%) | Predicted (%) | Residual (Obs − Pred) |
|---|---|---|---|---|
| 90 | 31 | 2.79 | 2.87 | −0.08 |
| 91 | 32 | 2.85 | 3.28 | −0.43 |
| 92 | 32 | 2.85 | 3.26 | −0.41 |
| 93 | 32 | 2.85 | 3.06 | −0.21 |
| 94 | 33 | 4.17 | 4.27 | −0.10 |
| 95 | 33 | 4.17 | 4.33 | −0.16 |
| 96 | 33 | 4.17 | 4.21 | −0.04 |
| 97 | 34 | 6.17 | 5.89 | 0.28 |
| 98 | 34 | 6.17 | 5.88 | 0.29 |
| 99 | 34 | 6.17 | 5.78 | 0.39 |
| 100 | 35 | 2.95 | 2.84 | 0.11 |
| 101 | 35 | 2.95 | 2.93 | 0.02 |
| 102 | 35 | 2.95 | 3.01 | −0.06 |
| 103 | 36 | 3.38 | 3.41 | −0.03 |
| 104 | 36 | 3.38 | 3.38 | 0.00 |
| 105 | 36 | 3.38 | 3.34 | 0.04 |
| 106 | 37 | 3.40 | 3.61 | −0.21 |
| 107 | 37 | 3.40 | 3.44 | −0.04 |
| 108 | 37 | 3.40 | 3.36 | 0.04 |
| 109 | 38 | 2.79 | 2.32 | 0.47 |
| 110 | 38 | 2.79 | 2.22 | 0.57 |
| 111 | 39 | 3.04 | 3.06 | −0.02 |
| 112 | 39 | 3.04 | 2.97 | 0.07 |
| 113 | 39 | 3.04 | 3.04 | 0.00 |
| 114 | 41 | 3.08 | 3.29 | −0.21 |
| 115 | 41 | 3.08 | 3.33 | −0.25 |
| 116 | 42 | 2.90 | 2.83 | 0.07 |
| 117 | 42 | 2.90 | 2.86 | 0.04 |
| 118 | 42 | 2.90 | 3.01 | −0.11 |
| 119 | 43 | 3.31 | 3.30 | 0.01 |
| 120 | 43 | 3.31 | 3.29 | 0.02 |
| 121 | 43 | 3.31 | 2.91 | 0.40 |
| 122 | 44 | 2.64 | 2.40 | 0.24 |
| 123 | 44 | 2.64 | 2.44 | 0.20 |
| 124 | 44 | 2.64 | 2.50 | 0.14 |
| 125 | 28 | 3.22 | 3.78 | −0.56 |
| 126 | 28 | 3.22 | 3.61 | −0.39 |
| 127 | 28 | 3.22 | 3.31 | −0.09 |
| 128 | 29 | 2.58 | 2.59 | −0.01 |
| 129 | 29 | 2.58 | 2.70 | −0.12 |
| 130 | 29 | 2.58 | 2.82 | −0.24 |
| 131 | 27 | 1.88 | 2.35 | −0.47 |
| 132 | 27 | 1.88 | 2.27 | −0.39 |
| 133 | 27 | 1.88 | 2.29 | −0.41 |
| 134 | 2 | 2.67 | 2.35 | 0.32 |
| 135 | 2 | 2.67 | 2.34 | 0.33 |
| 136 | 2 | 2.67 | 2.65 | 0.02 |
| 137 | 5 | 3.57 | 3.11 | 0.46 |
| 138 | 5 | 3.57 | 3.36 | 0.21 |
| 139 | 5 | 3.57 | 3.21 | 0.36 |
| 140 | 25 | 7.82 | 7.32 | 0.50 |
| 141 | 25 | 7.82 | 7.31 | 0.51 |
| 142 | 25 | 7.82 | 6.99 | 0.83 |
| 143 | 28 | 3.22 | 3.09 | 0.13 |
| 144 | 28 | 3.22 | 3.00 | 0.22 |
| 145 | 28 | 3.22 | 3.16 | 0.06 |
| 146 | 29 | 2.58 | 2.49 | 0.09 |
| 147 | 29 | 2.58 | 2.42 | 0.16 |
| 148 | 29 | 2.58 | 2.33 | 0.25 |
| 149 | 27 | 1.88 | 2.14 | −0.26 |
| 150 | 27 | 1.88 | 2.13 | −0.25 |
| 151 | 27 | 1.88 | 2.01 | −0.13 |
| 152 | 2 | 2.67 | 2.71 | −0.04 |
| 153 | 2 | 2.67 | 2.74 | −0.07 |
| 154 | 2 | 2.67 | 2.74 | −0.07 |
| 155 | 5 | 3.57 | 3.58 | −0.01 |
| 156 | 5 | 3.57 | 3.53 | 0.04 |
| 157 | 5 | 3.57 | 3.62 | −0.05 |
| 158 | 25 | 7.82 | 7.61 | 0.21 |
| 159 | 25 | 7.82 | 8.08 | −0.26 |
| 160 | 25 | 7.82 | 8.22 | −0.40 |
| 161 | 2 | 2.67 | 2.61 | 0.06 |
| 162 | 2 | 2.67 | 2.52 | 0.15 |
| 163 | 5 | 3.57 | 3.19 | 0.38 |
| 164 | 5 | 3.57 | 3.59 | −0.02 |
| 165 | 25 | 7.82 | 8.09 | −0.27 |
| 166 | 25 | 7.82 | 7.79 | 0.03 |
| 167 | 28 | 3.22 | 3.56 | −0.34 |
| 168 | 28 | 3.22 | 3.55 | −0.33 |
| 169 | 29 | 2.58 | 2.26 | 0.32 |
| 170 | 29 | 2.58 | 2.51 | 0.07 |
| 171 | 2 | 2.67 | 2.25 | 0.42 |
| 172 | 2 | 2.67 | 2.47 | 0.20 |
| 173 | 5 | 3.57 | 3.83 | −0.26 |
| 174 | 5 | 3.57 | 4.14 | −0.57 |
| 175 | 25 | 7.82 | 7.80 | 0.02 |
| 176 | 25 | 7.82 | 7.57 | 0.25 |
| 177 | 28 | 3.22 | 3.17 | 0.05 |
| 178 | 28 | 3.22 | 2.62 | 0.60 |
| 179 | 29 | 2.58 | 2.37 | 0.21 |
| 180 | 29 | 2.58 | 2.68 | −0.10 |
| 181 | 2 | 2.67 | 2.62 | 0.05 |
| 182 | 2 | 2.67 | 2.99 | −0.32 |
| 183 | 5 | 3.57 | 3.50 | 0.07 |
| 184 | 5 | 3.57 | 3.74 | −0.17 |
| 185 | 25 | 7.82 | 7.41 | 0.41 |
| 186 | 25 | 7.82 | 8.11 | −0.29 |
| 187 | 28 | 3.22 | 3.25 | −0.03 |
| 188 | 28 | 3.22 | 3.49 | −0.27 |
| 189 | 29 | 2.58 | 2.48 | 0.10 |
| 190 | 29 | 2.58 | 2.35 | 0.23 |
| 191 | 2 | 2.67 | 2.91 | −0.24 |
| 192 | 2 | 2.67 | 2.82 | −0.15 |
| 193 | 5 | 3.57 | 3.85 | −0.28 |
| 194 | 5 | 3.57 | 3.95 | −0.38 |
| 195 | 25 | 7.82 | 7.62 | 0.20 |
| 196 | 25 | 7.82 | 7.91 | −0.09 |
| 197 | 28 | 3.22 | 3.70 | −0.48 |
| 198 | 28 | 3.22 | 3.20 | 0.02 |
| 199 | 29 | 2.58 | 2.73 | −0.15 |
| 200 | 29 | 2.58 | 2.47 | 0.11 |

Occasional missing data in Tables 13 to 15 resulted from omitting observations from the training sets that were identified as bad outliers (block 106, FIG. 5), which occurred when the quality of an acquired spectrum was poor due to unexpected interruptions in the grain flow during data acquisition or if an inaccuracy in the reference data on specific properties of some samples was subsequently identified and could not be corrected.

This example demonstrates that it is possible to build multivariate calibrations over a wide range of expected temperatures (from about −60 to about +50° C.), but including calibration data over such a wide temperature range tends to decrease the precision of predicted results. If it is desired or necessary to increase the precision of predicted results beyond that used in this example, and if it is possible to precondition or ensure that the samples that will be measured at remote locations to a narrower range of temperatures and thereby adjust the objectives of block 82 in FIG. 4, then other models can be built from training sets that span temperatures over a narrower range.

The above three property models were validated using 50 validation samples (block 108, FIG. 5) not used in the training sets by taking measurements over a range of measurement conditions with two Bruker MATRIX Model F FT-NIR instruments in Sensors A and B that had not been used previously. The validation results (block 110, FIG. 5) are shown in Table 16. No outliers were detected in the validation set (block 112, FIG. 5).

TABLE 16

| Property | Range | RMSEP of Sensor A | R² of Sensor A | RMSEP of Sensor B | R² of Sensor B |
|---|---|---|---|---|---|
| Wt % total oil | 40.0-50.19 | 0.52 | 96.08 | 0.55 | 95.47 |
| Wt % oleic oil | 66.85-76.00 | 0.53 | 95.04 | 0.56 | 94.21 |
| Wt % linolenic oil | 1.88-7.50 | 0.25 | 96.85 | 0.26 | 96.92 |

These results showed that the RMSEP values from the validation sets for the three properties were each close to the RMSECV values of the corresponding property models, each were within the desired upper precision limit of 0.6%, and differences in the predicted values from different instruments were not significant. Models 11.0, 11.1 and 11.2 were thus considered to be ready for installation (block 114, FIG. 5) in the central processor 10.

Example 12

The Mahalanobis distance can be used to identify bad outliers which may arise from invalid measurements. For Examples 12 to 15, a threshold value of the Mahalanobis distance for good outliers was calculated by OPUS Quant-2 to be 0.42. The threshold values for bad outliers and for extremely bad outliers were taken to be 1.0 and 100.0, respectively.

Figure 38:
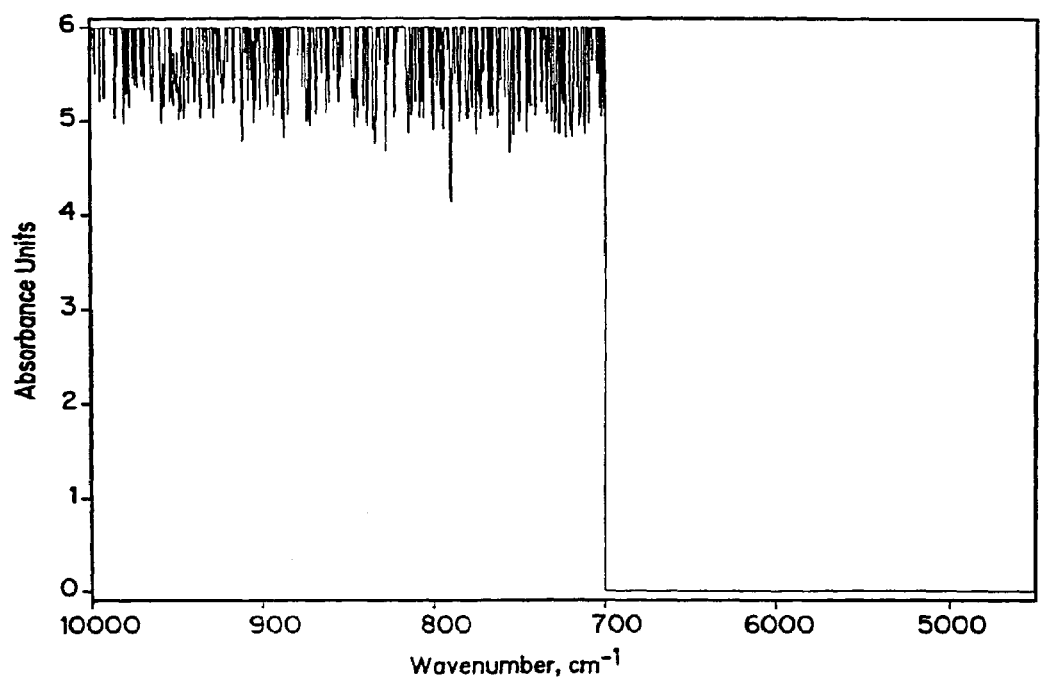
FIG. 38 is an abnormal NIR spectrum resulting from a failed excitation source.

FIG. 38 shows an abnormal FT-NIR spectrum acquired after an instrument malfunction which caused the excitation source to fail. Model 11.1 predicted that the oleic oil in the sample was 199.0%. Since the Mahalanobis distance for this spectrum was 390.00, the predicted value was correctly identified as an extremely bad outlier and the corresponding measurement results were considered invalid.

Example 13

The Mahalanobis distance can be used to identify bad outliers which may arise from invalid sample presentation.

Figure 39:
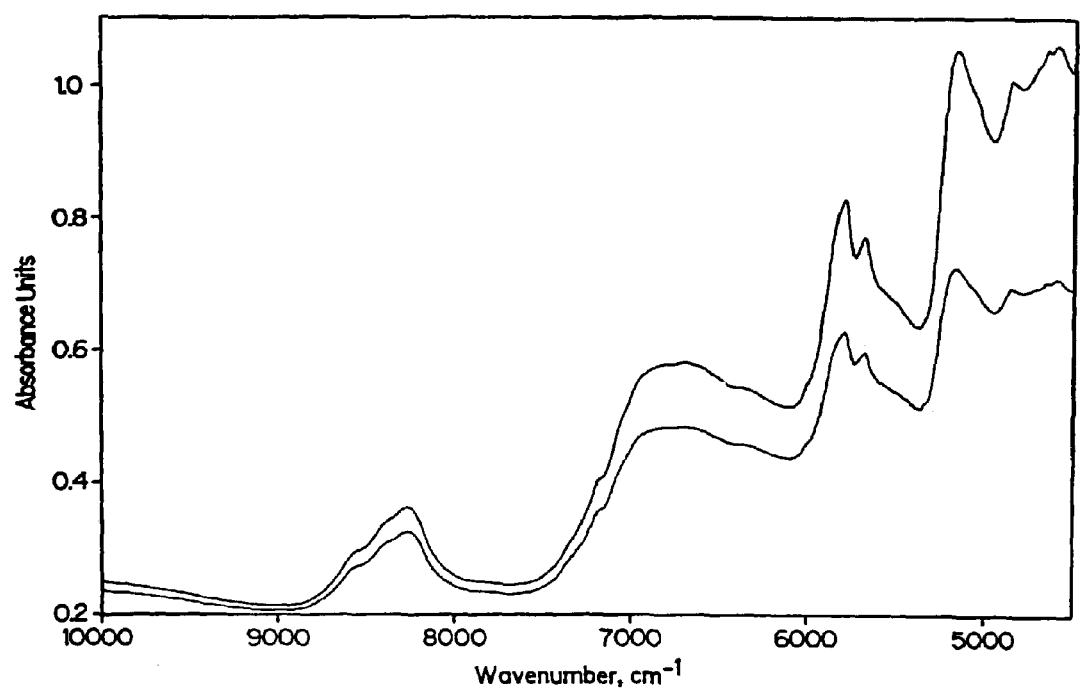
FIG. 39 is superposed NIR spectra of the same sample of canola seed taken using different sampling amounts.

FIG. 39 shows two NIR spectra acquired on the same sample of canola seeds using the flow-through sample presentation system described in Example 11. The known value of oleic oil for this sample was 73.1%. The upper spectrum was taken on a 250 gram sample (a valid sample size according to the method of Example 11), while the lower spectrum was taken on a 100 gram sample (an invalid sample size according to the method of Example 11). Model 11.1 predicted that the oleic oil from the upper spectrum was 73.0% while that of the lower spectrum was 66.1%. Since the Mahalanobis distances of the upper spectrum was 0.25 while that of the lower spectrum was 5.00, the upper spectrum was a presumably valid measurement, while the lower spectrum was correctly identified as a bad outlier and the corresponding measurement results were considered invalid.

Example 14

The Mahalanobis distance can be used to identify bad outliers which may arise from valid measurements on samples taken from populations different from that of the training set.

Figure 40:
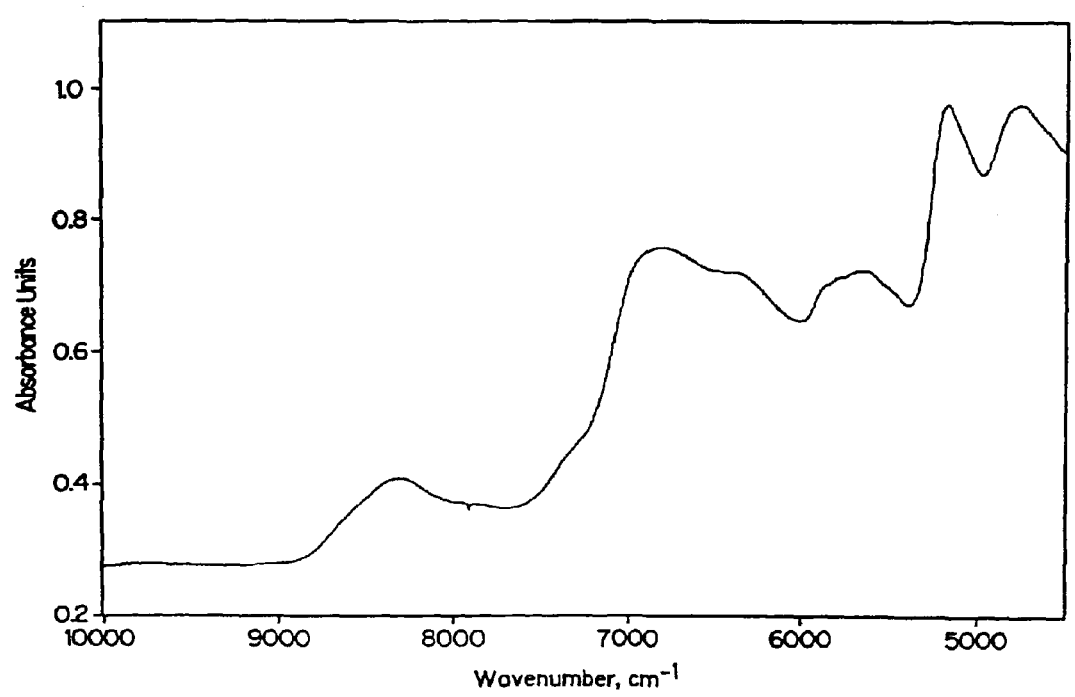
FIG. 40 is a NIR spectrum of wheat.

FIG. 40 shows an NIR spectrum of a sample of wheat using the sample presentation system of Example 11. Model 11.1 predicted that the oleic oil in the sample was 33.2%. Since the Mahalanobis distance of this spectrum was 44.00, the predicted value was correctly identified as a bad outlier and the corresponding measurement results were considered invalid.

Example 15

The Mahalanobis distance can be used to identify good outliers arising from valid measurements on samples with secondary material characteristics that differ in some characteristic way from the secondary material characteristics of samples included in the training set.

Figure 41:
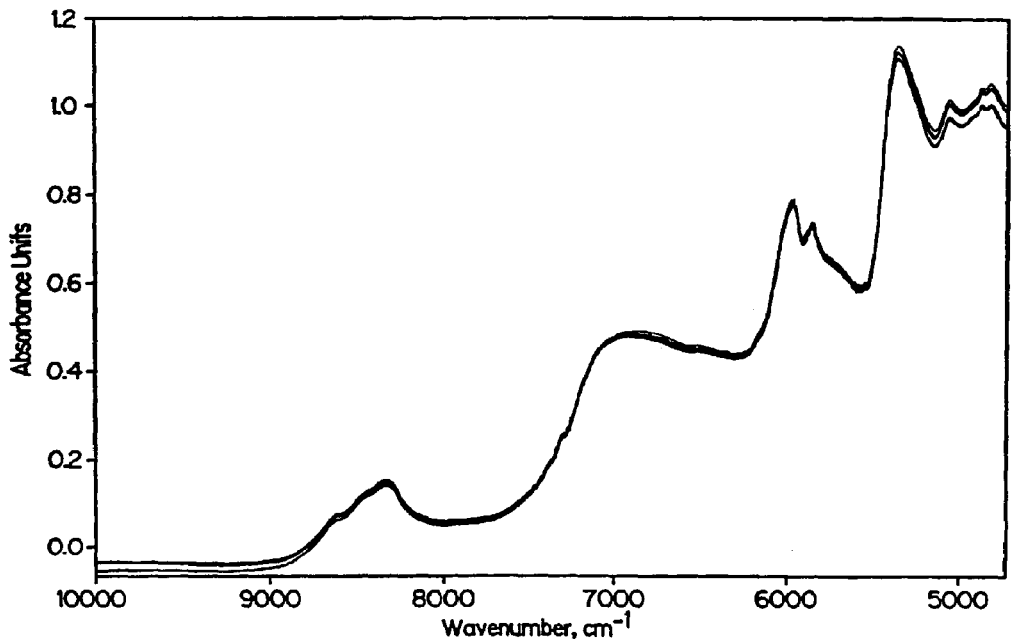
FIG. 41 is superposed NIR spectra of different samples of a single variety of canola seed different from the canola variety of FIG. 34.

FIG. 41 shows six NIR spectra from three different samples of Variety B canola seeds, with duplicate spectra taken for each sample using the sample presentation system of Example 11. Variety B was characteristically different from Variety A, which was the variety of canola used to develop Model 11.1. The observed and predicted values of oleic oil in these three samples according to Model 11.1 is summarized in Table 17. Since the Mahalanobis distance of each spectrum was greater than the threshold value for good outliers, all predicted results on Variety B canola were good outliers and the corresponding measurement results were considered invalid.

TABLE 17

| Sample | Observed | Predicted | MAH |
|---|---|---|---|
| S1 | 72.2% | 73.3%, 73.0% | 0.72, 0.71 |
| S2 | 70.6% | 71.8%, 72.3% | 0.71, 0.73 |
| S3 | 71.3% | 72.6%, 72.2% | 0.86, 0.69 |

Model 15.0 was a property model constructed by including two spectra from sample S1 in the training set of Model 11.1 while maintaining the corresponding refined filter and pretreatment transformations. The results predicted from Model 15.0 using a validation set containing four spectra from samples S2 and S3 are given in Table 18.

TABLE 18

| Sample | Observed | Predicted | MAH |
|---|---|---|---|
| S2 | 70.6% | 70.9%, 71.5% | 0.29, 0.33 |
| S3 | 71.3% | 71.5%, 71.6% | 0.33, 0.29 |

Since the Mahalanobis distances in Table 18 were each less than the threshold for good outliers, the predicted results on Variety B canola are no longer probable outliers. The measurement results in Table 18 are considered valid, and Model 15.0 compensates for a wider range of influential factors.

Example 16

A collection of Bruker MATRIX Model F FT-NIR instruments, sample presentation devices of the type shown in FIG.

33, and laptop computers loaded with Microsoft® Windows® 2000 and the Bruker OPUS 3.01 software were transported to several sites in Canada, remote from the central processor residing in Cincinnati, Ohio. Two remote analysis systems were assembled at two separate sites in Manitoba, Canada by separate personnel, with each sensor 2 comprising one each of the NIR instrument 30, equipped with a sample presentation device 22 (shown in FIG. 33) and a laptop computer serving as the local processor 34. Using appropriate communications software on the local processor 34, the systems were connected to their own separate local area networks with Internet connectivity.

Once Internet connectivity was established, operators at both sites initiated secure connections to the central processor 10, using a graphical user interface on the local processor 34, and entered device-specific unique user identification codes additional remote user action. The measurement data 12 and the measurement results 14 were stored in the data repository 58. The elapsed time from initial user interface prompt to display of predicted values at an output device of the user interface 32 was generally from about 1 to about 2 minutes. The time interval between transmission of the measurement data 12 and transmission of the measurement results 14 was generally less than one minute.

Table 19 lists the measurement results 14 generated from sensors A and B during a short time interval when both sensors were performing near-simultaneous analyses. Table 19 is an example of a report of historical information including two or more measurement results 14 acquired from at least one data acquisition device 2 that was transmitted to at least one user interface as aggregated results.

TABLE 19

| Test No. | Submission Time | Location | Sensor | % Total Oil | Total Oil MAH | % Oleic | Oleic MAH | % Linolenic | Linoleic MAH |
| --- | --- | --- | --- | --- | --- | --- | --- | --- | --- |
| 1 | 12:29 | Manitoba | A | 45.3 | 0.1 | 73.1 | 0.2 | 3.2 | 0.3 |
| 2 | 12:31 | Manitoba | A | 45.0 | 0.1 | 72.6 | 0.3 | 3.2 | 0.1 |
| 3 | 12:31 | Manitoba | B | 50.5 | 0.2 | 76.9 | 0.2 | 2.4 | 0.6 |
| 4 | 12:32 | Manitoba | A | 45.2 | 0.1 | 73.3 | 0.3 | 4.0 | 0.2 |
| 5 | 12:33 | Manitoba | B | 50.5 | 0.3 | 77.1 | 0.2 | 1.9 | 0.7 | and passwords for approval by the security controller 54. Successful connection to the central processor 10 typically occurred within one minute.

Upon connectivity to the central processor 10, the user interface 32 prompted for sample identification. This remote user-supplied sample identification data, along with the subsequently acquired multichannel data, was transmitted to the central processor 10 and used by the analysis engine 56 to select the appropriate parameters from the data repository 58 for three multi-instrument global property models: Model 11.0 for total oil, Model 11.1 for oleic content, and Model 11.2 for linolenic content.

After entering the sample identification data, the operators placed about 250 grams of whole canola seed samples into the funnel 202 of the sample presentation device 22. The funnel gate 208 was opened and the instrument 200 was then activated by the user interface 32 and the flow of the canola was initiated through the sample chamber 24 past the fiber optic probe 204. Within seconds after the sample flow had completed, the measurement data 12 was transmitted over the secure Internet connection 8 to the central processor 10. The analysis engine 56 computed values for the properties of interest based on Models 11.0, 11.1 and 11.2 (block 116, FIG. 5), and after testing for outliers (block 118, FIG. 5) the measurement results 14 were sent back to the individual sensors 2 (block 120, FIG. 5) via Internet connection 8, all without Two of the predicted results in Table 19, test numbers 3 and 5 for linolenic content, were identified as good outliers (blocks 118, 122, and 124 in FIG. 5). Investigation revealed that the corresponding samples were a different variety of canola than that used to develop the calibration models. If during customer consultation it had been learned that the new variety was an experimental crop that would no longer be produced, it might be decided not to extend the training set (block 126, FIG. 5) so any additional samples of the experimental variety would also be considered invalid during future on-site measurements (block 116, FIG. 5). If, however, it had been learned that the new variety was scheduled for continued production, then it could be decided to extend the training set (block 126, FIG. 5) so future measurements using a new property model (developed according to blocks 102, 104, 106, 108, 110, 112 as well as blocks 124, 126, 128, and 130 as required) installed on the central processor 10 (block 114, FIG. 5) would provide valid predictions from on-site measurements (block 116, FIG. 5) for both new and old varieties of canola.

Additionally, as demonstrated by the data in Table 20, analyses were generated on a different date after transporting sensor A to a third remote site in Saskatchewan, Canada, with measurement results 14 being returned to user interface 32 at the third site which submitted data to the central processor 10 with brief lapses over the course of about 30 minutes.

TABLE 20

| Test No. | Submission Time | Location | Sensor | % Total Oil | Total Oil MAH | % Oleic | Oleic MAH | % Linolenic | Linoleic MAH |
| --- | --- | --- | --- | --- | --- | --- | --- | --- | --- |
| 1 | 12:32 | Saskatchewan | A | 47.6 | 0.2 | 76.5 | 0.2 | 2.1 | 0.2 |
| 2 | 12:35 | Saskatchewan | A | 41.6 | 0.2 | 72.3 | 0.2 | 2.8 | 0.2 |
| 3 | 12:37 | Saskatchewan | A | 47.9 | 0.2 | 75.7 | 0.1 | 2.3 | 0.3 |
| 4 | 12:40 | Saskatchewan | A | 47.6 | 0.2 | 75.3 | 0.1 | 2.1 | 0.2 |
| 5 | 12:41 | Saskatchewan | A | 44.1 | 0.1 | 76.0 | 0.1 | 2.2 | 0.2 |
| 6 | 12:44 | Saskatchewan | A | 48.0 | 0.3 | 73.7 | 0.2 | 2.7 | 0.2 |
| 7 | 12:46 | Saskatchewan | A | 41.1 | 0.1 | 70.0 | 0.1 | 3.1 | 0.2 |
| 8 | 12:51 | Saskatchewan | A | 40.8 | 0.2 | 71.1 | 0.1 | 3.1 | 0.2 |
| 9 | 12:54 | Saskatchewan | A | 45.5 | 0.2 | 74.5 | 0.1 | 2.3 | 0.3 |

TABLE 20-continued

| Test No. | Submission Time | Location | Sensor | % Total Oil | Total Oil MAH | % Oleic | Oleic MAH | % Linolenic | Linoleic MAH |
|---|---|---|---|---|---|---|---|---|---|
| 10 | 12:56 | Saskatchewan | A | 46.8 | 0.2 | 75.2 | 0.2 | 2.1 | 0.2 |
| 11 | 12:58 | Saskatchewan | A | 47.5 | 0.1 | 76.7 | 0.1 | 1.7 | 0.3 |
| 12 | 13:00 | Saskatchewan | A | 42.8 | 0.1 | 74.2 | 0.1 | 2.5 | 0.2 |
| 13 | 13:02 | Saskatchewan | A | 48.9 | 0.2 | 76.7 | 0.1 | 2.0 | 0.3 |
| 14 | 13:04 | Saskatchewan | A | 47.1 | 0.2 | 76.3 | 0.1 | 2.1 | 0.2 |

The on-site analysis system is simple to operate at each location where data is acquired. Because only one property model algorithm is needed for each property of interest as specified in the method and objectives of block 70 in FIG. 4, and each of these is stored on the central processor, the operator need only have the sample 20 ready to be detected at the sample presentation device 22 and initiate the data acquisition by following the prompts which appear at the user interface 32. A semiskilled, or even non-skilled operator is able to perform the steps needed to acquire data on the sample.

Also, the analysis system and method enables the customer to submit guidelines to be stored in the data repository 58 via an appropriate security code to the security controller 54 of the central processor 10 to provide annotations to the measurement results 14 to provide customer specific interpretations and help text. Thus, the customer could independently specify whether a particular range of predicted values is a "Pass" or "Fail" for the property of interest. The customer can instruct the central processor 10 to transmit this annotation as appropriate for particular predicted results generated by the property model algorithm. It is also possible for the customer to command the central processor 10 from an off-site user interface 158 to generate custom spreadsheets of historical results for forecasting or quality assurance purposes.

The on-site analysis system and method of analysis can be used in a range of applications for obtaining information on a number of materials. A multi-instrument global property model which can be refined to a high degree of precision, as necessary, and coupled with substantial immunity to instrument, sample, environmental, and sample presentation variance can be used to produce measurement results 14 which are accepted within a particular trade. Thus, it is possible that an on-site analysis system and method of analysis can be devised with proper attention to inclusion of the requisite variables for the creation of a method whereby results can be certified by a sanctioning body. Because the processing of data received from individual sensors 2, 4, 6 is conducted by a single property model algorithm of the central processor 10 for each property of interest without instrument-specific calibration transfer, predicted results from a number of sensors of the same sensor-type can be directly compared and certified.

It is possible using this analysis system and method of analysis to compensate for individual sensor variation at the respective sampling locations. Thus, a global property model can be generated which not only compensates for changes to components in one sensor over time, such as the output of an excitation source, but also compensates for inherent differences between similarly constructed sensors. For the case of spectroscopic instruments, it is preferred that the instrument manufacturer generate a line of equipment with individual instruments being sufficiently similar, having minimized differences as to the following characteristics or components: light intensity; optical parts; alignment of the optical parts; detector performance; and wavelength accuracy.

An additional benefit of using a central processor generating intercomparable results lies in the value generated by archival analysis of historical information which is built up over time. In the case of analyzing oilseeds, for example, information can be stored concerning the specific location of a particular oilseed analysis with the predicted results of that analysis. At the time of the data acquisition, input fields of a user interface can include other information which would be uniquely beneficial for the particular material being analyzed, for example, as part of an electronic identity preservation system. Financial and crop output predictive studies may also utilize this information.

It is anticipated that the analytical system and method of analysis described herein can be utilized in a wide range of applications. These include a number of agriculture-related applications, such as the analysis of oilseed crops, the analysis of grain, electronic grading, farm chemicals blending, soil condition analysis, waste monitoring, plant nutrition analysis, single-seed analysis, determination of harvest readiness, manufacturing of animal feed and forage, dietary supplements, and raw milk and dairy products handling and processing. In the area of healthcare, the system and method can be used in blood analysis, biological sample analysis, skin disease diagnostics, non-invasive human and animal testing, and drug testing. In chemical manufacturing, the system and method can be used in raw material qualification, process control, quality assurance testing, in-process and finished jet, diesel, automotive fuel quality and identity, and effluent monitoring. In textiles, applications include raw materials qualification, fiber properties qualification, blending and application monitoring, and effluent monitoring. In surface treatment, applications include metal treatment analysis, metal wear measurement, coating thickness analysis, and adhesive application measurement. In consumer testing, applications include determination of the fat content of meat, ripeness of fruits and vegetables, automotive fluids check, fuel octane monitoring, exhaust monitoring and personal medical checks, such as for diabetes and cholesterol.

Thus it is apparent that there has been provided, in accordance with the invention, an analysis system, a method of analysis and a method of supplying analysis services to customers which fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, departures may be made from such details without departing from the spirit or scope of the general inventive concept.

What is claimed is:

1. A method for developing a calibration model for use in a central processor configured to generate a predicted value of a property of interest based on an input from one or more data acquisition instruments, comprising:
   obtaining a set of samples having the property of interest;
   generating a first set of data by measuring the property of interest in the samples;

generating a mathematical model of the property of interest using the first set of data;

generating predicted values for the property of interest using the mathematical model;

determining whether the predicted values for the property of interest correlate with the measured values of the property of interest to within a predetermined criterion;

identifying the type and range of a secondary variable that is potentially influential of the measurement of the property of interest;

determining whether the secondary variable is actually influential of the measurement of the property of interest;

adjusting the preliminary model to compensate for the secondary variable and/or identifying an appropriate method of treating responses of the one or more data acquisition instruments to compensate for the secondary variable;

determining whether predicted values of the property of interest generated by the adjusted mathematical model and/or using the treatment method correlate with the measured values within another predetermined criterion when the secondary variable is varied;

generating a second set of data by measuring the property of interest in the samples using the treatment method;

generating a prediction of the property of interest using the second set of data and the revised property model;

determining whether a probable outlier is present in the prediction of the property of interest;

generating a third set of data using the pretreatment method while varying the influential factor;

generating a prediction of the property of interest using the revised property model and the third set of data; and determining whether a probable outlier is present in the prediction of the property of interest generated using the revised property model.

2. The method of claim 1, further comprising determining whether the probable outlier is a good outlier in accordance with another predetermined criterion, and if so, adding the probable outlier to the second set of data, determining a method of treatment to compensate for the probable outlier, and revising the revised model to compensate for the probable outlier.

3. The method of claim 1, wherein the property of interest in the samples spans the range over which the property of interest is expected to vary during actual measurements in the future.

4. The method of claim 1, further comprising determining whether the property of interest is measurable in the presence of variations in the secondary variable to within another predetermined criterion.

5. The method of claim 1, wherein the predetermined criterion is a limit of desired precision.

6. The method of claim 1, wherein determining whether the secondary variable is actually influential of the measurement of the property of interest comprises varying the secondary variable and obtaining measurements of the property of interest.

7. The method of claim 1, wherein identifying an appropriate method of treating responses of the one or more data acquisition instruments to compensate for the secondary variable comprises determining mathematical operations that are used on responses of the data acquisition instrument to compensate for factors that influence the response of the instrument when measuring the property of interest.

8. The method of claim 1, further comprising installing the revised model in the central processor.

9. The method of claim 1, further comprising obtaining a measurement of the property of interest on site and determining whether any outliers exist in the measurement and adjusting the revised model and/or the method of treatment to compensate for the outliers.

10. The method of claim 6, wherein determining whether the secondary variable is actually influential of the measurement of the property of interest comprises determining whether the variation of the secondary variable produces a change in the measured value of the property of interest that is statistically significant to a limit of desired precision in the measured value.

11. The method of claim 1, further comprising notifying the user of the presence of the outliers.

* * * * *